United States Patent
Monn et al.

(10) Patent No.: US 11,534,434 B2
(45) Date of Patent: Dec. 27, 2022

(54) XANOMELINE DERIVATIVES AND METHODS FOR TREATING NEUROLOGICAL DISORDERS

(71) Applicant: Karuna Therapeutics, Inc., Boston, MA (US)

(72) Inventors: James A. Monn, Indianapolis, IN (US); Clifford Adam Schlecht, St. Louis, MO (US); Dennis A. Bennett, Rio Grande, PR (US); Giorgio Attardo, Boston, MA (US)

(73) Assignee: Karuna Therapeutics, Inc., Boston, MA (US)

( * ) Notice: Subject to any disclaimer, the term of this patent is extended or adjusted under 35 U.S.C. 154(b) by 0 days.

(21) Appl. No.: 17/099,214

(22) Filed: Nov. 16, 2020

(65) Prior Publication Data

US 2021/0145810 A1    May 20, 2021

Related U.S. Application Data

(60) Provisional application No. 62/936,000, filed on Nov. 15, 2019.

(51) Int. Cl.
| | |
|---|---|
| *C07D 417/04* | (2006.01) |
| *A61K 31/4439* | (2006.01) |
| *A61K 31/46* | (2006.01) |

(52) U.S. Cl.
CPC .......... *A61K 31/4439* (2013.01); *A61K 31/46* (2013.01); *C07D 417/04* (2013.01)

(58) Field of Classification Search
CPC ............................ A61K 31/4439; A61K 31/46
See application file for complete search history.

(56) References Cited

U.S. PATENT DOCUMENTS

| | | | |
|---|---|---|---|
| 5,376,668 | A | 12/1994 | Sauerberg |
| 5,708,014 | A | 1/1998 | Bodick |
| 5,773,452 | A | 6/1998 | Sauerberg |
| 6,090,829 | A | 7/2000 | Bodick |
| 10,080,755 | B2 | 9/2018 | Dasse |
| 2011/0319386 | A1 | 12/2011 | Barlow |
| 2014/0121407 | A1 | 5/2014 | Muratake |
| 2017/0112820 | A1 | 4/2017 | Elenko |
| 2018/0099956 | A1 | 4/2018 | Abraham |
| 2022/0144817 | A1 | 5/2022 | Bennett |

FOREIGN PATENT DOCUMENTS

| | | |
|---|---|---|
| EP | 0384288 | 8/1990 |
| EP | 0709094 | 5/1996 |
| JP | 2011001308 | 1/2011 |
| WO | 1992003430 | 3/1992 |

(Continued)

OTHER PUBLICATIONS

Veroff, Alzheimer Disease and Associated Disorders, vol. 12(4), 304-312, 1998. (Year: 1998).*
Romero, Bioorg & MEd Chern Lett, vol. 23, 2013, 1916-1922. (Year: 2013).*
Kiesewetter, Nuclear Medicine and Biology, vol. 34, 2007, 141-152. (Year: 2007).*
Vanoosten, Can J Chem, vol. 8, 2010, 1222-1232. (Year: 2010).*
International Application No. PCT/US2020/060734; International Search Report and Written Opinion of the International Searching Authority, dated Feb. 17, 2021; 7 pages.
International Application No. PCT/US2020/019193; International Preliminary Report on Patentability, dated Sep. 9, 2021; 9 pages.
International Application No. PCT/US2020/056629; International Preliminary Report on Patentability, dated May 27, 2022; 5 pages.
Blake, M. et al., "Studies with deuterated drugs", J Pharm Sci., 64(3):367-91, (1975).
Borowicz, K. et al., "Neuroprotective Actions of Neurosteroids", Front Endocrinol., 2(50):p. 1, (2011).
Brinton, R., "Neurosteroids as regenerative agents in the brain: therapeutic implications", Nat Rev Endocrinol., 9(4):241-50, (2013).
Fisher, M. et al., "The complexities inherent in attempts to decrease drug clearance by blocking sites of CYP-mediated metabolism", Curr Opin Drug Discov Devel, 9(1):101-9, (2006).
Foster, A., "Deuterium Isotope Effects in the Metabolism of Drugs and Xenobiotics: Implications for Drug Design", Adv Drug Res., (14):1-40, (1985).

(Continued)

*Primary Examiner* — D Margaret M Seaman
(74) *Attorney, Agent, or Firm* — Global Patent Group, LLC; Lauren L. Stevens; Clifford Schlecht

(57) ABSTRACT

Provided herein are compounds comprising compounds of formula I

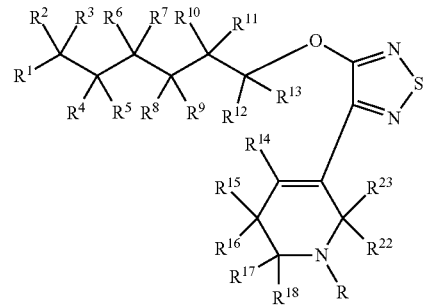

and/or salts thereof;
wherein at least one of $R^1$, $R^2$, $R^3$, $R^4$, $R^5$, $R^6$, $R^7$, $R^8$, $R^9$, $R^{10}$, $R^{11}$, $R^{12}$, and $R^{13}$ is fluorine, and the remainder are independently chosen from hydrogen and fluorine; and $R^{14}$, $R^{15}$, $R^{16}$, $R^{17}$, $R^{18}$, $R^{19}$, $R^{20}$, $R^{21}$, $R^{22}$, and $R^{23}$ are independently chosen from hydrogen and deuterium; with the proviso that when $R^1$, $R^2$, and $R^3$ are fluorine, then at least one of $R^4$, $R^5$, $R^6$, $R^7$, $R^8$, $R^9$, $R^{10}$, $R^{11}$, $R^{12}$, and $R^{13}$ is fluorine or at least one of $R^{14}$, $R^{15}$, $R^{16}$, $R^{17}$, $R^{18}$, $R^{19}$, $R^{20}$, $R^{21}$, $R^{22}$, and $R^{23}$ is deuterium. Also provided are medicaments comprising these compounds and methods for treating central nervous system disorders with the compounds and medicaments described herein.

15 Claims, No Drawings

(56) References Cited

FOREIGN PATENT DOCUMENTS

| | | |
|---|---|---|
| WO | 1992003431 | 3/1992 |
| WO | 1992009280 | 6/1992 |
| WO | 1994020495 | 9/1994 |
| WO | 1995005174 | 2/1995 |
| WO | 1995017185 | 6/1995 |
| WO | 1996014066 | 5/1996 |
| WO | 1997020556 | 6/1997 |
| WO | 2005006858 | 1/2005 |
| WO | 2012006538 | 1/2012 |
| WO | 2012170559 | 12/2012 |
| WO | 2020172516 | 6/2020 |
| WO | 2021097427 | 5/2021 |

OTHER PUBLICATIONS

Fukuto, J. et al., "Determination of the mechanism of demethylenation of (methylenedioxy)phenyl compounds by cytochrome P450 using deuterium isotope effects", J Med Chem., 34(9):2871-6, (1991).

Gannes, L. et al., "Natural Abundance Variations in Stable Isotopes and Their Potential Uses in Animal Physiologica Ecology", Comp Biochem Physiol A Mol Integr Physiol, 119(3):725-37, (1998).

Girard, C. et. al., "Axonal Regeneration and Neuroinflammation: Roles for the Translocator Protein 18 kDa", J Neuroendocrinol., 24(1):71-81, (2011).

Harbeson, S. et al., "Deuterium in Drug Discovery and Development", 46 annual report in medicinal chemistry, 403-417, (2011).

Harbeson, S. et al., "Deuterium Medicinal Chemistry: A New Approach to Drug Discovery and Development", MedChem News, 2, p. 8, (2014).

International Application No. PCT/US2020/019193; International Search Report and Written Opinion of the International Searching Authority, dated May 26, 2020; 13 pages.

Kushner, D. et al., "Pharmacological Uses and Perspectives of Heavy Water and Deuterated Compounds", Can J Physiol Pharmacol., 77(2):79-88, (1999).

Miwa, G. et al., "Kinetic isotope effects and 'metabolic switching' in cytochrome P450-catalyzed reactions", Bioessays, 7(5):215-9, (1987).

Obach, R. et al., "The Prediction of Human Pharmacokinetic Parameters From Preclinical and In Vitro Metabolism Data", J Pharmacol Exp Ther., 283(1):46-58, (1997).

Wilkinson, G., "Drug Metabolism and Variability Among Patients in Drug Response", N Engl J Med., 352(21):2211-21 (2005).

* cited by examiner

XANOMELINE DERIVATIVES AND METHODS FOR TREATING NEUROLOGICAL DISORDERS

This application claims the benefit of priority of U.S. Provisional Patent Application Ser. No. 62/936,000 filed Nov. 15, 2019, the disclosure of which is incorporated by reference in its entirety for all purposes.

The present disclosure relates to new compounds and compositions and their application as pharmaceuticals for treating disease. Methods of treating neurological disorders, such as psychosis and schizophrenia, in a human or animal subject, are also provided.

Xanomeline [3-(hexyloxy)-4-(1-methyl-1,2,5,6-tetrahydropyridin-3-yl)-1,2,5-thiadiazole] is a mixed muscarinic partial agonist across all five muscarinic receptor subtypes:

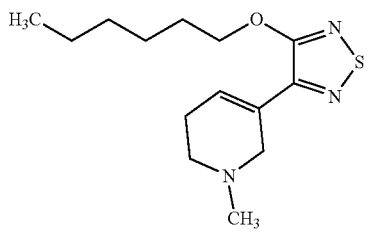 [SMILES: CCCCCCOc1nsnc1C1=CCCN(C)C1]

Activating the muscarinic system through muscarinic agonists may treat several diseases, including schizophrenia, Alzheimer's disease, Parkinson's disease, depression, movement disorders, drug addiction, pain, and neurodegeneration, such as tauopathies or synucleinopathies. Schizophrenia is characterized by a set of symptoms divided into positive symptoms (e.g., hallucinations, delusional thoughts, etc.), negative symptoms (e.g., social isolation, anhedonia, etc.), and cognitive symptoms (e.g., inability to process information, poor working memory, etc. However, the metabolic profile in humans and lack of muscarinic receptor subtype selectivity have been problematic for developing this drug. To reduce the peripheral side effects, xanomeline was reformulated as xanomeline combined with the peripherally restricted broad-spectrum antagonist, trospium, to block peripheral adverse events and is significantly better tolerated.

Thus, certain compounds disclosed herein provide a compound with improved pharmacokinetics (PK), pharmacodynamics (PD), and toxicity profiles. Using these compounds reduces drug exposure variability and the incidence of metabolites. Without wishing to be bound by theory, the first-pass metabolism is avoided via fluorination and/or deuteration of xanomeline at carbon positions susceptible to cytochrome p-450 (CYP) mediated enzymatic oxidation. The tone of binding to the muscarinic receptor is modulated by the position and amount of fluorination on the hexyloxy side chain. Deuteration of the N-methyl and tetrahydropyridine stabilize the molecule from unwanted CYP enzymatic oxidation.

Disclosed herein are compounds having structural Formula I:

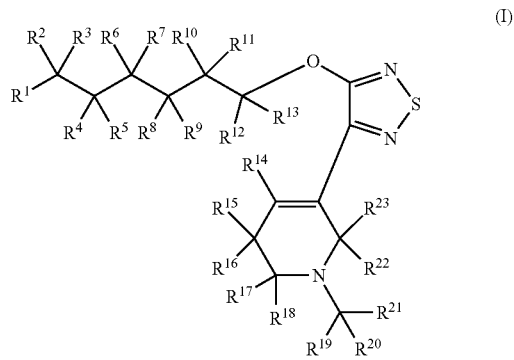

and/or salts thereof; wherein at least one of $R^1$, $R^2$, $R^3$, $R^4$, $R^5$, $R^6$, $R^7$, $R^8$, $R^9$, $R^{10}$, $R^{11}$, $R^{12}$, and $R^{13}$ is fluorine, and the remainder are independently chosen from hydrogen and fluorine; and $R^{14}$, $R^{15}$, $R^{16}$, $R^{17}$, $R^{18}$, $R^{19}$, $R^{20}$, $R^{21}$, $R^{22}$, and $R^{23}$ are independently chosen from hydrogen and deuterium; with the proviso that when $R^1$, $R^2$, and $R^3$ are fluorine, then at least one of $R^4$, $R^5$, $R^6$, $R^7$, $R^8$, $R^9$, $R^{10}$, $R^{11}$, $R^{12}$, and $R^{13}$ is fluorine or at least one of $R^{14}$, $R^{15}$, $R^{16}$, $R^{17}$, $R^{18}$, $R^{19}$, $R^{20}$, $R^{21}$, $R^{22}$ and $R^{23}$ is deuterium In certain embodiments, the compound has structural Formula II

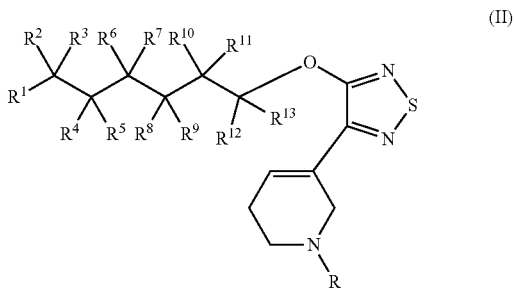

and/or salts thereof; at least one of $R^1$, $R^2$, $R^3$, $R^4$, $R^5$, $R^6$, $R^7$, $R^8$, $R^9$, $R^{10}$, $R^{11}$, $R^{12}$, and $R^{13}$ is fluorine, and the remainder are independently chosen from hydrogen and fluorine; and R is $CH_3$ or $CD_3$; with the proviso that when $R^1$, $R^2$, and $R^3$ are fluorine, then at least one of $R^4$, $R^5$, $R^6$, $R^7$, $R^8$, $R^9$, $R^{10}$, $R^{11}$, $R^{12}$, and $R^{13}$ is fluorine or R is $CD_3$.

DETAILED DESCRIPTION

To aid understanding of the disclosure set forth herein, several terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood in the art to which this disclosure belongs. If there is a plurality of definitions for a term used herein, those in this section prevail unless stated otherwise.

When introducing elements of the present disclosure or the embodiment(s) thereof, the articles "a," "an," "the," and "said" are intended to mean that there are one or more of the elements. The terms "comprising," "including," and "having" are inclusive and mean that there may be additional elements other than the listed elements.

The term "and/or" when in a list of two or more items, means that any of the listed items can be employed by itself or in combination with one or more of the listed items. For example, the expression "A and/or B" means either or both of A and B, i.e., A alone, B alone, or A and B in combination. The expression "A, B and/or C" is intended to mean A alone, B alone, C alone, A and B in combination, A and C in combination, B and C in combination, or A, B, and C in combination.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods, such as mass spectrometry and nuclear magnetic resonance spectroscopy.

The term "is/are deuterium," when used to describe a given position in a molecule such as $R_1$, $R_2$, $R_3$, $R_4$, $R^5$, $R_6$, $R_7$, $R_8$, $R_9$, $R_{10}$, and $R_{11}$ or the symbol "D," when used to represent a given position in a drawing of a molecular structure, means that the specified position is enriched with deuterium above the naturally occurring distribution of deuterium. In an embodiment, deuterium enrichment is of no less than about 1%, in another no less than about 5%, in another no less than about 10%, in another no less than about 20%, in another no less than about 50%, in another no less than about 70%, in another no less than about 80%, in another no less than about 90%, or another no less than about 98% of deuterium at the specified position.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

The terms "substantially pure" and "substantially homogeneous" mean sufficiently homogeneous to appear free of readily detectable impurities as determined by standard analytical methods, including, but not limited to, thin-layer chromatography (TLC), gel electrophoresis, high-performance liquid chromatography (HPLC), nuclear magnetic resonance (NMR), and mass spectrometry (MS); or sufficiently pure such that further purification would not detectably alter the physical and chemical properties, or biological and pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% of the molecules are a single compound, including a racemic mixture or single stereoisomer thereof, as determined by standard analytical methods.

The term "about" qualifies the numerical values that it modifies, denoting such a value as variable within a margin of error. When no margin of error, such as a standard deviation to a mean value given in a chart or table of data, is recited, the term "about" means that range which would encompass the recited value and the range which would be included by rounding up or down to that figure, considering significant figures.

The term R or the term R', appearing by itself and without a number designation, unless otherwise defined, refers to a moiety chosen from hydrogen, alkyl, cycloalkyl, heteroalkyl, aryl, heteroaryl, and heterocycloalkyl, any of which is optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g., aryl, heterocycle, R, etc.) occur more than once in a formula or generic structure, its definition at each occurrence is independent of its definition every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

The term "disease" as used herein, is intended to be generally synonymous. It is used interchangeably with the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means administering two or more therapeutic agents to treat a therapeutic condition or disorder described in the present disclosure. Such administration encompasses co-administration of these therapeutic agents in a substantially simultaneous manner, such as in a single dosage having a fixed ratio of active ingredients or in multiple, separate capsules for each active ingredient. Also, such administration encompasses the use of each type of therapeutic agent in a sequential manner. In either case, the treatment regimen will benefit the drug combination in treating the conditions or disorders described herein.

The phrase "therapeutically effective" is intended to qualify the amount of active ingredients used in treating a disease or disorder or on the effecting of a clinical endpoint.

The term "therapeutically acceptable" refers to those compounds (or salts, prodrugs, tautomers, zwitterionic forms, etc.) suitable for use in contact with the tissues of patients without undue toxicity, irritation, and allergic response, are commensurate with a reasonable benefit/risk ratio and are effective for their intended use.

As used herein, "treatment" of a patient comprises prophylaxis. Treatment may also be preemptive, i.e., it may include prevention of disease. Prevention of disease may involve complete protection from disease, for example, as in the case of prevention of infection with a pathogen or may involve prevention of disease progression. For example, the prevention of a disease may not mean complete foreclosure of any effect related to the diseases at any level. Instead, it may mean preventing the symptoms of a disease to a clinically significant or detectable level. The prevention of diseases may also mean preventing disease progression to a later stage of the disease.

The term "patient" is generally synonymous with the term "subject" and includes all mammals, including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound or parent drug. They may, for instance, be bioavailable by oral administration, whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound administered as an ester (the "prodrug") but is metabolically hydrolyzed to the carboxylic acid, the active entity. Additional examples include peptidyl derivatives of a compound.

To eliminate foreign substances, such as therapeutic agents, from its circulation system, the animal body expresses various enzymes, such as the cytochrome $P_{450}$ enzymes or CYPs, esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) π-bond. The resultant metabolites may be stable or unstable under physiological conditions and can have substantially different pharmacokinetics, pharmacodynamics, and acute and long-term toxicity profiles relative to the parent compounds. For most drugs, such oxidations are generally rapid and ultimately lead to the administration of multiple or high daily doses.

The Arrhenius equation may quantify the relationship between the activation energy and the rate of reaction, $k=Ae^{-Eact/RT}$, where $E_{act}$ is the activation energy, T is temperature, R is the molar gas constant, k is the rate constant for the reaction, and A (the frequency factor) is a constant specific to each reaction that depends on the probability that the molecules will collide with the correct orientation. The Arrhenius equation states that the fraction of molecules that have enough energy to overcome an energy barrier, that is, those with energy at least equal to the activation energy, depends exponentially on the ratio of the activation energy to thermal energy (RT), the average amount of thermal energy that molecules possess at a certain temperature.

The transition state in a reaction is short-lived (on the order of $10^{-14}$ sec) along the reaction pathway during which the original bonds have stretched to their limit. The activation energy $E_{act}$ for a reaction is the energy required to reach that reaction's transition state. Reactions that involve multiple steps will necessarily have several transition states. In these instances, the reaction's activation energy is equal to the energy difference between the reactants and the most unstable transition state. Once the transition state is reached, the molecules can revert, thus reforming the original reactants or the new bonds form, giving rise to the products. This dichotomy is possible because both pathways, forward and reverse, resulting in the release of energy. A catalyst facilitates a reaction process by lowering the activation energy leading to a transition state. Enzymes are examples of biological catalysts that reduce the energy necessary to achieve a transition state.

A carbon-hydrogen bond is, by nature, a covalent chemical bond. Such a bond forms when two atoms of similar electronegativity share some of their valence electrons, creating a force that holds the atoms together. This force or bond strength can be quantified and is expressed in units of energy. As such, covalent bonds between various atoms can be classified according to how much energy must be applied to the bond to break the bond or separate the two atoms.

The bond strength is directly proportional to the absolute value of the ground-state vibrational energy of the bond. This vibrational energy, which is also known as the zero-point vibrational energy, depends on the mass of the atoms that form the bond. The absolute value of the zero-point vibrational energy increases as the mass of one or both atoms making the bond increase. Since deuterium (D) is two-fold more massive than hydrogen (H), it follows that a C-D bond is stronger than the corresponding C—H bond. Compounds with C-D bonds are frequently indefinitely stable in $H_2O$ and have been widely used for isotopic studies. Suppose a C—H bond is broken during a rate-determining step in a chemical reaction (i.e. the step with the highest transition state energy). In that case, substituting a deuterium for that hydrogen will decrease the reaction rate, and the process will slow down. This phenomenon is known as the Deuterium Kinetic Isotope Effect (DKIE). It can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small size of a hydrogen atom and occurs because transition states involving a proton can sometimes form in the absence of the required activation energy. Deuterium is larger and statistically has a much lower probability of undergoing this phenomenon. The substitution of tritium for hydrogen results in a stronger bond than deuterium and gives numerically larger isotope effects.

Discovered in 1932 by Urey, deuterium (D) is a stable and non-radioactive isotope of hydrogen. It was the first isotope to be separated from its element in pure form and is twice as massive as hydrogen. It makes up about 0.02% of the total mass of hydrogen (in this usage, meaning all hydrogen isotopes) on earth. When two deuteriums bond with one oxygen, deuterium oxide ($D_2O$ or "heavy water") is formed. $D_2O$ looks and tastes like $H_2O$ but has different physical properties. It boils at 101.41° C. and freezes at 3.79° C. Its heat capacity, the heat of fusion, the heat of vaporization, and entropy are higher than $H_2O$. It is also more viscous and is not as powerful a solvent as $H_2O$.

When pure D₂O is given to rodents, it is readily absorbed and reaches an equilibrium level that is usually about eighty percent of the concentration of what was consumed. The quantity of deuterium required to induce toxicity is extremely high. When D₂O has replaced up to 15% of the body water, animals are healthy but cannot gain weight as fast as the control (untreated) group. When about 15% to about 20% of the body water has been replaced with D₂O, the animals become excitable. When about 20% to about 25% of the body water has been replaced with D₂O, the animals are so excitable that they go into frequent convulsions when stimulated. Skin lesions, ulcers on the paws and muzzles, and necrosis of the tails appear. The animals also become very aggressive; males were becoming almost unmanageable. When about 30% of the body water has been replaced with D₂O, the animals refuse to eat and become comatose. Their body weight drops sharply, and their metabolic rates drop far below normal, with death occurring at about 30 to about 35% replacement with D₂O. The effects are reversible unless more than thirty percent of the previous body weight has been lost due to D₂O. Studies have also shown that D₂O can delay cancer cells' growth and enhance the cytotoxicity of certain antineoplastic agents.

Tritium (T) is a radioactive isotope of hydrogen, used in research, fusion reactors, neutron generators, and radiopharmaceuticals. Mixing tritium with a phosphor provides a continuous light source, a technique that is commonly used in wristwatches, compasses, rifle sights, and exit signs. It was discovered by Rutherford, Oliphant, and Harteck in 1934 and is produced naturally in the upper atmosphere when cosmic rays react with H₂ molecules. Tritium is a hydrogen atom with 2 neutrons in the nucleus and has an atomic weight close to 3. It occurs naturally in the environment in very low concentrations, most commonly found as T₂O, a colorless and odorless liquid. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level.

Deuteration of pharmaceuticals to improve pharmacokinetics (PK), pharmacodynamics (PD), and toxicity profiles have been demonstrated previously with some drug classes. For example, DKIE was used to decrease the hepatotoxicity of halothane by presumably limiting the production of reactive species such as trifluoroacetyl chloride. However, this method may not apply to all drug classes. For example, deuterium incorporation can lead to metabolic switching, which may give rise to an oxidative intermediate with a faster off-rate from an activating Phase I enzyme (e.g., cytochrome P₄₅₀ 3A4). The concept of metabolic switching asserts that xenogens, when sequestered by Phase I enzymes, may bind transiently and re-bind in various conformations before the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart toxicity. Such pitfalls are non-obvious and have not been heretofore sufficiently predictable a priori for any drug class.

Xanomeline is a functionally selective M1/M4 agonist that has shown a promising therapeutic profile in preclinical trials (Shannon et al., 1994). The carbon-hydrogen bonds of xanomeline contain a naturally occurring distribution of hydrogen isotopes, namely ¹H or protium (about 99.9844%), ²H or deuterium (about 0.0156%), and ³H or tritium (in the range between about 0.5 and 67 tritium atoms per 10¹⁸ protium atoms). Increased levels of deuterium incorporation may produce a detectable Kinetic Isotope Effect (KIE) that could affect the pharmacokinetic, pharmacologic, and/or toxicologic profiles of such muscarinic agonists in comparison with the compound having naturally occurring levels of deuterium.

Xanomeline is likely metabolized in humans by the liver (Nicholas D et al., 2001). Other sites on the molecule may also undergo transformations leading to metabolites with as-yet-unknown pharmacology/toxicology. Limiting the production of these metabolites can decrease the danger of the administration of such drugs and may even allow increased dosage and concomitant increased efficacy. All these transformations can occur through polymorphically-expressed enzymes, thus exacerbating the interpatient variability. Further, disorders, such as multiple sclerosis, are best treated when the subject is medicated around the clock for an extended period. For the preceding reasons, there is a strong likelihood that a longer half-life medicine will diminish these problems with greater efficacy and cost savings.

Various fluorination and deuteration patterns can be used to a) reduce or eliminate unwanted metabolites, b) increase the half-life of the parent drug, c) decrease the number of doses needed to achieve the desired effect, d) decrease the amount of a dose needed to achieve the desired effect, e) increase the formation of active metabolites, if any are formed, and/or f) decrease the production of harmful metabolites in specific tissues and/or create a more effective drug and/or a safer drug for polypharmacy, whether the polypharmacy be intentional or not. The fluorination approach has strong potential to slow the metabolism via various oxidative and racemization mechanisms.

In one aspect, disclosed herein is a compound having structural Formula I:

Formula I

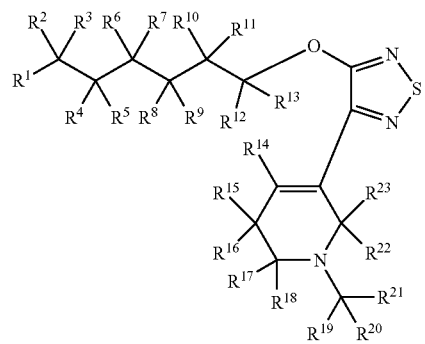

and/or salts thereof;

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ are independently chosen from H and F; and two of $R^1$, $R^2$, and $R^3$ are F, or at least one of $R^4$, $R^5$, $R^6$, $R_7$, $R^8$, $R_9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ is F.

In another aspect, disclosed herein is a compound having structural Formula I:

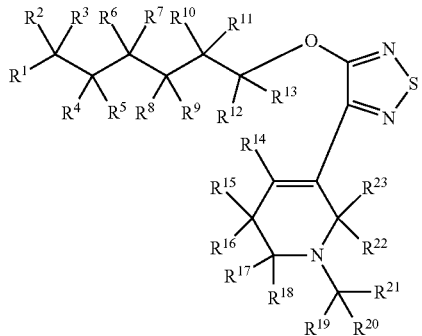

Formula I and/or salts thereof;
wherein at least one of $R^1$, $R^2$, $R^3$, $R^4$, $R^5$, $R^6$, $R^7$, $R^8$, $R^9$, $R^{10}$, $R^{11}$, $R^{12}$, and $R^{13}$ is fluorine, and the remainder are independently chosen from hydrogen and fluorine; and $R^{14}$, $R^{15}$, $R^{16}$, $R^{17}$, $R^{18}$, $R^{19}$, $R^{20}$, $R^{21}$, $R^{22}$, and $R^{23}$ are independently chosen from hydrogen and deuterium;
with the proviso that when $R^1$, $R^2$, and $R^3$ are fluorine, then at least one of $R^4$, $R^5$, $R^6$, $R^7$, $R^8$, $R^9$, $R^{10}$, $R^{11}$, $R^{12}$, and $R^{13}$ is fluorine or at least one of $R^{14}$, $R^{15}$, $R^{16}$, $R^{17}$, $R^{18}$, $R^{19}$, $R^{20}$, $R^{21}$, $R^{22}$ and $R^{23}$ is deuterium.

In certain embodiments, the compound comprises compounds of Formula II Formula II

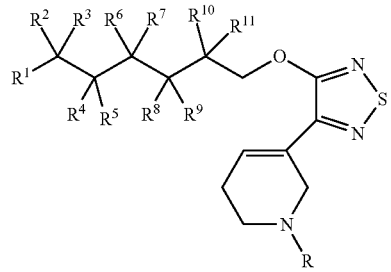

Formula II and/or salts thereof,
wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ are independently chosen from H and F; R is $CH_3$, $CH_2F$, $CHF_2$, or $CF_3$ and
and if R is $CH_3$, two of $R^1$, $R^2$, $R^3$ are F, or at least one of $R^4$, $R^5$, $R^6$, $R^7$, $R^8$, $R^9$, $R^{10}$, $R^{11}$, $R^{12}$, and $R_1$ is F.

In certain embodiments, the compound comprises compounds of Formula II

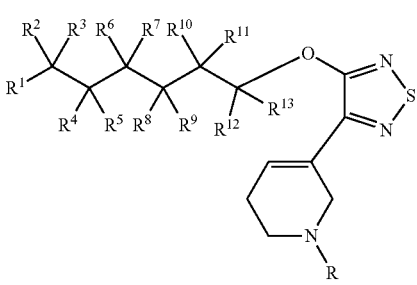

Formula II and/or salts thereof, wherein at least one of $R^1$, $R^2$, $R^3$, $R^4$, $R^5$, $R^6$, $R^7$, $R^8$, and $R^9$ is fluorine, and the remainder are independently chosen from hydrogen and fluorine; and R is $CH_3$ or $CD_3$;
with the proviso that when $R^1$, $R^2$, and $R^3$ are fluorine, then at least one of $R^4$, $R^5$, $R^6$, $R^7$, $R^8$, and $R^9$ is fluorine or R is $CD_3$.

In certain embodiments, the compound comprises a compound of Formula IIA

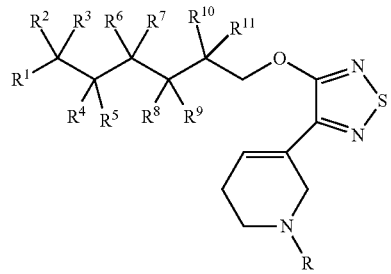

Formula IIA and/or salts thereof;
wherein $R^1$, $R^2$, $R^3$, $R^4$, $R^5$, $R^6$, $R^7$, $R^8$, $R^9$, $R^{10}$, and $R^{11}$ are independently chosen from H and F; R is $CH_3$, $CH_2F$, $CHF_2$, or $CF_3$; and if R is $CH_3$, two of $R^1$, $R^2$, and $R^3$ are F, or at least one of $R^4$, $R^5$, $R^6$, $R^7$, $R^8$, $R^9$, $R^{10}$, and $R^{11}$ is F.

In certain embodiments, the compound comprises a compound of Formula IIA

Formula IIA and/or salts thereof;
wherein at least one of $R^1$, $R^2$, $R^3$, $R^4$, $R^5$, $R^6$, $R^7$, $R^8$, $R^9$, $R_{10}$, and R is fluorine, and the remainder are independently chosen from hydrogen and fluorine; and R is $CH_3$ or $CD_3$;
with the proviso that when $R^1$, $R^2$, and $R^3$ are fluorine, then at least one of $R^4$, $R^5$, $R^6$, $R^7$, $R^8$, $R^9$, $R^{10}$, and $R^{11}$ fluorine or R is $CD_3$.

In certain embodiments, the compound comprises a compound of Formula IIB

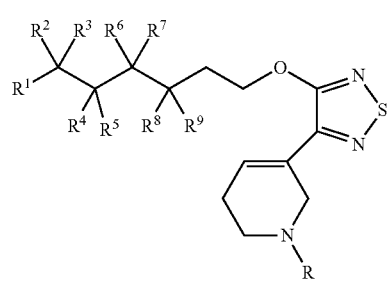

Formula IIB and/or salts thereof;
wherein $R^1$, $R^2$, $R^3$, $R^4$, $R^5$, $R^6$, $R^7$, $R^8$, and $R^9$ are independently chosen from H and F; R is $CH_3$, $CH_2F$, $CHF_2$, or $CF_3$; and if R is $CH_3$, two of $R^1$, $R^2$, and $R^3$ are F, or at least one of $R^4$, $R^5$, $R^6$, $R^7$, $R^8$, and $R^9$ is F.

In certain embodiments, the compound comprises a compound of Formula IIB

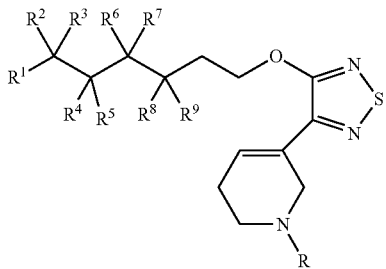

Formula IIB and/or salts thereof;
wherein at least one of $R^1$, $R^2$, $R^3$, $R^4$, $R^5$, $R^6$, $R^7$, $R^8$, and $R^9$ is fluorine, and the remainder are independently chosen from hydrogen and fluorine; and R is $CH_3$ or $CD_3$; with the proviso that when $R^1$, $R^2$, and $R^3$ are fluorine, then at least one of $R^4$, $R^5$, $R^6$, $R^7$, $R^8$, and $R^9$ is fluorine or R is $CD_3$.

In certain embodiments, the compound comprises a compound of Formula IIC

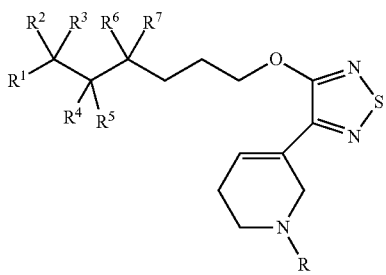

Formula IIC and/or salts thereof;
wherein $R^1$, $R^2$, $R^3$, $R^4$, $R^5$, $R^6$, and $R^7$ are independently chosen from H and F; R is $CH_3$, $CH_2F$, $CHF_2$, or $CF_3$; and if R is $CH_3$, two of $R^1$, $R^2$, and $R^3$ are F, or at least one of $R^4$, $R^5$, $R^6$, and $R^7$ is F.

In certain embodiments, the compound comprises a compound of Formula IIC

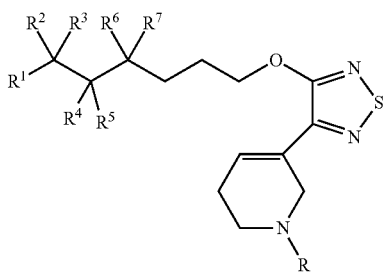

Formula IIC and/or salts thereof;
wherein at least one of $R^1$, $R^2$, $R^3$, $R^4$, $R^5$, $R^6$, and $R^7$ is fluorine, and the remainder are independently chosen from hydrogen and fluorine; and R is $CH_3$ or $CD_3$; with the proviso that when $R^1$, $R^2$, and $R^3$ are fluorine, then at least one of $R^4$, $R^5$, $R^6$, and $R^7$ is fluorine or R is $CD_3$.

In certain embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each F, and R is $CH_3$. In certain embodiments, $R^1$, $R^2$, $R^3$, $R^4$, $R^5$, $R^6$, $R^7$, $R^8$, $R^9$, $R^{10}$, $R^{11}$, $R^{12}$ and $R^{13}$ are each F, and R is $CH_2F$. In certain embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each F, and R is $CHF_2$. In certain embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each F, and R is $CF_3$.

In certain embodiments, $R^1$, $R^2$, $R^3$, $R^4$, $R^5$, $R^6$, $R^7$, $R^8$, $R^9$, $R^{10}$, and $R^{11}$, are each F, and R is $CH_3$. In certain embodiments, $R^1$, $R^2$, $R^3$, $R^4$, $R^5$, $R^6$, $R^7$, $R^8$, $R^9$, $R^{10}$, and $R^{11}$ are each F, and R is $CH_2F$. In certain embodiments, $R^1$, $R^2$, $R^3$, $R^4$, $R^5$, $R^6$, $R^7$, $R^8$, $R^9$, $R^{10}$, and $R^{11}$ are each F, and R is $CHF_2$. In certain embodiments, $R^1$, $R^2$, $R^3$, $R^4$, $R^5$, $R^6$, $R^7$, $R^8$, $R^9$, $R^{10}$, and $R^{11}$ are each F, and R is $CF_3$.

In certain embodiments, $R^1$, $R^2$, $R^3$, $R^4$, $R^5$, $R^6$, $R^7$, $R^8$, and $R^9$, are each F, and R is $CH_3$. In certain embodiments, $R^1$, $R^2$, $R^3$, $R^4$, $R^5$, $R^6$, $R^7$, $R^8$, and $R^9$ are each F, and R is $CH_2F$. In certain embodiments, $R^1$, $R^2$, $R^3$, $R^4$, $R^5$, $R^6$, $R^7$, $R^8$, and $R^9$ are each F, and R is $CHF_2$. In certain embodiments, $R^1$, $R^2$, $R^3$, $R^4$, $R^5$, $R^6$, $R^7$, $R^8$, and $R^9$ are each F, and R is $CF_3$.

In certain embodiments, $R^1$, $R^2$, $R^3$, $R^4$, $R^5$, $R^6$, and $R^7$ are each F, and R is $CH_3$. In certain embodiments, $R^1$, $R^2$, $R^3$, $R^4$, $R^5$, $R^6$, and $R^7$ are each F, and R is $CH_2F$. In certain embodiments, $R^1$, $R^2$, $R^3$, $R^4$, $R^5$, $R^6$, and $R^7$ are each F, and R is $CHF_2$. In certain embodiments, $R^1$, $R^2$, $R^3$, $R^4$, $R^5$, $R^6$, and $R^7$ are each F, and R is $CF_3$.

In certain embodiments, $R^1$, $R^2$, $R^3$, $R^4$, and $R^5$ are each F, and R is $CH_3$. In certain embodiments, $R^1$, $R^2$, $R^3$, $R^4$, and $R^5$ are each F, and R is $CH_2F$. In certain embodiments, $R^1$, $R^2$, $R^3$, $R^4$, and $R^5$ are each F, and R is $CHF_2$. In certain embodiments, $R^1$, $R^2$, $R^3$, $R^4$, and $R^5$ are each F, and R is $CF_3$.

In certain embodiments, $R^1$, $R^2$, and $R^3$ are each F, and R is $CH_3$. In certain embodiments, $R^1$, $R^2$, and $R^3$ are each F, and R is $CH_2F$. In certain embodiments, $R^1$, $R^2$, and $R^3$ are each F, and R is $CHF_2$. In certain embodiments, $R^1$, $R^2$, and $R^3$ are each F, and R is $CF_3$.

In certain embodiments, $R^4$, $R^5$, $R^6$, $R^7$, $R^8$, $R^9$, $R^{10}$, $R^{11}$, $R^{12}$, and $R^{13}$ are each F, and R is $CH_3$. In certain embodiments, $R^4$, $R^5$, $R^6$, $R^7$, $R^8$, $R^9$, $R^{10}$, $R^{11}$, $R^{12}$, and $R^{13}$ are each F, and R is $CH_2F$. In certain embodiments, $R^4$, $R^5$, $R^6$, $R^7$, $R^8$, $R^9$, $R^{10}$, $R^{11}$, $R^{12}$, and $R^{13}$ are each F, and R is $CHF_2$. In certain embodiments, $R^4$, $R^5$, $R^6$, $R^7$, $R^8$, $R^9$, $R^{10}$, $R^{11}$, $R^{12}$, and $R^{13}$ are each F, and R is $CF_3$.

In certain embodiments, $R^6$, $R^7$, $R^8$, $R^9$, $R^{10}$, $R^{11}$, $R^{12}$, and $R^{13}$ are each F, and R is $CH_3$. In certain embodiments, $R^6$, $R^7$, $R^8$, $R^9$, $R^{10}$, $R^{11}$, $R^{12}$, and $R^{13}$ are each F, and R is $CH_2F$. In certain embodiments, $R^6$, $R^7$, $R^8$, $R^9$, $R^{10}$, $R^{11}$, $R^{12}$, and $R^{13}$ are each F, and R is $CHF_2$. In certain embodiments, $R^6$, $R^7$, $R^8$, $R^9$, $R^{10}$, $R^{11}$, $R^{12}$, and $R^{13}$ are each F, and R is $CF_3$.

In certain embodiments, $R^8$, $R^9$, $R^{10}$, $R^{11}$, $R^{12}$, and $R^{13}$ are each F, and R is $CH_3$. In certain embodiments, $R^8$, $R^9$, $R^{10}$, $R^{11}$, $R^{12}$, and $R^{13}$ are each F, and R is $CH_2F$. In certain embodiments, $R^8$, $R^9$, $R^{10}$, $R^{11}$, $R^{12}$, and $R^{13}$ are each F, and R is $CHF_2$. In certain embodiments, $R^8$, $R^9$, $R^{10}$, $R^{11}$, $R^{12}$, and $R^{13}$ are each F, and R is $CF_3$.

In certain embodiments, $R^{10}$, $R^{11}$, $R^{12}$, and $R^{13}$ are each F, and R is $CH_3$. In certain embodiments, $R^{10}$, $R^{11}$, $R^{12}$, and $R^{13}$ are each F, and R is $CH_2F$. In certain embodiments, $R^{10}$, $R^{11}$, $R^{12}$, and $R^{13}$ are each F, and R is $CHF_2$. In certain embodiments, $R^{10}$, $R^{11}$, $R^{12}$, and $R^{13}$ are each F, and R is $CF_3$.

In certain embodiments, $R^{12}$ and $R^{13}$ are each F, and R is $CH_3$. In certain embodiments, $R^{12}$ and $R^{13}$ are each F, and R is $CH_2F$. In certain embodiments, $R^{12}$ and $R^{13}$ are each F, and R is $CHF_2$. In certain embodiments, $R^{12}$ and $R^{13}$ are each F, and R is $CF_3$.

In certain embodiments, $R_4$ and $R^5$ are each F, and R is $CH_3$. In certain embodiments, $R^4$ and $R^5$ are each F, and R is $CH_2F$. In certain embodiments, $R^4$ and $R^5$ are each F, and R is $CHF_2$. In certain embodiments, $R^4$ and $R^5$ are each F, and R is $CF_3$.

In certain embodiments, $R^6$ and $R^7$ are each F, and R is $CH_3$. In certain embodiments, $R^6$ and $R^7$ are each F, and R is $CH_2F$. In certain embodiments, $R^6$ and $R^7$ are each F, and R is $CHF_2$. In certain embodiments, $R^6$ and $R^7$ are each F, and R is $CF_3$.

In certain embodiments, $R^8$ and $R^9$ are each F, and R is $CH_3$. In certain embodiments, $R^8$ and $R^9$ are each F, and R is $CH_2F$. In certain embodiments, $R^8$ and $R^9$ are each F, and R is $CHF_2$. In certain embodiments, $R^8$ and $R^9$ are each F, and R is $CF_3$.

In certain embodiments, $R^{10}$ and $R^{11}$ are each F, and R is $CH_3$. In certain embodiments, $R^{10}$ and $R^{11}$ are each F, and R is $CH_2F$. In certain embodiments, $R^{10}$ and $R^{11}$ are each F, and R is $CHF_2$. In certain embodiments, $R^{10}$ and $R^{11}$ are each F, and R is $CF_3$.

In certain embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each F, and R is $CH_2D$. In certain embodiments, $R^1$, $R^2$, $R^3$, $R^4$, $R^5$, $R^6$, $R^7$, $R^8$, $R^9$, $R^{10}$, $R^{11}$, $R^{12}$ and $R^{13}$ are each F, and R is $CHD_2$. In certain embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each F, and R is $CD_3$.

In certain embodiments, $R^1$, $R^2$, $R^3$, $R^4$, $R^5$, $R^6$, $R^7$, $R^8$, $R^9$, $R^{10}$, and $R^{11}$ are each F, and R is $CH_2D$. In certain embodiments, $R^1$, $R^2$, $R^3$, $R^4$, $R^5$, $R^6$, $R^7$, $R^8$, $R^9$, $R^{10}$, and $R^{11}$ are each F, and R is $CHD_2$. In certain embodiments, $R^1$, $R^2$, $R^3$, $R^4$, $R^5$, $R^6$, $R^7$, $R^8$, $R^9$, $R^{10}$, and $R^{11}$ are each F, and R is $CD_3$.

In certain embodiments, $R^1$, $R^2$, $R^3$, $R^4$, $R^5$, $R^6$, $R^7$, $R^8$, and $R^9$ are each F, and R is $CH_2D$. In certain embodiments, $R^1$, $R^2$, $R^3$, $R^4$, $R^5$, $R^6$, $R^7$, $R^8$, and $R^9$ are each F, and R is $CHD_2$. In certain embodiments, $R^1$, $R^2$, $R^3$, $R^4$, $R^5$, $R^6$, $R^7$, $R^8$, and $R^9$ are each F, and R is $CD_3$.

In certain embodiments, $R^1$, $R^2$, $R^3$, $R^4$, $R^5$, $R^6$, and $R^7$ are each F, and R is $CH_2D$. In certain embodiments, $R^1$, $R^2$, $R^3$, $R^4$, $R^5$, $R^6$, and $R^7$ are each F, and R is $CHD_2$. In certain embodiments, $R^1$, $R^2$, $R^3$, $R^4$, $R^5$, $R^6$, and $R^7$ are each F, and R is $CD_3$.

In certain embodiments, $R^1$, $R^2$, $R^3$, $R^4$, and $R^5$ are each F, and R is $CD_3$. In certain embodiments, $R^1$, $R^2$, $R^3$, $R^4$, and $R^5$ are each F, and R is $CH_2D$. In certain embodiments, $R^1$, $R^2$, $R^3$, $R^4$, and $R^5$ are each F, and R is $CHD_2$. In certain embodiments, $R^1$, $R^2$, $R^3$, $R^4$, and $R^5$ are each F, and R is $CD_3$.

In certain embodiments, $R^1$, $R^2$, and $R^3$ are each F, and R is $CH_2D$. In certain embodiments, $R^1$, $R^2$, and $R^3$ are each F, and R is $CHD_2$. In certain embodiments, $R^1$, $R^2$, and $R^3$ are each F, and R is $CD_3$.

In certain embodiments, $R^4$, $R^5$, $R^6$, $R^7$, $R^8$, $R^9$, $R^{10}$, $R^{11}$, $R^{12}$, and $R^{13}$ are each F, and R is $CH_2D$. In certain embodiments, $R^4$, $R^5$, $R^6$, $R^7$, $R^8$, $R^9$, $R^{10}$, $R^{11}$, $R^{12}$, and $R^{13}$ are each F, and R is $CHD_2$. In certain embodiments, $R^4$, $R^5$, $R^6$, $R^7$, $R^8$, $R^9$, $R^{10}$, $R^{11}$, $R^{12}$, and $R^{13}$ are each F, and R is $CD_3$.

In certain embodiments, $R^6$, $R^7$, $R^8$, $R^9$, $R^{10}$, $R^{11}$, $R^{12}$, and $R^{13}$ are each F, and R is $CH_2D$. In certain embodiments, $R^6$, $R^7$, $R^8$, $R^9$, $R^{10}$, $R^{11}$, $R^{12}$, and $R^{13}$ are each F, and R is $CHD_2$. In certain embodiments, $R^6$, $R^7$, $R^8$, $R^9$, $R^{10}$, $R^{11}$, $R^{12}$, and $R^{13}$ are each F, and R is $CD_3$.

In certain embodiments, $R^8$, $R^9$, $R^{10}$, $R^{11}$, $R^{12}$, and $R^{13}$ are each F, and R is $CH_2D$. In certain embodiments, $R^8$, $R^9$, $R^{10}$, $R^{11}$, $R^{12}$, and $R^{13}$ are each F, and R is $CHD_2$. In certain embodiments, $R^8$, $R^9$, $R^{10}$, $R^{11}$, $R^{12}$, and $R^{13}$ are each F, and R is $CD_3$.

In certain embodiments, $R^{10}$, $R^{11}$, $R^{12}$, and $R^{13}$ are each F, and R is $CH_2D$. In certain embodiments, $R^{10}$, $R^{11}$, $R^{12}$, and $R^{13}$ are each F, and R is $CHD_2$. In certain embodiments, $R^{10}$, $R^{11}$, $R^{12}$, and $R^{13}$ are each F, and R is $CD_3$.

In certain embodiments, $R^{12}$ and $R^{13}$ are each F, and R is $CH_2D$. In certain embodiments, $R^{12}$ and $R^{13}$ are each F, and R is $CHD_2$. In certain embodiments, $R^{12}$ and $R^{13}$ are each F, and R is $CD_3$.

In certain embodiments, $R^4$ and $R^5$ are each F, and R is $CH_2D$. In certain embodiments, $R^4$ and $R^5$ are each F, and R is $CHD_2$. In certain embodiments, $R^4$ and $R^5$ are each F, and R is $CD_3$.

In certain embodiments, $R^6$ and $R^7$ are each F, and R is $CH_2D$. In certain embodiments, $R^6$ and $R^7$ are each F, and R is $CHD_2$. In certain embodiments, $R^6$ and $R^7$ are each F, and R is $CD_3$.

In certain embodiments, $R^8$ and $R^9$ are each F, and R is $CH_2D$. In certain embodiments, $R^8$ and $R^9$ are each F, and R is $CHD_2$. In certain embodiments, $R^8$ and $R^9$ are each F, and R is $CD_3$.

In certain embodiments, $R^{10}$ and $R^{11}$ are each F, and R is $CH_2D$. In certain embodiments, $R^{10}$ and $R^{11}$ are each F, and R is $CHD_2$. In certain embodiments, $R^{10}$ and $R^{11}$ are each F, and R is $CD_3$.

The present disclosure also provides a method of treating a central nervous system disorder in a patient in need thereof. The method comprising administrating therapeutically effective amount of a medicament described herein to the patient in need thereof. In certain embodiments, the medicament comprises a compound of Formula I as described herein and a pharmaceutically acceptable carrier In certain embodiments, the medicament is orally administered. In certain embodiments, the use of the trospium chloride, when present, alleviates a side effect associated with the use of a compound described herein.

In another embodiment, at least one of the positions represented as D independently has deuterium enrichment of no less than about 1%, no less than about 5%, no less than about 10%, no less than about 20%, no less than about 50%, no less than about 70%, no less than about 80%, no less than about 90%, or no less than about 98%.

In a further embodiment, said compound is substantially a single enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, substantially an individual diastereomer, or a mixture of about 90% or more by weight of an individual diastereomer and about 10% or less by weight of any other diastereomer.

In certain embodiments, the compound as disclosed herein contains about 60% or more by weight of the (−)-enantiomer of the compound and about 40% or less by weight of (+)-enantiomer of the compound. In certain embodiments, the compound as disclosed herein contains about 70% or more by weight of the (−)-enantiomer of the compound and about 30% or less by weight of (+)-enantiomer of the compound. In certain embodiments, the compound as disclosed herein contains about 80% or more by weight of the (−)-enantiomer of the compound and about 20% or less by weight of (+)-enantiomer of the compound. In certain embodiments, the compound as disclosed herein contains about 90% or more by weight of the (−)-enantiomer of the compound and about 10% or less by weight of the (+)-enantiomer of the compound. In certain embodiments, the compound as disclosed herein contains about 95% or more by weight of the (−)-enantiomer of the compound and about 5% or less by weight of (+)-enantiomer of the compound. In certain embodiments, the compound as disclosed herein contains about 99% or more by weight of the (−)-enantiomer of the compound and about 1% or less by weight of (+)-enantiomer of the compound.

In certain embodiments, the compound as disclosed herein contains about 60% or more by weight of the (+)-enantiomer of the compound and about 40% or less by weight of (−)-enantiomer of the compound. In certain embodiments, the compound as disclosed herein contains about 70% or more by weight of the (+)-enantiomer of the compound and about 30% or less by weight of (−)-enantiomer of the compound. In certain embodiments, the compound as disclosed herein contains about 80% or more by weight of the (+)-enantiomer of the compound and about 20% or less by weight of (−)-enantiomer of the compound. In certain embodiments, the compound as disclosed herein contains about 90% or more by weight of the (+)-enantiomer of the compound and about 10% or less by weight of the (−)-enantiomer of the compound. In certain embodiments, the compound as disclosed herein contains about 95% or more by weight of the (+)-enantiomer of the compound and about 5% or less by weight of (−)-enantiomer of the compound. In certain embodiments, the compound as disclosed herein contains about 99% or more by weight of the (+)-enantiomer of the compound and about 1% or less by weight of (−)-enantiomer of the compound.

In one embodiment, the compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

In one embodiment, the deuterated compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

Isotopic hydrogen can be introduced into a compound of a compound disclosed herein as disclosed herein by synthetic techniques that employ deuterated reagents, whereby incorporation rates are pre-determined; and/or by exchange techniques, wherein incorporation rates are determined by equilibrium conditions and may be highly variable depending on the reaction conditions. Synthetic techniques, where tritium or deuterium is directly and specifically inserted by tritiated or deuterated reagents of known isotopic content, may yield high tritium or deuterium abundance but can be limited by the chemistry required. Also, the molecule is labeled may be changed, depending upon the severity of the synthetic reaction employed. On the other hand, exchange techniques may yield lower tritium or deuterium incorporation, often with the isotope being distributed over many sites on the molecule, but offer the advantage that they do not require separate synthetic steps and are less likely to disrupt the structure of the molecule being labeled. Isotopic hydrogen can be introduced into organic molecules by synthetic techniques that employ deuterated reagents whereby incorporation rates are pre-determined and/or by exchange techniques. Incorporation rates are determined by equilibrium conditions and may be highly variable depending on the reaction conditions. Synthetic techniques, where tritium or deuterium is directly and specifically inserted by tritiated or deuterated reagents of known isotopic content, may yield high tritium or deuterium abundance but can be limited by the chemistry required. The molecule being labeled may also be changed, depending upon the severity of the synthetic reaction employed.

It is to be understood that the compounds disclosed herein may contain one or more chiral centers, chiral axes, and/or chiral planes, as described in "Stereochemistry of Carbon Compounds" Eliel and Wilen, John Wiley & Sons, New York, 1994, pp. 1119-1190. Such chiral centers, chiral axes, and chiral planes may be either the (R) or (S) configuration or a mixture.

Another method for characterizing a composition containing a compound having at least one chiral center is the composition's effect on a beam of polarized light. When a beam of plane-polarized light is passed through a chiral compound solution, the plane of polarization of the light that emerges is rotated relative to the original plane. This phenomenon is known as optical activity, and compounds that rotate the plane of polarized light are said to be optically active. One enantiomer of a compound will rotate the beam of polarized light in one direction, and the other enantiomer will rotate the beam of light in the opposite direction. The enantiomer that rotates the polarized light in the clockwise direction is the (+) enantiomer, and the enantiomer that rotates the polarized light in the counterclockwise direction is the (−) enantiomer. Included within the scope of the compositions described herein are compositions containing between 0 and 100% of the (+) and/or (−) enantiomer of compounds disclosed herein.

A compound, as disclosed herein, contains an alkenyl or alkenylene group. The compound may exist as one or a mixture of geometric cis/trans (or Z/E) isomers. Where structural isomers are interconvertible via a low energy barrier, the compound disclosed herein may exist as a single tautomer or a mixture of tautomers. This can take the form of proton tautomerism in the compound disclosed herein that contains, for example, an imino, keto, or oxime group; or so-called valence tautomerism in the compound that contain an aromatic moiety. It follows that a single compound may exhibit more than one type of isomerism.

The compounds disclosed herein may be enantiomerically pure, such as a single enantiomer or a single diastereomer, or be stereoisomeric mixtures, such as a mixture of enantiomers, a racemic mixture, or a diastereomeric mixture. One of skill in the art will recognize that administering a compound in its (R) form is equivalent, for compounds that undergo epimerization in vivo, to the administration of the compound in its (S) form. Conventional techniques for the preparation/isolation of individual enantiomers include chiral synthesis from a suitable optically pure precursor or the resolution of the racemate using, for example, chiral chromatography, recrystallization, resolution, diastereomeric salt formation, or derivatization into diastereomeric adducts followed by separation.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in preparing and purifying the compound in question. Basic addition salts may also be formed and be pharmaceutically acceptable.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids that can be employed to form therapeutically acceptable addition salts include inorganic acids such as hydrochloric, hydrobromic, sulfuric, phosphoric, and organic acids such as oxalic, maleic, succinic, and citric. Salts can also be formed by coordinating the compounds with an alkali metal or alkaline earth ion. Hence, the present disclosure contemplates sodium, potassium, magnesium, and calcium salts of the compounds disclosed herein and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for forming base addition salts include ethylenediamine, ethanolamine, diethanolamine, piperidine, and piperazine.

A salt of a compound can be made by reacting the appropriate compound in the form of the free base with the appropriate acid.

As disclosed herein, the compound may also be designed as a prodrug, which is a functional derivative of the compound and is readily convertible into the parent compound in vivo. Prodrugs are often useful because, in some situations, they may be easier to administer than the parent compound. They may, for instance, be bioavailable by oral administration, whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

While the disclosed compounds may be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and understood in the art. The pharmaceutical compositions disclosed herein may be manufactured in any manner known in the art, e.g., through conventional mixing, dissolving, granulating, dragee-making, levigating, emulsifying, encapsulating, entrapping, or compression processes.

The formulations include those suitable for oral, parenteral (including subcutaneous, intradermal, intramuscular, intravenous, intraarticular, and intramedullary), intraperitoneal, transmucosal, transdermal, rectal, and topical (including dermal, buccal, sublingual, and intraocular) administration. However, the most suitable route may depend upon the condition and disorder of the recipient. The formulations may conveniently be presented in unit dosage form and may be prepared by any of the methods well known in the art of pharmacy. Typically, these methods include bringing into association a compound disclosed herein or a pharmaceutically acceptable salt, ester, amide, prodrug, or solvate thereof ("active ingredient") with the carrier constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets, or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

Pharmaceutical preparations can be used orally include tablets, push-fit capsules made of gelatin, and soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active, or dispersing agents. Molded tablets may be made by molding a mixture of the powdered compound moistened with an inert liquid diluent in a suitable machine. The tablets may optionally be coated or scored and may be formulated to provide slow or controlled release of the active ingredient therein. All formulations for oral administration should be in dosages suitable for such administration. The push-fit capsules can contain the active ingredients in the admixture with filler such as lactose, binders such as starches, and/or lubricants such as talc or magnesium stearate, optionally, stabilizers. In soft capsules, the active compounds may be dissolved or suspended in suitable liquids, such as fatty oils, liquid paraffin, or liquid polyethylene glycols. Also, stabilizers may be added. Dragee cores are provided with suitable coatings. For this purpose, concentrated sugar solutions may be used, which may optionally contain gum arabic, talc, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings to identify or characterize different combinations of active compound doses.

In certain embodiments, a single dosage form contains 50 mg xanomeline as the tartrate salt and 10 mg trospium chloride. Because 50 mg xanomeline as a free base corresponds to about 76 mg xanomeline tartrate, the ratio of the active ingredients in such a formulation is about 7.6 to 1.

The compounds may be formulated for parenteral administration by injection, e.g., by bolus injection or continuous infusion. Formulations for injection may be presented in unit dosage form, e.g., in ampoules or multi-dose containers, with an added preservative. The compositions may take such forms as suspensions, solutions, or emulsions in oily or aqueous vehicles and may contain formulatory agents such as suspending, stabilizing, and/or dispersing agents. The formulations may be presented in unit-dose or multi-dose containers, for example, sealed ampoules and vials. They may be stored in powder form or in a freeze-dried (lyophilized) condition requiring only the addition of the sterile liquid carrier, for example, saline or sterile pyrogen-free water, immediately before use. Extemporaneous injection solutions and suspensions may be prepared from sterile powders, granules, and tablets of the kind previously described.

Formulations for parenteral administration include aqueous and non-aqueous (oily) sterile injection solutions of the active compounds which may contain antioxidants, buffers, bacteriostats, and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances that increase the suspension's viscosity, such as sodium carboxymethyl cellulose, sorbitol, or dextran. Optionally, the suspension may also contain suitable stabilizers or agents that increase the compounds' solubility to prepare highly concentrated solutions.

In addition to the formulations described previously, the compounds may also be formulated as a depot preparation. Such long-acting formulations may be administered by implantation (for example, subcutaneously or intramuscularly) or intramuscular injection. For example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may be tablets, lozenges, pastilles, or gels formulated conventionally. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is, by non-systemic administration. This includes applying a compound disclosed herein externally to the epidermis or the buccal cavity and the instillation of such a compound into the ear, eye, and nose, such that the compound does not significantly enter the bloodstream. In contrast, systemic administration refers to oral, intravenous, intraperitoneal, and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear, or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs, or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In a pressurized aerosol, the dosage unit may be determined by providing a valve to deliver a metered amount. Alternatively, for administration by inhalation or insufflation, the compounds may be a dry powder composition, for example, a powder mix of the compound and a suitable powder base such as lactose or starch. The powder composition may be presented in unit dosage forms, such as capsules, cartridges, gelatin, or blister packs. The powder may be administered with the aid of an inhalator or insufflator.

Preferred unit dosage formulations contain an effective dose, as herein below recited, or an appropriate fraction thereof, of the active ingredient.

In addition to the ingredients mentioned above, the formulations described above may include other agents conventional in the art regarding the type of formulation in question. For example, those suitable for oral administration may include flavoring agents.

Before administering the disclosed combinations, patients may have a lead-in period from one to fourteen days, during which lead-in period trospium chloride is given alone. In one embodiment, the trospium chloride is administered for one or more dose periods before administering xanomeline to accumulate trospium chloride in the body or for the trospium chloride to reach or approach steady-state exposure levels. This accumulation, or higher exposure levels of the trospium chloride, increases the blockade of muscarinic receptors outside of the brain and reduces adverse events when xanomeline is administered. In another embodiment, the trospium chloride is administered for one or more days before xanomeline Various time and resource-intensive methods demonstrated the efficacy of the combination of xanomeline and trospium chloride. For example, animal models demonstrate the efficacy of new therapeutics for schizophrenia, including pharmacological models (e.g., ketamine model) and genetic models (e.g., DISC1 mouse). Likewise, animal models, including rodents, dogs, and non-human primates, demonstrate the side effect profile of pharmacological agents. Animal models are an experimental proxy for humans but may suffer from deficiencies in the physiological differences between humans and animals and may have limited predictive power for human experiments, particularly for central nervous system disorders. Alternatively, the disclosed combination can be tried in controlled clinical trials of people. Standard measures based on patient self-report can be used by those skilled in the art to assess various side effects such as GI discomfort. As another example, objective physiological measures (e.g., EKGs) may be used by those skilled in the art. A set of standard measures has also been developed to assess schizophrenia symptoms, including the Brief Psychiatric Rating Scale (BPRS), the Positive and Negative Syndrome Scale (PANSS), and Clinical Global Impression (CGI). Typically, clinical trials are double-blinded, where one group of patients receives an inactive placebo, and the other group the active intervention.

The present disclosure also provides a medicament comprising a compound described herein and/or a salt thereof and a pharmaceutically acceptable carrier. In certain embodiments, the medicament comprises between 5 mg and 300 mg of the compound, such as between 5 mg and 10 mg, between 10 mg and 15 mg, between 15 mg and 20 mg, between 20 mg and 25 mg, between 25 mg and 30 mg, between 30 mg and 35 mg, between 35 mg and 40 mg, between 40 mg and 45 mg, between 45 mg and 50 mg, between 50 mg and 55 mg, between 55 mg and 60 mg, between 60 mg and 65 mg, between 65 mg and 70 mg, between 70 mg and 75 mg, between 75 mg and 80 mg, between 80 mg and 85 mg, between 85 mg and 90 mg, between 90 mg and 95 mg, between 95 mg and 100 mg, between 100 mg and 105 mg, between 105 mg and 110 mg, between 110 mg and 115 mg, between 115 mg and 120 mg, between 120 mg and 125 mg, between 125 mg and 130 mg, between 130 mg and 135 mg, between 135 mg and 140 mg, between 140 mg and 145 mg, between 145 mg and 150 mg, between 150 mg and 155 mg, between 155 mg and 160 mg, between 160 mg and 165 mg, between 165 mg and 170 mg, between 170 mg and 175 mg, between 175 mg and 180 mg, between 180 mg and 185 mg, between 185 mg and 190 mg, between 190 mg and 195 mg, between 195 mg and 200 mg, between 200 mg and 205 mg, between 205 mg and 210 mg, between 210 mg and 215 mg, between 215 mg and 220 mg, between 220 mg and 225 mg, between 225 mg and 230 mg, between 230 mg and 235 mg, between 235 mg and 240 mg, between 240 mg and 245 mg, between 245 mg and 250 mg, between 250 mg and 255 mg, between 255 mg and 260 mg, between 260 mg and 265 mg, between 265 mg and 270 mg, between 270 mg and 275 mg, between 275 mg and 280 mg, between 280 mg and 285 mg, between 285 mg and 290 mg, between 290 mg and 295 mg, or between 295 mg and 300 mg of a compound of Formula I.

In certain embodiments, the medicament further comprises a muscarinic inhibitor. In certain embodiments, the muscarinic inhibitor is trospium chloride. In certain embodiments, the medicament comprises between 5 mg and 150 mg of trospium chloride, such as between 5 mg and 10 mg, between 10 mg and 15 mg, between 15 mg and 20 mg, between 20 mg and 25 mg, between 25 mg and 30 mg, between 30 mg and 35 mg, between 35 mg and 40 mg, between 40 mg and 45 mg, between 45 mg and 50 mg, between 50 mg and 55 mg, between 55 mg and 60 mg, between 60 mg and 65 mg, between 65 mg and 70 mg, between 70 mg and 75 mg, between 75 mg and 80 mg, between 80 mg and 85 mg, between 85 mg and 90 mg, between 90 mg and 95 mg, between 95 mg and 100 mg, between 100 mg and 105 mg, between 105 mg and 110 mg, between 110 mg and 115 mg, between 115 mg and 120 mg, between 120 mg and 125 mg, between 125 mg and 130 mg, between 130 mg and 135 mg, between 135 mg and 140 mg, between 140 mg and 145 mg, or between 145 mg and 150 mg of trospium chloride.

In certain embodiments, the medicament is formulated as an immediate-release formulation. In certain embodiments, the medicament is formulated as a controlled release formulation. In certain embodiments, the medicament is formulated as a controlled release formulation, and the trospium chloride is formulated as an immediate-release formulation.

In certain embodiments, the medicament comprises between 50 mg and 150 mg of the compound and between 10 mg and 40 mg trospium chloride in a single dosage form. In certain embodiments, the medicament comprises 50 milligrams of the compound. In certain embodiments, the medicament comprises 75 milligrams of the compound. In certain embodiments, the medicament comprises 10 milligrams trospium chloride. In certain embodiments, the medicament comprises 20 milligrams trospium chloride. In certain embodiments, the medicament is in the form of a single dosage formulation consisting essentially of 50 milligrams of the compound, 10 milligrams trospium chloride, and a pharmaceutically acceptable carrier.

In certain embodiments, the medicament comprises between 5 mg and 50 mg of the composition and between 10 mg and 40 mg trospium chloride in a single dosage form. In certain embodiments, the medicament comprises 50 milligrams of the composition. In certain embodiments, the medicament comprises 75 milligrams of the composition. In certain embodiments, the medicament comprises 10 milligrams trospium chloride. In certain embodiments, the medicament comprises 20 milligrams trospium chloride. In certain embodiments, the medicament is in the form of a single dosage formulation consisting essentially of 50 milligrams of the composition, 10 milligrams trospium chloride, and a pharmaceutically acceptable carrier.

In certain embodiments, the medicament is in the form of a single dosage formulation consisting essentially of between 5 and 75 milligrams of a compound of Formula I, 20 milligrams trospium chloride, and a pharmaceutically acceptable carrier. In certain embodiments, the medicament is in the form of a single dosage formulation consisting essentially of 50 milligrams of a compound of Formula I, 20 milligrams trospium chloride, and a pharmaceutically acceptable carrier. In certain embodiments, the medicament is in the form of a single dosage formulation consisting essentially of between 5 and 75 milligrams of a compound of Formula I, 10 milligrams trospium chloride, and a pharmaceutically acceptable carrier. In certain embodiments, the pharmaceutically acceptable carrier comprises cellulose and lactose.

Before administering the disclosed combinations, patients may have a lead-in period from one to fourteen days, during which lead-in period trospium chloride is given alone. In one embodiment, the trospium chloride is administered for one or more dose periods before administering the compound to accumulate trospium chloride in the body or the trospium chloride to reach or approach steady-state exposure levels. This accumulation, or higher exposure levels of the trospium chloride, increases the blockade of muscarinic receptors outside of the brain and reduces adverse events when the compound is administered. In another embodiment, the trospium chloride is administered for one or more days before the compound.

In one embodiment, the compound and trospium chloride are administered to a patient 6 times during a 24-hour period. In another embodiment, compound and trospium chloride are administered to a patient 5 times during a 24-hour period. In another embodiment, compound and trospium chloride are administered to a patient 4 times during a 24-hour period. In an embodiment, compound and trospium chloride are administered to a patient 3 times during a 24-hour period. In another embodiment, compound and trospium chloride are administered to a patient twice during a 24-hour period. In another embodiment, compound and trospium chloride are administered to a patient once a 24-hour period.

In one embodiment, an extended-release formulation of trospium chloride is used in combination with the compound. In another embodiment, trospium chloride extended-release is administered to a patient from one time to five times during a 24-hour period. In an embodiment, trospium chloride extended-release is administered from one to three times during a 24-hour period. In another embodiment, from five milligrams to 400 milligrams of trospium chloride, extended-release is used during a 24-hour period. In an embodiment, from 20 milligrams to 200 milligrams of trospium chloride, extended-release is used during a 24-hour period.

In one embodiment, 225 mg compound and 40 mg trospium chloride are administered to a patient in a 24-hour period. In another embodiment, 5 mg compound and 20 mg trospium chloride are administered to a patient in a 24-hour period. In another embodiment, 10 mg compound and 20 mg trospium chloride are administered to a patient in a 24-hour period. In another embodiment, 20 mg compound and 20 mg trospium chloride are administered to a patient in a 24-hour period. In another embodiment, 40 mg compound and 20 mg trospium chloride are administered to a patient in a 24-hour period. In another embodiment, 80 mg compound and 20 mg trospium chloride are administered to a patient in a 24-hour period. In another embodiment, 100 mg compound and 20 mg trospium chloride are administered to a patient in a 24-hour period. In another embodiment, 125 mg compound and 20 mg trospium chloride are administered to a patient in a 24-hour period. In another embodiment, 125 mg compound and 30 mg trospium chloride are administered to a patient in a 24-hour period. In another embodiment, 125 mg compound and 40 mg trospium chloride are administered to a patient in a 24-hour period. In another embodiment, 200 mg compound and 40 mg trospium chloride are administered to a patient in a 24-hour period. In another embodiment, 200 mg compound and 80 mg trospium chloride are administered to a patient in a 24-hour period. In another embodiment, 250 mg compound and 60 mg trospium chloride are administered to a patient in a 24-hour period. In another embodiment, 250 mg compound and 80 mg trospium chloride are administered to a patient in a 24-hour period. In another embodiment, 300 mg compound and 40 mg trospium chloride are administered to a patient in a 24-hour period. In another embodiment, 300 mg compound and 80 mg trospium chloride are administered to a patient in a 24-hour period. In another embodiment, 300 mg compound and 120 mg trospium chloride are administered to a patient in a 24-hour period. In another embodiment, 300 mg compound and 150 mg trospium chloride are administered to a patient in a 24-hour period.

Treatment may be initiated with smaller dosages. After that, the dosage may be increased by small increments until a balance between therapeutic effect and side effects is attained. While the subject is being treated, the patient's health may be monitored by measuring one or more of the relevant indices at predetermined times during the treatment period. Treatment, including compound, amounts, administration, and formulation times, may be adjusted per such monitoring. The patient may be periodically reevaluated to determine improvement by measuring the same parameters. Adjustments to the disclosed compound administered and possibly to the administration time may be made based on these reevaluations.

In certain embodiments, the single dosage form has a dosage strength of 50 mg compound free base and 20 mg trospium chloride. In certain embodiments, the single dosage form has a dosage strength of 50 mg compound free base and 10 mg trospium chloride. In certain embodiments, the single dosage form has a dosage strength of 75 mg compound free base and 20 mg trospium chloride. In certain embodiments, the single dosage form has a dosage strength of 75 mg compound free base and 10 mg trospium chloride. In certain embodiments, the single dosage form has a dosage strength of 125 mg compound free base and 30 mg trospium chloride. In certain embodiments, the single dosage form has a dosage strength of 125 mg compound free base and 40 mg trospium chloride.

In certain embodiments, the single dosage form has a dosage strength of 10 mg compound and 30 mg trospium chloride. In certain embodiments, the single dosage form has a dosage strength of 10 mg compound and 60 mg trospium chloride. In certain embodiments, the single dosage form has a dosage strength of 25 mg compound and 30 mg trospium chloride. In certain embodiments, the single dosage form has a dosage strength of 25 mg compound and 60 mg trospium chloride. In certain embodiments, the single dosage form has a dosage strength of 50 mg compound and 30 mg trospium chloride. In certain embodiments, the single dosage form has a dosage strength of 50 mg compound and 60 mg trospium chloride. In certain embodiments, the single dosage form has a dosage strength of 100 mg compound and 30 mg trospium chloride. In certain embodiments, the single dosage form has a dosage strength of 100 mg compound and 60 mg trospium chloride. In certain embodiments, the single dosage form has a dosage strength of 125 mg compound and 30 mg trospium chloride. In certain embodiments, the single dosage form has a dosage strength of 125 mg compound and 60 mg trospium chloride. The amount of active ingredient that may be combined with the carrier materials to produce a single dosage form will vary depending upon the host treated and the mode of administration.

The compounds can be administered in various modes, e.g., orally, topically, or by injection. The precise amount of compound administered to a patient will be the responsibility of the attendant physician. The specific dose level for any patient depends upon a variety of factors, including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself, the adjuvant may only have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may also result from providing the patient with another therapeutic agent for diabetes. In any case, regardless of the disease, disorder, or condition being treated, the patient's overall benefit may simply be additive of the two therapeutic agents, or the patient may experience a synergistic benefit.

In any case, the multiple therapeutic agents (at least one of which is a compound disclosed herein) may be administered in any order or even simultaneously. If simultaneously, the multiple therapeutic agents may be provided in a single, unified form, or multiple forms (by way of example only, either as a single pill or as two separate pills). One of the therapeutic agents may be given in multiple doses, or both may be given in multiple doses. If not simultaneous, the timing between the multiple doses may be any duration ranging from a few min to four weeks.

The present disclosure further provides a method of treating a central nervous system disorder in a patient in need. The method comprising administrating a therapeutically effective amount of a compound described herein to the patient in need thereof. In certain embodiments, the compound is orally administered.

The term "muscarinic disorder" refers to any disease or condition ameliorated by activating the muscarinic system. Such diseases include ones in which direct activation of muscarinic receptors themselves or inhibition of cholinesterase enzymes has produced a therapeutic effect.

The terms "diseases related to schizophrenia" and "disorders related to schizophrenia" include, but are not limited to, schizo-affective disorder, psychosis, delusional disorders, psychosis associated with Alzheimer's disease, psychosis associated with Parkinson's disease, psychotic depression, bipolar disorder, bipolar with psychosis or any other disease with psychotic features.

The term "movement disorders" includes, but is not limited to, Gilles de la Tourette's syndrome, Friederich's ataxia, Huntington's chorea, restless leg syndrome, and other diseases or disorders whose symptoms include excessive movements, tics, and spasms.

The term "mood disorders" includes major depressive disorder, dysthymia, recurrent brief depression, minor depression disorder, bipolar disorder, mania, and anxiety.

The term "cognitive disorders" refers to diseases or disorders marked by a cognitive deficit (e.g., having abnormal working memory, problem-solving abilities, etc.). Diseases include but are not limited to Alzheimer's disease, Parkinson's Disease, dementia (including, but not limited to, AIDS-related dementia, vascular dementia, age-related dementia, dementia associated with Lewy bodies, and idiopathic dementia), Pick's disease, tauopathies, synucleinopathies, confusion, cognitive deficit associated with fatigue, learning disorders, traumatic brain injury, autism, age-related cognitive decline, and Cushing's Disease, a cognitive impairment associated with autoimmune diseases The term "attention disorders" refers to diseases or conditions marked by having an abnormal or decreased attention span. Diseases include but are not limited to attention deficit hyperactivity disorder (ADHD), attention deficit disorder (ADD), Dubowitz Syndrome, FG Syndrome, Down's Syndrome, growth delay due to insulin-like growth factor I (IGF1) deficiency, hepatic encephalopathy syndrome, and Strauss Syndrome.

The term "addictive disorders" refers to diseases or conditions marked by addiction or substance dependence as defined by the Diagnostic & Statistical Manual V (DSM-5). Such disorders are characterized by physical dependence, withdrawal, and tolerance to a substance. Such substances include but are not limited to alcohol, cocaine, amphetamines, opioids, benzodiazepines, inhalants, nicotine, barbiturates, cocaine, and *cannabis*. Addictive disorders also encompass behaviors that a patient does compulsively or continually despite clear negative consequences. For instance, ludomania (gambling addiction, or compulsive gambling) is recognized by those skilled in the art as addictive behavior that often has devastating consequences. In certain embodiments, the addictive behavior may be Internet Gaming Disorder (gaming addiction), as defined in the DSM-5.

The term "pain" refers to physical suffering or discomfort caused by illness or injury. Pain is a subjective experience, and the perception of pain is performed parts of the central nervous system (CNS). Usually, noxious (peripheral) stimuli are transmitted to the CNS beforehand, but pain is not always associated with nociception. A wide variety of clinical pain exists, derived from different underlying pathophysiological mechanisms, and need different treatment approaches. Three major types of clinical pain have been characterized: acute pain, chronic pain, and neuropathic pain. In certain embodiments, the compound potently and effectively reverses tactile allodynia and heat hyperalgesia associated with established neuropathic and inflammatory pain in both rat and mouse models. In certain embodiments, pain is treated, and the type of pain is chosen from allodynia, hyperalgesia, nociceptive pain, inflammatory pain, and neuropathic pain. In certain embodiments, the pain is allodynia. In certain embodiments, the pain is hyperalgesia. In certain embodiments, the pain is nociceptive. In certain embodiments, the pain is inflammatory. In certain embodiments, the pain is neuropathic pain.

In certain embodiments, the central nervous system disorder is chosen from schizophrenia, Alzheimer's disease, Huntington's disease, Parkinson's disease, Lewy Body dementia, psychosis, and cognition deficits. In certain embodiments, the central nervous system disorder is schizophrenia. In certain embodiments, the central nervous system disorder is Alzheimer's disease. In certain embodiments, the central nervous system disorder is Huntington's disease. In certain embodiments, the central nervous system disorder is Parkinson's disease. In certain embodiments, the central nervous system disorder is Lewy Body dementia. In certain embodiments, the central nervous system disorder is psychosis. In certain embodiments, the central nervous system disorder is a cognition deficit.

Besides being useful for human treatment, certain compounds and formulations disclosed herein may also be useful for veterinary treatment of companion animals, exotic animals, and farm animals, including mammals, rodents, and the like. Additional examples of animals include horses, dogs, and cats.

Provided herein are the following specific embodiments:

Embodiment 1: A compound of Formula I

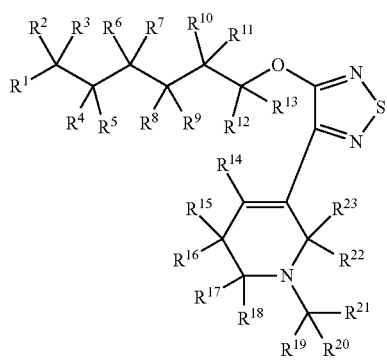

Formula I and/or salts thereof;
wherein at least one of $R^1$, $R^2$, $R^3$, $R^4$, $R^5$, $R^6$, $R^7$, $R^8$, $R^9$, $R^{10}$, $R^{11}$, $R^{12}$, and $R^{13}$ is fluorine, and the remainder are independently chosen from hydrogen and fluorine; and $R^{14}$, $R^{15}$, $R^{16}$, $R^{17}$, $R^{18}$, $R^{19}$, $R^{20}$, $R^{21}$, $R^{22}$, and $R^{23}$ are independently chosen from hydrogen and deuterium;
with the proviso that when $R^1$, $R^2$, and $R^3$ are fluorine, then at least one of $R^4$, $R^5$, $R^6$, $R^7$, $R^8$, $R^9$, $R^{10}$, $R^{11}$, $R^{12}$, and $R^{13}$ is fluorine or at least one of $R^{14}$, $R^{15}$, $R^{16}$, $R^{17}$, $R^{18}$, $R^{19}$, $R^{20}$, $R^{21}$, $R^{22}$ and $R^{23}$ is deuterium.

Embodiment 2: The compound of Embodiment 1, wherein the structure of Formula I is a structure of Formula II

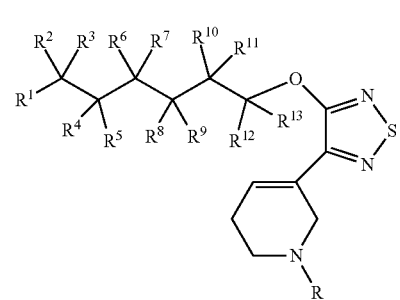

Formula II and/or salts thereof;
wherein at least one of $R^1$, $R^2$, $R^3$, $R^4$, $R^5$, $R^6$, $R^7$, $R^8$, $R^9$, $R^{10}$, $R^{11}$, $R^{12}$, and $R^{13}$ is fluorine, and the remainder are independently chosen from hydrogen and fluorine; and R is $CH_3$ or $CD_3$;
with the proviso that when $R^1$, $R^2$, and $R^3$ are fluorine, then at least one of $R^4$, $R^5$, $R^6$, $R^7$, $R^8$, $R^9$, $R^{10}$, $R^{11}$, $R^{12}$, and $R^{13}$ is fluorine or R is $CD_3$.

Embodiment 3: The compound of Embodiment 1, wherein the structure of Formula I is a structure of Formula IIA

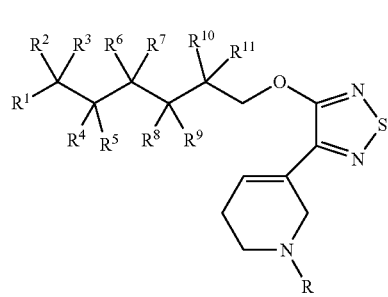

Formula IIA and/or salts thereof;
wherein at least one of $R^1$, $R^2$, $R^3$, $R^4$, $R^5$, $R^6$, $R^7$, $R^8$, $R^9$, $R^{10}$, and R is fluorine, and the remainder are independently chosen from hydrogen and fluorine; and R is $CH_3$ or $CD_3$;
with the proviso that when $R^1$, $R^2$, and $R^3$ are fluorine, then at least one of $R^4$, $R^5$, $R^6$, $R^7$, $R^8$, $R^9$, $R^{10}$, and $R^1$ fluorine or R is $CD_3$.

Embodiment 4: The compound of Embodiment 1, wherein the structure of Formula I is a structure of Formula IIB

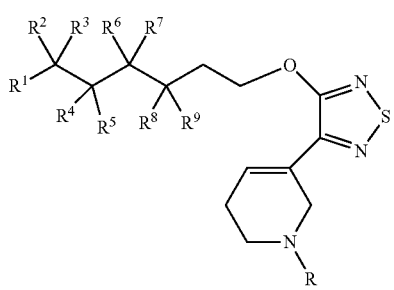

Formula IIB and/or salts thereof;

wherein at least one of $R^1$, $R^2$, $R^3$, $R^4$, $R^5$, $R^6$, $R^7$, $R^8$, and $R^9$ is fluorine, and the remainder are independently chosen from hydrogen and fluorine; and R is $CH_3$ or $CD_3$;

with the proviso that when $R^1$, $R^2$, and $R^3$ are fluorine, then at least one of $R^4$, $R^5$, $R^6$, $R^7$, $R^8$, and $R^9$ is fluorine or R is $CD_3$.

Embodiment 5: The compound of Embodiment 1, wherein the structure of Formula I is a structure of Formula IIC

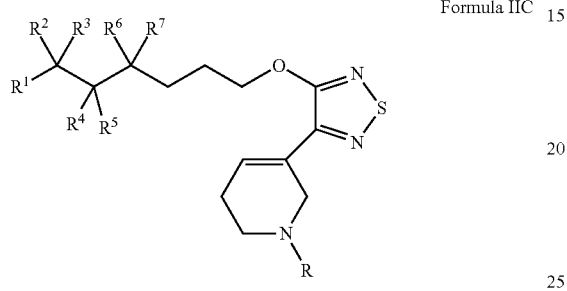

Formula IIC and/or salts thereof;

wherein at least one of $R^1$, $R^2$, $R^3$, $R^4$, $R^5$, $R^6$, and $R^7$ is fluorine, and the remainder are independently chosen from hydrogen and fluorine; and R is $CH_3$ or $CD_3$;

with the proviso that when $R^1$, $R^2$, and $R^3$ are fluorine, then at least one of $R^4$, $R^5$, $R^6$, and $R^7$ is fluorine or R is $CD_3$.

Embodiment 6: The compound of Embodiment 1 chosen from,

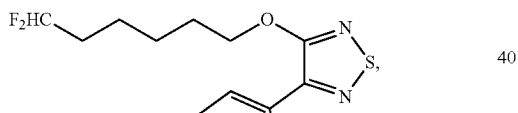

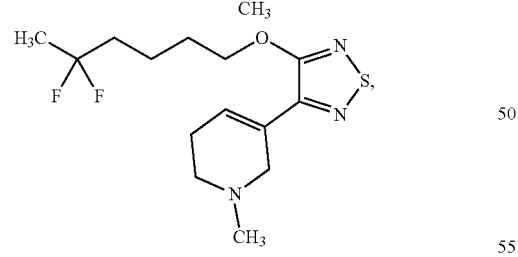

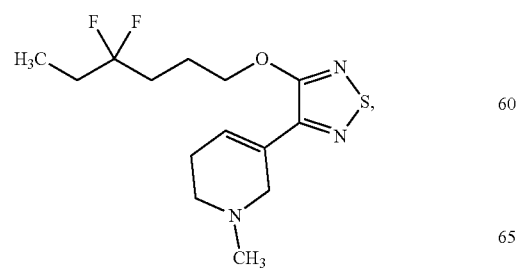

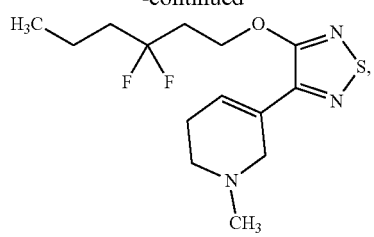

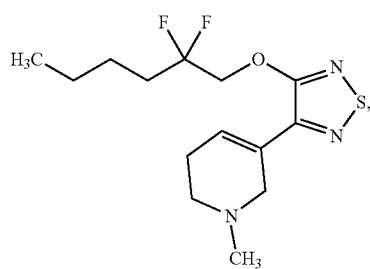

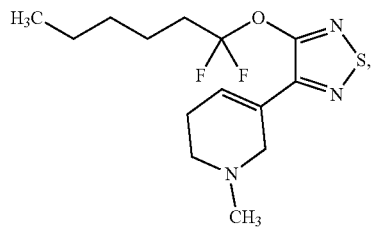

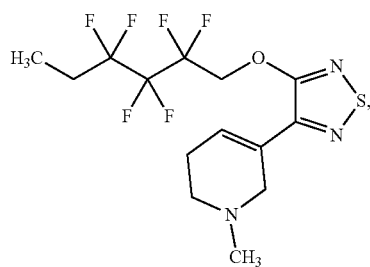

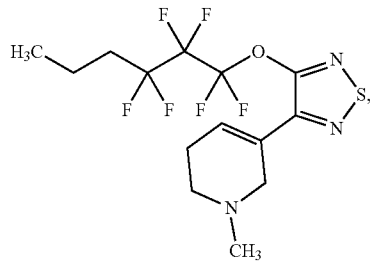

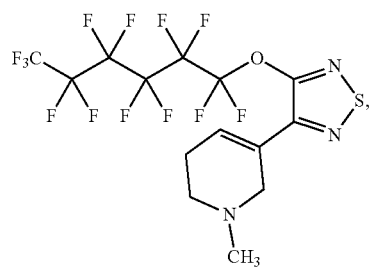

31
-continued
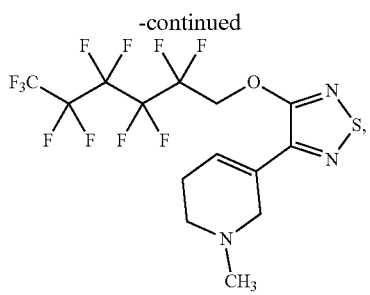
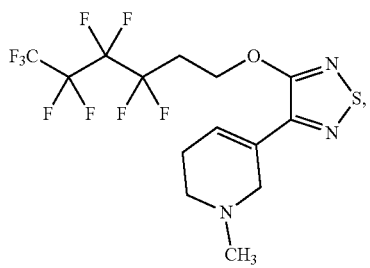
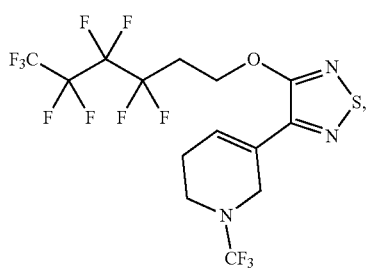
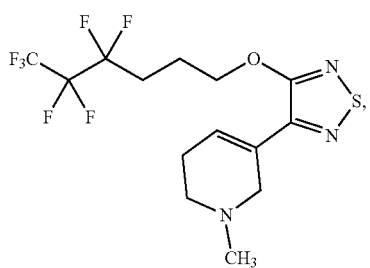
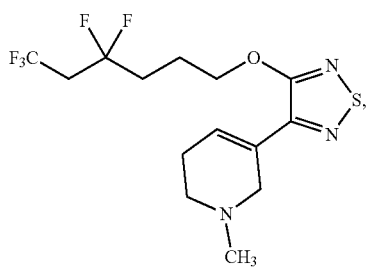
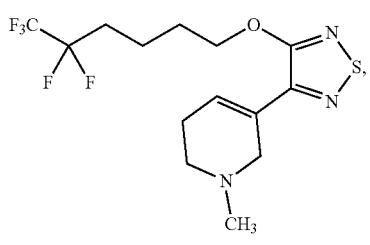
32
-continued
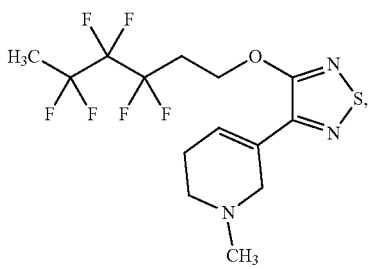
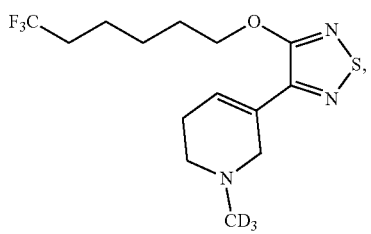
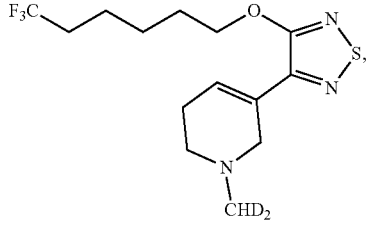
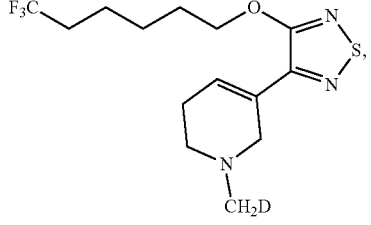
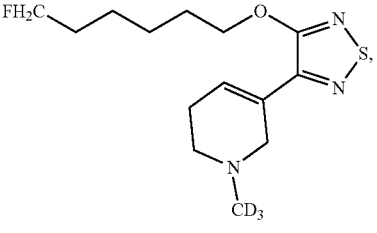
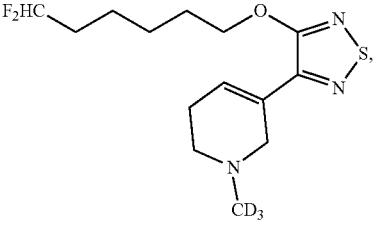
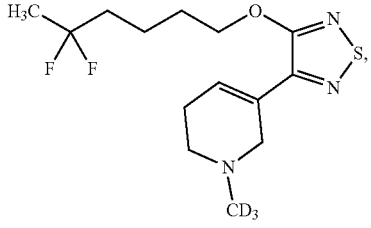

-continued
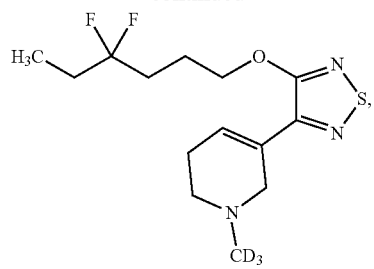
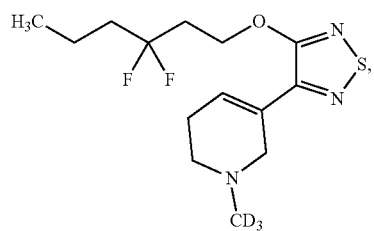
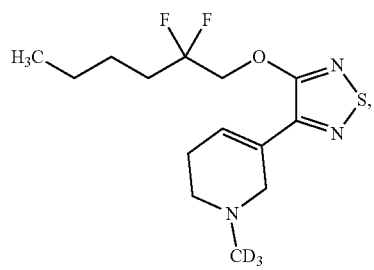
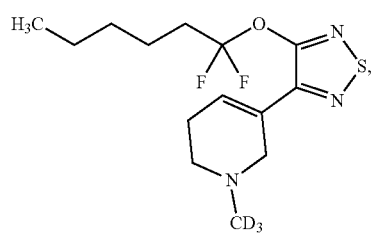
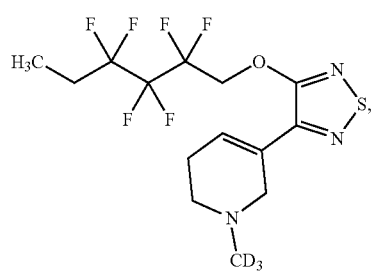
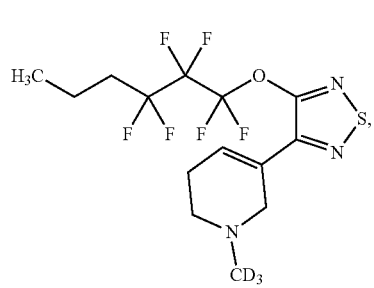
-continued
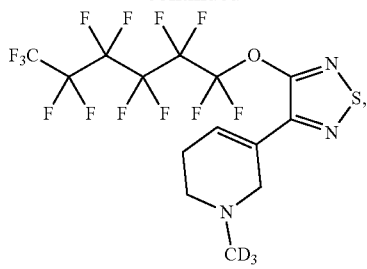
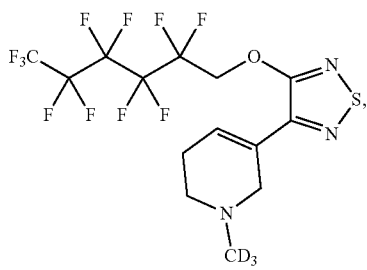
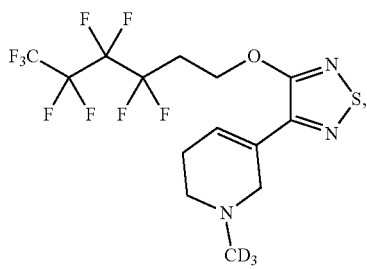
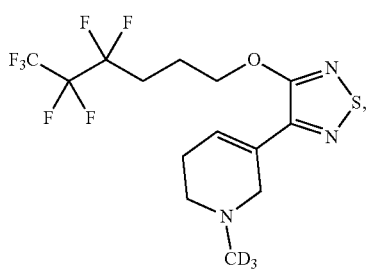
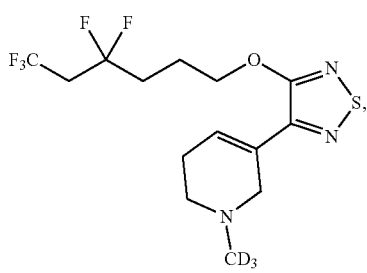
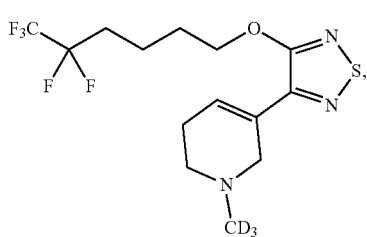

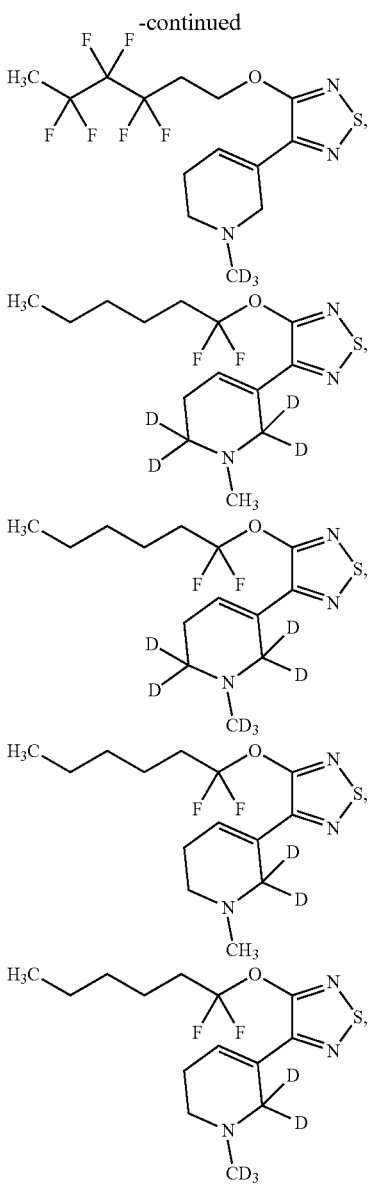

and/or salts thereof.

Embodiment 7: The compound of any preceding Embodiment having a deuterium enrichment of no less than about 10%.

Embodiment 8: The compound of any preceding Embodiment having a deuterium enrichment of no less than about 50%.

Embodiment 9: The compound of any preceding Embodiment having a deuterium enrichment of no less than about 90%.

Embodiment 10: The compound of any preceding Embodiment having a deuterium enrichment of no less than about 98%.

Embodiment 11: A medicament comprising a compound of any preceding Embodiment and/or a salt thereof and a pharmaceutically acceptable carrier.

Embodiment 12: The medicament of Embodiment 11, comprising between 5 mg and 300 mg of the compound.

Embodiment 13: The medicament of Embodiment 11, further comprising a muscarinic inhibitor.

Embodiment 14: The medicament of Embodiment 13, wherein the muscarinic inhibitor is trospium chloride.

Embodiment 15: The medicament of Embodiment 14, comprising between 10 mg and 150 mg trospium chloride.

Embodiment 16: The medicament of any of Embodiments 11-15, formulated as an immediate-release formulation.

Embodiment 17: The medicament of any of Embodiments 11-15, formulated as a controlled release formulation.

Embodiment 18: The medicament of Embodiments 16 or 17, wherein the compound is formulated as a controlled release formulation and the trospium chloride is formulated as an immediate-release formulation.

Embodiment 19: The medicament of Embodiment 18, comprising between 5 mg and 300 mg of the compound and between 5 mg and 150 mg trospium chloride in a single dosage form.

Embodiment 20: The medicament of any of Embodiments 11-19, comprising 10 milligrams of the compound.

Embodiment 21: The medicament of any of Embodiments 11-19, comprising 20 milligrams of the compound.

Embodiment 22: The medicament of any of Embodiments 11-19, comprising 30 milligrams of the compound.

The medicament of any of Embodiments 11-19, comprising 40 milligrams of the compound.

Embodiment 23: The medicament of any of Embodiments 11-19, comprising 50 milligrams of the compound.

Embodiment 24: The medicament of any of Embodiments 11-19, comprising 75 milligrams of the compound.

Embodiment 25: The medicament of any of Embodiments 11-19, comprising 125 milligrams of the compound.

Embodiment 26: The medicament of any of Embodiments 11-19, comprising 200 milligrams of the compound.

Embodiment 27: The medicament of any of Embodiments 11-19, comprising 300 milligrams of the compound.

Embodiment 28: The medicament of Embodiment 19, comprising 10 milligrams trospium chloride.

Embodiment 29: The medicament of Embodiment 19, comprising 20 milligrams trospium chloride.

Embodiment 30: The medicament of Embodiment 19, comprising 40 milligrams trospium chloride.

Embodiment 31: The medicament of Embodiment 19, comprising 80 milligrams trospium chloride.

Embodiment 32: The medicament of Embodiment 19, comprising 120 milligrams trospium chloride.

Embodiment 33: The medicament of Embodiment 19, comprising 150 milligrams trospium chloride.

Embodiment 34: The medicament of Embodiment 19, in the form of a single dosage formulation consisting essentially of 50 milligrams of the compound, 10 milligrams trospium chloride, and a pharmaceutically acceptable carrier.

Embodiment 35: The medicament of Embodiment 19, in the form of a single dosage formulation consisting essentially of 75 milligrams of the compound, 20 milligrams trospium chloride, and a pharmaceutically acceptable carrier.

Embodiment 36: The medicament of Embodiment 19, in the form of a single dosage formulation consisting essentially of 50 milligrams of the compound, 20 milligrams trospium chloride, and a pharmaceutically acceptable carrier.

Embodiment 37: The medicament of Embodiment 19, in the form of a single dosage formulation consisting essentially of 75 milligrams of the compound, 10 milligrams trospium chloride, and a pharmaceutically acceptable carrier.

Embodiment 38: The medicament of any of Embodiments 11-38 wherein the pharmaceutically acceptable carrier comprises cellulose and lactose.

Embodiment 39: A method of treating pain or a central nervous system disorder in a patient in need thereof, comprising administrating therapeutically effective amount of a compound from any one of Embodiments 1-10 to the patient in need thereof.

Embodiment 40: The method of Embodiment 40, wherein the compound is administered orally, intramuscularly, transdermally, buccally, or sublingually.

Embodiment 41: The method of Embodiment 40 or 41, wherein a central nervous system disorder is treated and is chosen from schizophrenia, Alzheimer's disease, Huntington's disease, Parkinson's disease, Lewy Body dementia, psychosis, and cognition deficit.

Embodiment 42: A method of treating pain or a central nervous system disorder in a patient in need thereof, the method comprising administrating therapeutically effective amount of a medicament from Embodiments 11-39 to the patient in need thereof.

Embodiment 43: The method of Embodiment 43, wherein the medicament is administered orally, intramuscularly, transdermally, buccally, or sublingually.

Embodiment 44: The method of Embodiment 43 or 44, wherein a central nervous system disorder is treated and is chosen from schizophrenia, Alzheimer's disease, Huntington's disease, Parkinson's disease, Lewy Body dementia, psychosis, and cognition deficit.

Embodiment 45: The method of any of Embodiments 40-45, wherein use of the trospium chloride, when present, alleviates a side effect associated with use of the compound from Embodiments 1-6 or the medicament from Embodiments 11-39.

LIST OF ABBREVIATIONS $Ac_2O$=acetic anhydride; AcCl=acetyl chloride; AcOH=acetic acid; AIBN=azobisisobutyronitrile; aq.=aqueous; BAST=bis(2-methoxyethyl)aminosulfur trifluoride; Bu=butyl; $Bu_3SnH$=tributyltin hydride; $CD_3OD$=deuterated methanol; $CDCl_3$=deuterated chloroform; CDI=1,1'-carbonyldiimidazole; DAST=(diethylamino)sulfur trifluoride; dba=dibenzylideneacetone DBU=1,8-diazabicyclo[5.4.0]undec-7-ene; DCM=dichloromethane; PE=petroleum ether; DEAD=diethyl azodicarboxylate; DIBAL-H=di-iso-butyl aluminum hydride; DIEA=DIPEA=N,N-diisopropylethylamine; DMAP=4-dimethylaminopyridine; DMF=N,N-dimethylformamide; DMSO-$d_6$=deuterated dimethyl sulfoxide; DMSO=dimethyl sulfoxide; DPPA=diphenylphosphoryl azide; dppf=1,1'-bis(diphenylphosphino)ferrocene; EDC.HCl=EDCI.HCl=1-ethyl-3-(3-dimethylaminopropyl) carbodiimide hydrochloride; Et=ethyl; $Et_2O$=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexa- methyldisilazane; HOBT=1-hydroxybenzotriazole; iPr=i-Pr=isopropyl=2-propyl; iPrOH=i-PrOH=isopropanol; LAH=lithium aluminohydride; LDA=lithium diisopropyl amide; LiHMDS=Lithium bis(trimethylsilyl)amide; MeCN=acetonitrile; MeI=methyl iodide; MeOH=methanol; MP-carbonate resin=macroporous triethylammonium methylpolystyrene carbonate resin; MsCl=mesyl chloride; MTBE=methyl tert-butyl ether; n-BuLi=n-butyllithium; NaHMDS=Sodium bis(trimethylsilyl)amide; NaOEt=sodium ethoxide; NaOMe=sodium methoxide; NaOtBu=sodium t-butoxide; NBS=N-bromosuccinimide; NCS=N-chlorosuccinimide; NIS=N-iodosuccinimide; NMP=N-Methyl-2-pyrrolidone; $Pd(Ph_3)_4$=tetrakis(triphenylphosphine)palladium(0); $Pd_2(dba)_3$=tris(dibenzylideneacetone)dipalladium(0); $PdCl_2(PPh_3)_2$=bis(triphenylphosphine)palladium(II) dichloride; PG=protecting group; Ph=phenyl; prep-HPLC=preparative high-performance liquid chromatography; PMBCl=para-methoxybenzyl; PMBCl=para-methoxybenzyl chloride; PMBOH=para-methoxybenzyl alcohol; PyBop=(benzotriazol-1-yloxy) tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; tBu=t-Bu=tert-butyl=1,1-dimethylethyl; TBAF=tetrabutylammonium fluoride; TBDPS=t-butyldiphenylsilyl; t-BuOH=tBuOH=tert-butanol; T3P=Propylphosphonic Anhydride; TEA=$Et_3N$=triethylamine; TFA=trifluoroacetic acid; TFAA=trifluoroacetic anhydride; THF=tetrahydrofuran; TIPS=triisopropylsilyl; Tol=toluene; TsCl=tosyl chloride; Trt=trityl=(triphenyl)methyl; Xantphos=4,5-Bis(diphenylphosphino)-9,9-dimethylxanthene; XPhos=2-dicyclohexylphosphino-2',4',6'-triisopropylbiphenyl.

EXAMPLES

LCMS Methods

For each method, the MS range was 100-1000 amu. LCMS method 1 was performed using an Xbridge Shield™ RP18 2.1*50 mm column (5 μm particles). Detection methods are diode array (DAD) as well as positive electrospray ionization. Flow rate=0.8 mL/min. Mobile phase A: $H_2O$+10 mM $NH_4HCO_3$. Mobile phase B: Acetonitrile. Gradient: 0-0.4 min (5% B); 0.4-3.40 min (5% B to 95% B); 3.40-3.85 min (95% B); 3.85-3.95 min (95% B to 5% B). LCMS method 2 was performed using a Kinetex™ C18 50×2.1 mm column (5 μm particles). Detection methods are diode array (DAD) as well as positive electrospray ionization. Flow rate=1.0 mL/min. Mobile phase: A=0.05% trifluoroacetic acid in water; B=0.05% trifluoroacetic acid in acetonitrile. Gradient: 0-0.4 min (5% B); 0.4-3.0 min (5% B to 95% B); 3.0-4.0 min (95% B); 4.0-4.1 min (95% B to 5% B). LCMS method 3 was performed using an Ascentis Express HPLC Column C18 10 cm*4.6 mm (2.7 μm particles). Detection methods are diode array (DAD) and evaporative light scattering (ELSD) as well as positive electrospray ionization. Flow rate=1.0 mL/min. Mobile phase A was 0.05% trifluoroacetic acid in water, mobile phase B was 0.05% trifluoroacetic acid in acetonitrile. Gradient: 0-5.6 min (30% B to 50% B); 5.6-7.6 min (50% B to 100% B). LCMS method 4 was performed using the same column and mobile phase and flow rate as indicated in method 3. Gradient: 0-5.6 min (30-60% B); 5.6-7.6 min (60% B to 100% B). LCMS method 5 was performed using a Kinetix™ 5 μm EVO C18 100A 30×2.1 mm column with diode array detection. MS mode was positive electrospray with MS range of 100-1000. Flow rate=1.5 mL/min. Mobile phase A was 0.05% trifluoroacetic acid in water, mobile phase B was 0.05% trifluoroacetic acid in HPLC grade acetonitrile. Gradient: 0-0.01 min (5% B), 0.01-0.7 min (5% B to 95% B), 0.7-1.15 min (95% B), 1.16-1.5 min (5% B).

NMR Methods $^1H$ and $^{19}F$ NMR spectra were recorded on either: 1) Varian 400 or 2) Bruker Avance NEO 400 spectrometer. Chemical shifts are quoted relative to TMS for 1H NMR and 19F NMR spectra. Chemical shift values are reported in delta (δ) units, parts per million (ppm). Chemical shifts for $^1$H NMR spectra are given relative to signals for residual non-deuterated solvent (CDCl$_3$ referenced at δ 7.26 ppm; DMSO d$_6$ referenced at δ 2.50 ppm and CD$_3$OD referenced at δ 3.31 ppm).

Scheme I depicts a general synthesis for installing a fluorinated ether chain and/or a deuteromethyl group in xanomeline. 3-Chloro-4-(pyridin-3-yl)-1,2,5-thiadiazole (1) was reacted in a Williamson ether synthesis with n-hexanol and sodium hydride in toluene to yield 3-(hexyloxy)-4-(pyridin-3-yl)-1,2,5-thiadiazole (2). Compound 2 was reacted with iodomethane in acetone and pyridine to yield 3-(4-(hexyloxy)-1,2,5-thiadiazol-3-yl)-1-methylpyridin-1-ium iodide (3), which was then reduced with sodium borohydride in methanol to yield xanomeline free base (4).

To install a fluorinated ether chain, n-hexanol is substituted with a fluorinated hexanol, (5') to yield 3-((fluorohexyloxy)-4-(pyridin-3-yl)-1,2,5-thiadiazole (6'). Particular examples of fluorinated hexanols are described herein below. When compound 6' is reacted with iodomethane, 3-(4-(fluorohexyloxy)-1,2,5-thiadiazol-3-yl)-1-methylpyridin-1-ium iodide (7') results and is then reduced to yield 3-(fluorohexyloxy)-4-(1-methyl-1,2,5,6-tetrahydropyridin-3-yl)-1,2,5-thiadiazole (8'). When compound 6' is reacted with deuteroiodomethane, 3-(4-(fluorohexyloxy)-1,2,5-thiadiazol-3-yl)-1-(deuteromethylpyridin-1-ium iodide (9') results and is then reduced to yield 3-(fluorohexyloxy)-4-(1-(deuteromethyl)-1,2,5,6-tetrahydropyridin-3-yl)-1,2,5-thiadiazole (10').

The following scheme can generally be used to practice the present disclosure:

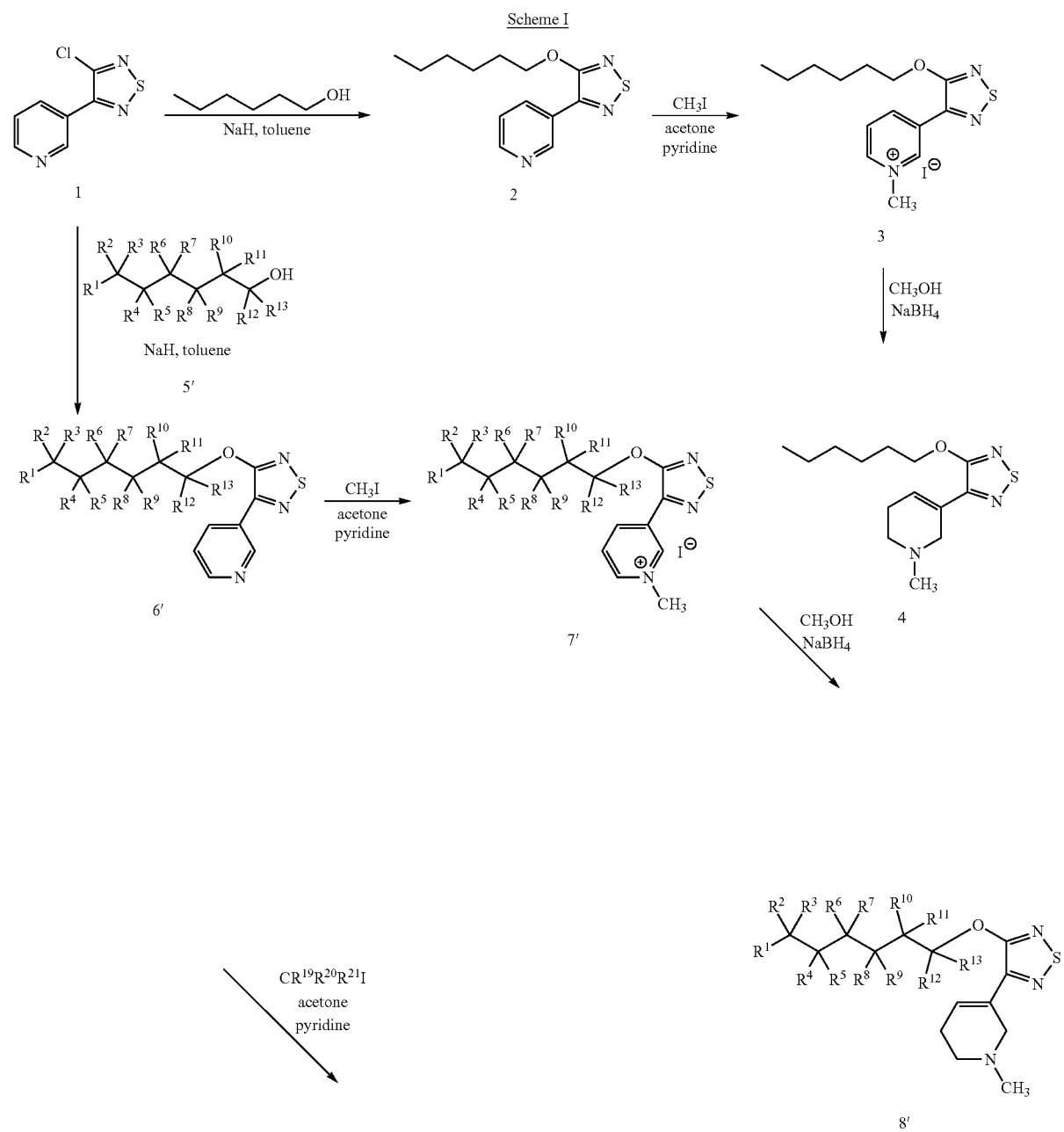

Scheme I

-continued

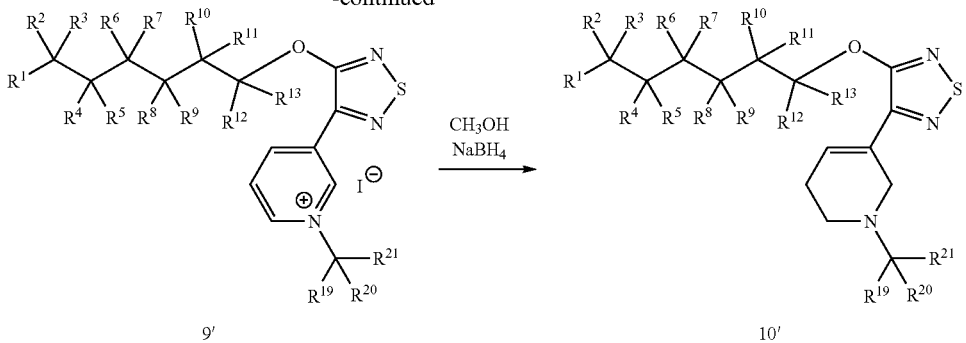

Example 1—3-(1-Methyl-1,2,5,6-tetrahydropyridin-3-yl)-4-((6,6,6-trifluorohexyl)oxy)-1,2,5-thiadiazole

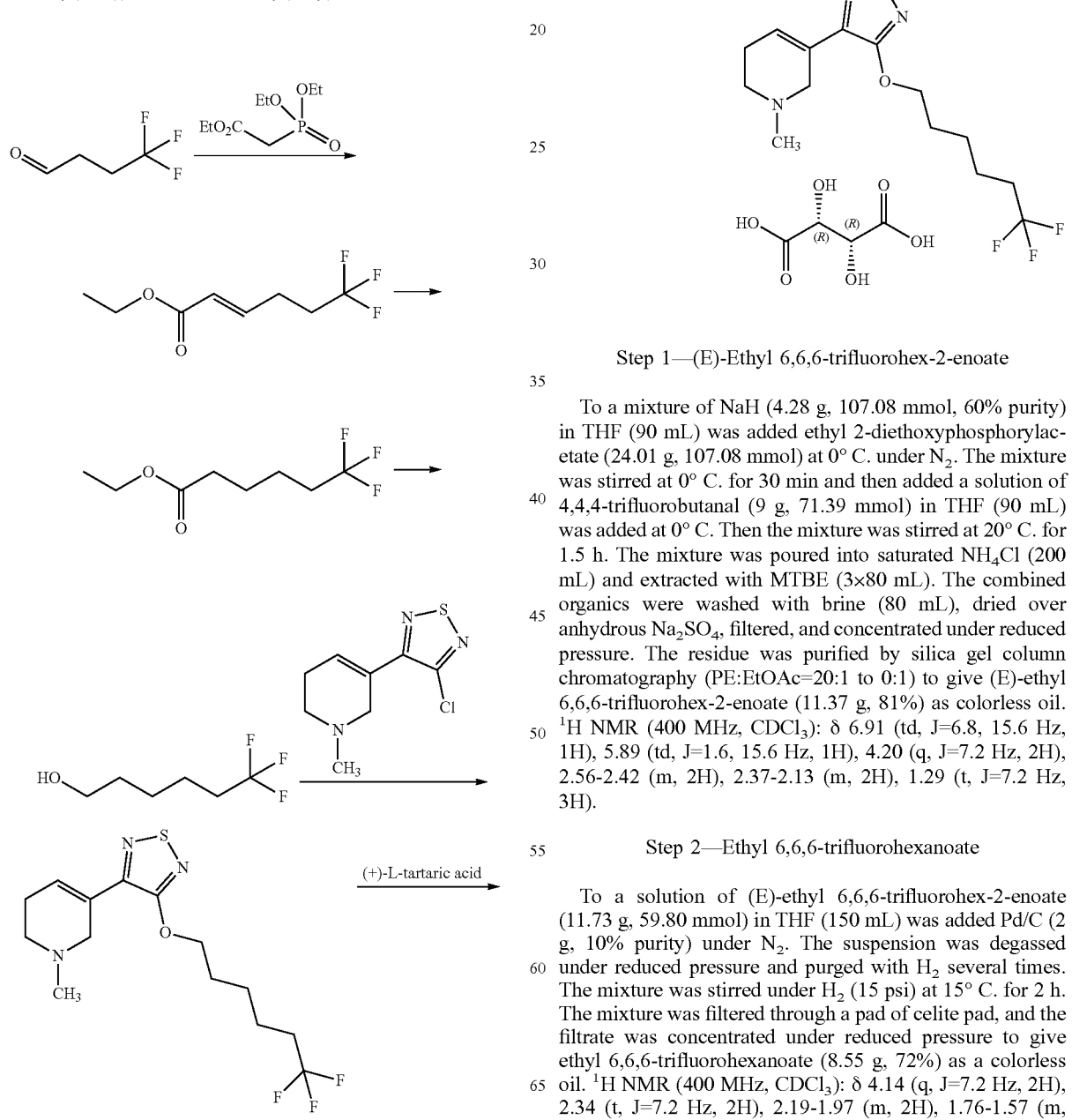

Step 1—(E)-Ethyl 6,6,6-trifluorohex-2-enoate

To a mixture of NaH (4.28 g, 107.08 mmol, 60% purity) in THF (90 mL) was added ethyl 2-diethoxyphosphorylacetate (24.01 g, 107.08 mmol) at 0° C. under $N_2$. The mixture was stirred at 0° C. for 30 min and then added a solution of 4,4,4-trifluorobutanal (9 g, 71.39 mmol) in THF (90 mL) was added at 0° C. Then the mixture was stirred at 20° C. for 1.5 h. The mixture was poured into saturated $NH_4Cl$ (200 mL) and extracted with MTBE (3×80 mL). The combined organics were washed with brine (80 mL), dried over anhydrous $Na_2SO_4$, filtered, and concentrated under reduced pressure. The residue was purified by silica gel column chromatography (PE:EtOAc=20:1 to 0:1) to give (E)-ethyl 6,6,6-trifluorohex-2-enoate (11.37 g, 81%) as colorless oil. $^1$H NMR (400 MHz, $CDCl_3$): δ 6.91 (td, J=6.8, 15.6 Hz, 1H), 5.89 (td, J=1.6, 15.6 Hz, 1H), 4.20 (q, J=7.2 Hz, 2H), 2.56-2.42 (m, 2H), 2.37-2.13 (m, 2H), 1.29 (t, J=7.2 Hz, 3H).

Step 2—Ethyl 6,6,6-trifluorohexanoate

To a solution of (E)-ethyl 6,6,6-trifluorohex-2-enoate (11.73 g, 59.80 mmol) in THF (150 mL) was added Pd/C (2 g, 10% purity) under $N_2$. The suspension was degassed under reduced pressure and purged with $H_2$ several times. The mixture was stirred under $H_2$ (15 psi) at 15° C. for 2 h. The mixture was filtered through a pad of celite pad, and the filtrate was concentrated under reduced pressure to give ethyl 6,6,6-trifluorohexanoate (8.55 g, 72%) as a colorless oil. $^1$H NMR (400 MHz, $CDCl_3$): δ 4.14 (q, J=7.2 Hz, 2H), 2.34 (t, J=7.2 Hz, 2H), 2.19-1.97 (m, 2H), 1.76-1.57 (m, 4H), 1.26 (t, J=7.2 Hz, 3H).

Step 3—6,6,6-Trifluorohexan-1-ol

To a mixture of ethyl 6,6,6-trifluorohexanoate (8.55 g, 43.14 mmol) in THF (100 mL) was added LAH (3.27 g, 86.28 mmol) in portions at 0° C. under $N_2$. The mixture was stirred at 0° C. for 1 h. The mixture was quenched by the addition of $Na_2SO_4 \cdot 10H_2O$ at 0° C. and stirred for 30 min. The mixture was filtered through a pad of celite, and the filtrate was concentrated under reduced pressure to give 6,6,6-trifluorohexan-1-ol (5.1 g, 66%) as a colorless oil. $^1$H NMR (400 MHz, CDCl$_3$): δ 3.71-3.62 (m, 2H), 2.16-2.02 (m, 2H), 1.68-1.53 (m, 4H), 1.51-1.41 (m, 3H).

Step 4—3-(1-Methyl-1,2,5,6-tetrahydropyridin-3-yl)-4-((6,6,6-trifluorohexyl)oxy)-1,2,5-thiadiazole To a solution of 6,6,6-trifluorohexan-1-ol (1 g, 6.40 mmol) in THF (15 mL) was added NaH (1.54 g, 38.43 mmol, 60% purity) at 0° C. Then the reaction was stirred at 0° C. for 0.5 h. Then 3-chloro-4-(1-methyl-3,6-dihydro-2H-pyridin-5-yl)-1,2,5-thiadiazole hydrochloride salt (1.61 g, 6.40 mmol) was added to reaction mixture at 20° C. Then the reaction was stirred at 20° C. for 12 h. The reaction mixture was diluted with $H_2O$ (10 mL) and extracted with EtOAc (3×20 mL). The combined organic layers were dried over $Na_2SO_4$, filtered and concentrated under reduced pressure. The residue was purified by prep-HPLC (neutral) with the following conditions: column: Welch Xtimate™ C18 250*70 mm #10 μm; mobile phase: [water (10 mM $NH_4HCO_3$)-ACN]; B %: 47%-77%, 25 min to give 3-(1-methyl-3,6-dihydro-2H-pyridin-5-yl)-4-(6,6,6-trifluorohexoxy)-1,2,5-thiadiazole (900 mg, 42%) as yellow solid. LC-MS: m/z: 336.1[M+H]+. $^1$H NMR (400 MHz, DMSO): δ 7.00 (br s, 1H), 4.43 (t, J=6.4 Hz, 2H), 3.26 (s, 2H), 2.48-2.43 (m, 2H), 2.39-2.30 (m, 5H), 2.29-2.19 (m, 2H), 1.82-1.80 (m, 2H), 1.61-1.45 (m, 4H).

Step 5—3-(1-Methyl-1,2,5,6-tetrahydropyridin-3-yl)-4-((6,6,6-trifluorohexyl)oxy)-1,2,5-thiadiazole (2R,3R)-2,3-dihydroxysuccinate To a solution of 3-(1-methyl-3,6-dihydro-2H-pyridin-5-yl)-4-(6,6,6-trifluorohexoxy)-1,2,5-thiadiazole (300 mg, 0.89 mmol) in MeOH (2 mL) was added a solution of (2R,3R)-2,3-dihydroxybutanedioic acid (132 mg, 0.87 mmol) in MeOH (2 mL) at 25° C. The mixture was stirred at 25° C. for 12 h. The mixture was concentrated under reduced pressure. The residue was slurried with MTBE (5 mL) and filtered to give 3-(1-methyl-1,2,5,6-tetrahydropyridin-3-yl)-4-((6,6,6-trifluorohexyl)oxy)-1,2,5-thiadiazole (2R,3R)-2,3-dihydroxysuccinate (300 mg) as yellow solid. LC-MS Method 1: m/z: 336.1[M+H]+, RT=2.000 min (100% purity). $^1$H NMR (400 MHz, DMSO): δ 9.81-7.70 (m, 4H), 7.05 (br s, 1H), 4.45 (br t, J=6.0 Hz, 2H), 4.17 (s, 2H), 3.55 (br s, 2H), 2.72 (br s, 2H), 2.60-2.51 (m, 2H), 2.43 (br s, 3H), 2.37-2.16 (m, 2H), 1.91-1.76 (m, 2H), 1.63-1.42 (m, 4H). $^{19}$F NMR (400 MHz, DMSO): δ −64.572.

After six months of storage at 0° C., no meaningful changes were observed in the LC-MS, $^1$H NMR, or $^{19}$F NMR spectra. LC-MS: using General Analytical Method 2: m/z: 336.1[M+H]+, RT=2.138 min (100% purity). $^1$H NMR (400 MHz, DMSO): δ 7.05 (br s, 1H), 4.45 (br t, J=6.0 Hz, 2H), 4.16 (s, 2H), 3.57 (br s, 2H), 2.75 (br s, 2H), 2.60-2.51 (m, 2H), 2.43 (br s, 3H), 2.37-2.16 (m, 2H), 1.91-1.76 (m, 2H), 1.63-1.42 (m, 4H). $^{19}$F NMR (400 MHz, DMSO): δ −64.687.

Example 2—3-((6,6,6-Trifluorohexyl)oxy)-4-(1-(trifluoromethyl)-1,2,5,6-tetrahydropyridin-3-yl)-1,2,5-thiadiazole

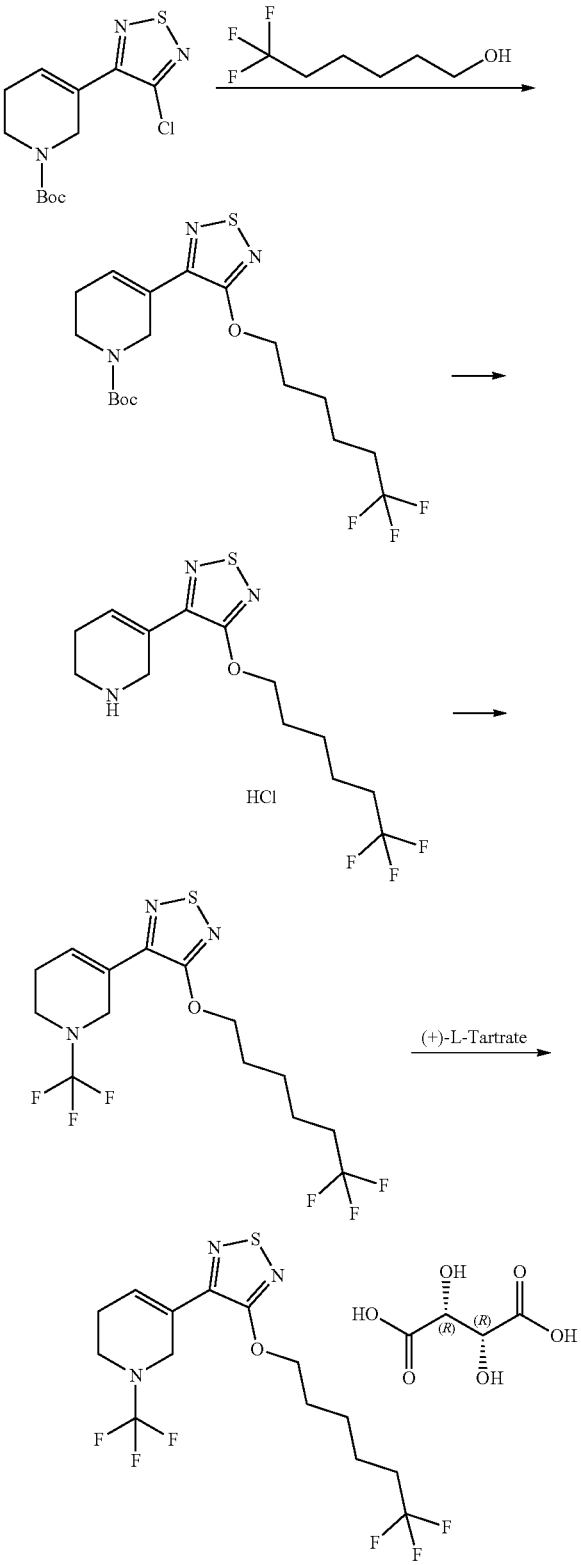

Step 1—tert-Butyl 3-(4-((6,6,6-trifluorohexyl)oxy)-1,2,5-thiadiazol-3-yl)-5,6-dihydropyridine-1(2H)-carboxylate To a suspension of NaH (795 mg, 20 mmol, 60% purity) in toluene (15 mL) was added a solution of 6,6,6-trifluorohexan-1-ol (1.45 g, 9.28 mmol) in toluene (5 mL) dropwise at 25° C., and the mixture was stirred at 25° C. for 45 min. Then the mixture was heated to 60° C. and stirred for 1 h. The mixture was cooled to 25° C. and tert-butyl 3-(4-chloro-1,2,5-thiadiazol-3-yl)-5,6-dihydropyridine-1(2H)-carboxylate (2 g, 6.63 mmol) in portions. The mixture was heated to 80° C. and stirred for 12 h. The mixture was cooled down to 2° C. and diluted with water (20 mL). The mixture was extracted with toluene (10 mL). The combined organic phase was washed with brine (10 mL), dried over anhydrous $Na_2SO_4$, filtered, and concentrated under reduced pressure. The residue was purified by silica gel column chromatography ($SiO_2$,PE:EtOAc=1:0 to 3:1) to give tert-butyl 3-(4-((6,6,6-trifluorohexyl)oxy)-1,2,5-thiadiazol-3-yl)-5,6-dihydropyridine-1(2H)-carboxylate (1.6 g, 57%) as brown oil.

Step 2—3-(1,2,5,6-Tetrahydropyridin-3-yl)-4-((6,6,6-trifluorohexyl)oxy)-1,2,5-thiadiazole hydrochloride A solution of tert-butyl 3-(4-((6,6,6-trifluorohexyl)oxy)-1,2,5-thiadiazol-3-yl)-5,6-dihydropyridine-1(2H)-carboxylate (1.6 g, 3.80 mmol) in HCl/EtOAc (15 mL) was stirred at 25° C. for 2 h. The mixture was concentrated under reduced pressure to give 3-(1,2,5,6-tetrahydropyridin-3-yl)-4-((6,6,6-trifluorohexyl)oxy)-1,2,5-thiadiazole hydrochloride (1.3 g, crude) as brown solid. $^1$H NMR (400 MHz, $CDCl_3$): δ 7.19 (s, 1H), 4.47 (t, J=6.4 Hz, 2H), 4.21 (br s, 2H), 3.37 (br s, 2H), 2.76 (d, J=3.2 Hz, 2H), 2.13-2.09 (m, 2H), 1.90-1.86 (m, 2H), 1.68-1.64 (m, 2H) 1.56-1.54 (m, 2H). $^{19}$F NMR (400 MHz, $CDCl_3$): δ −66.245.

Step 3—3-((6,6,6-Trifluorohexyl)oxy)-4-(1-(trifluoromethyl)-1,2,5,6-tetrahydropyridin-3-yl)-1,2,5-thiadiazole A solution of 3-(1,2,5,6-tetrahydropyridin-3-yl)-4-((6,6,6-trifluorohexyl)oxy)-1,2,5-thiadiazole hydrochloride (200 mg, 0.6 mmol) and tetramethylammonium trifluoromethanethiolate (142 mg, 0.81 mmol) in MeCN (3 mL) was stirred at 25° C. for 1 h. Then AgF (237 mg, 1.87 mmol) was added and the mixture was stirred at 50° C. for 1 h. The mixture was filtered and concentrated under reduced pressure. The crude was purified by prep-HPLC with the following conditions: (column: 3_Phenomenex Luna C18 75*30 mm*3 um; mobile phase: [water (0.2% FA)-ACN]; B %: 70%-90%, 10 min) to give 3-((6,6,6-trifluorohexyl)oxy)-4-(1-(trifluoromethyl)-1,2,5,6-tetrahydropyridin-3-yl)-1,2,5-thiadiazole (50 mg) as colorless oil. $^1$H NMR (400 MHz, $CDCl_3$): δ 7.09-7.07 (m, 1H), 4.48 (t, J=6.4 Hz, 2H), 4.00 (d, J=1.6 Hz, 2H), 3.10 (d, J=5.6 Hz, 2H), 2.46 (d, J=3.6 Hz, 2H), 2.14-2.10 (m, 2H), 1.91-1.88 (m, 2H), 1.67-1.65 (m, 2H), 1.58-1.55 (m, 2H). $^{19}$F NMR (400 MHz, $CDCl_3$): δ −66.348, −66.998.

Step 4—3-((6,6,6-Trifluorohexyl)oxy)-4-(1-(trifluoromethyl)-1,2,5,6-tetrahydropyridin-3-yl)-1,2,5-thiadiazole (2R,3R)-2,3-dihydroxysuccinate The solution of 3-((6,6,6-trifluorohexyl)oxy)-4-(1-(trifluoromethyl)-1,2,5,6-tetrahydropyridin-3-yl)-1,2,5-thiadiazole (12 mg, 0.03 mmol) and (2R,3R)-2,3-dihydroxybutanedioic acid (5 mg, 0.03 mmol) in $H_2O$ (2 mL) was stirred at 25° C. for 1 h. The mixture was concentrated under reduced pressure to give 3-((6,6,6-trifluorohexyl)oxy)-4-(1-(trifluoromethyl)-1,2,5,6-tetrahydropyridin-3-yl)-1,2,5-thiadiazole (2R,3R)-2,3-dihydroxysuccinate (12 mg, 72%) as white solid. LC-MS Method 2: m/z: 390.0[M+H]+, RT=3.346 min (75% purity). $^1$H NMR (400 MHz, DMSO): δ 7.10-7.09 (m, 1H), 4.43 (q, J=6.4 Hz, 2H), 4.25 (s, 2H), 3.90 (br s, 2H), 3.07 (t, J=6.0 Hz, 2H), 2.42 (br s, 2H), 2.30-2.25 (m, 2H), 1.86-1.81 (m, 2H), 1.56-1.50 (m, 4H). $^{19}$F NMR (400 MHz, DMSO): δ −64.512, −64.622.

The tartrate salt of the title compound was unstable at test storage conditions. Although the initial NMR spectra were clean, the LCMS purity was about 75%. After storage at 0° C. for six months, the sample was reanalyzed by $^1$H-NMR, $^{19}$F-NMR, and LC-MS. The new spectral data showed that none of the title compound remained in the sample.

Example 3—3-(Hexyloxy)-4-(1-(trifluoromethyl)-1,2,5,6-tetrahydropyridin-3-yl)-1,2,5-thiadiazole

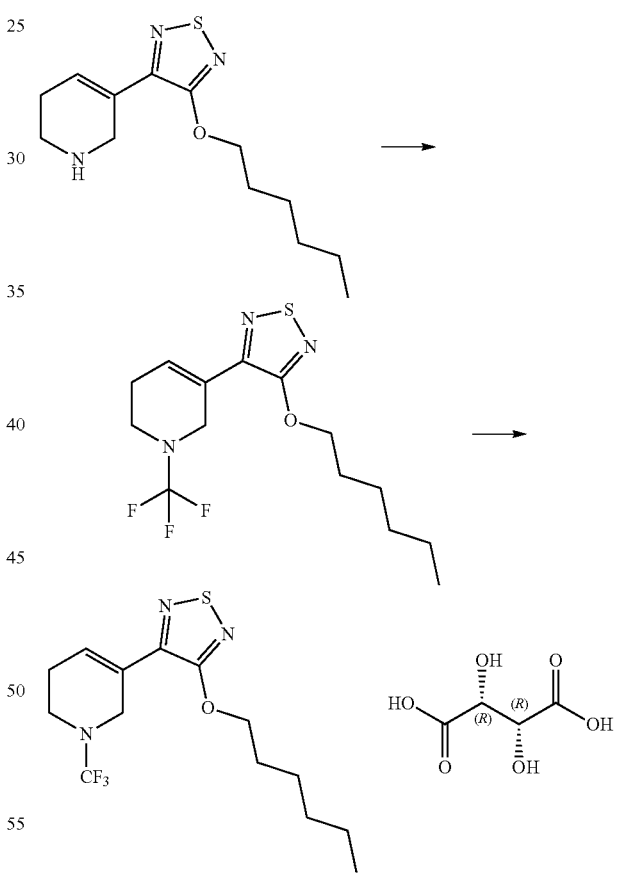

Step 1—3-(Hexyloxy)-4-(1-(trifluoromethyl)-1,2,5,6-tetrahydropyridin-3-yl)-1,2,5-thiadiazole A solution of 3-(hexyloxy)-4-(1,2,5,6-tetrahydropyridin-3-yl)-1,2,5-thiadiazole (300 mg, 1.12 mmol) and tetramethylammonium trifluoromethanethiolate (255 mg, 1.46 mmol) in MeCN (3 mL) was stirred at 25° C. for 1 h. Then AgF (427 mg, 3.37 mmol) was added and the mixture was stirred at 50° C. for 1 h. The mixture was filtered through a pad of celite and the filtrate was concentrated under reduced pressure. The residue was purified by prep-HPLC (FA) with the following conditions: (column: 3_Phenomenex Luna C18 75*30 mm*3 μm; mobile phase: [water (0.2% FA)-ACN]; B %: 70%-99%, 8 min) to give 3-(hexyloxy)-4-(1-(trifluoromethyl)-1,2,5,6-tetrahydropyridin-3-yl)-1,2,5-thiadiazole (42 mg, 11%) as colorless oil. $^1$H NMR (400 MHz, CDCl$_3$): δ 7.14-7.12 (m, 1H), 4.47 (t, J=6.4 Hz, 2H), 4.00 (d, J=2.4 Hz, 2H), 3.10 (t, J=6.0 Hz, 2H), 2.50-2.46 (m, 2H), 1.90-1.83 (m, 2H), 1.48-1.50 (m, 2H), 1.39-1.34 (m, 4H), 0.92 (t, J=7.2 Hz, 3H), $^{19}$F NMR (400 MHz, CDCl$_3$): δ −66.745.

Step 2—3-(Hexyloxy)-4-(1-(trifluoromethyl)-1,2,5,6-tetrahydropyridin-3-yl)-1,2,5-thiadiazole (2R,3R)-2,3-dihydroxysuccinate A solution of 3-(hexyloxy)-4-(1-(trifluoromethyl)-1,2,5,6-tetrahydropyridin-3-yl)-1,2,5-thiadiazole (30 mg, 0.09 mmol) and (2R,3R)-2,3-dihydroxybutanedioic acid (13 mg, 0.09 mmol) in MeOH (5 mL) at 25° C. The mixture was stirred at 25° C. for 16 h. The reaction mixture was concentrated under reduced pressure.

LCMS showed compound turned messy after 2 days. The molecular weight of desired product is 335.39 g/mol. Instead LC-MS, using General Analytical Method 2, showed m/z: 284.3[M+H]+, RT=4.217 min (98.30% purity). $^1$H NMR (400 MHz, MeOD): δ 7.24-7.19 (m, 1H), 4.54 (s, 2H), 4.52-4.46 (m, 4H), 3.63 (t, J=5.6 Hz, 2H), 2.49-2.46 (m, 2H), 1.88-1.83 (m, 2H), 1.52-1.47 (m, 2H), 1.40-1.36 (m, 4H), 0.93 (t, J=7.2 Hz, 3H). $^{19}$F NMR (400 MHz, CDCl$_3$): δ −23.145, −27.445.

Example 6—3-((6,6-difluorohexyl)oxy)-4-(1-methyl-1,2,5,6-tetrahydropyridin-3-yl)-1,2,5-thiadiazole

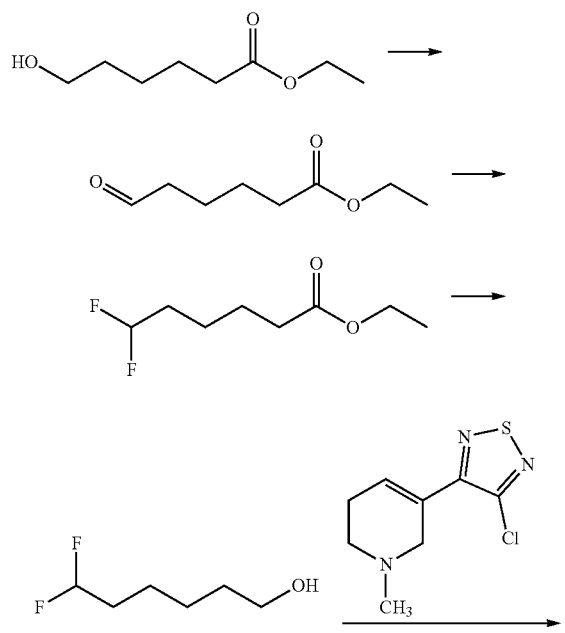

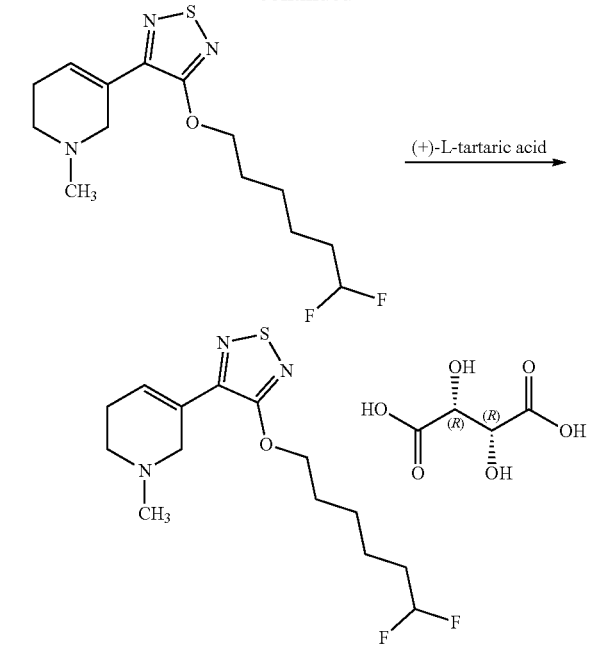

Step 1—Ethyl 6-oxohexanoate

To a mixture of (COCl)$_2$ (31.69 g, 249.67 mmol) in DCM (200 mL) was added a solution of DMSO (29.26 g, 374.51 mmol) in DCM (90 mL) at −78° C. under N$_2$. After 10 min, a solution of ethyl 6-hydroxyhexanoate (20 g, 124.84 mmol) in DCM (90 mL) was added at −78° C. under N$_2$. After 10 min, TEA (75.79 g, 749.01 mmol) was added to the mixture at −78° C. under N$_2$. The reaction mixture was poured into saturated NH$_4$Cl (500 mL) and extracted with MTBE (3×200 mL). The combined organic layer was washed with brine (2×300 mL), dried over anhydrous Na$_2$SO$_4$, filtered, and concentrated under reduced pressure. The residue was purified by silica gel column chromatography (PE:EtOAc=1:0 to 0:1) to give ethyl 6-oxohexanoate (9.8 g, 50%) as a light yellow oil. $^1$H NMR (400 MHz, CDCl$_3$): δ 9.76 (t, J=2 Hz, 1H), 4.10 (q, J=6.8 Hz, 2H), 2.53-2.38 (m, 1H), 2.36-2.21 (m, 2H), 1.66 (td, J=3.2, 6.8 Hz, 4H), 1.48-1.34 (m, 1H), 1.24 (t, J=6.8 Hz, 3H).

Step 2—Ethyl 6,6-difluorohexanoate

To a mixture of ethyl 6-oxohexanoate (9.8 g, 61.32 mmol) in DCM (60 mL) was added BAST (16.28 g, 73.58 mmol) at −78° C. The mixture was stirred at 50° C. for 16 h. The reaction mixture was poured into saturated NaHCO$_3$ (200 mL) at 0° C. and extracted with MTBE (2×100 mL). The combined organic layer was washed with brine (2×100 mL), dried over anhydrous Na$_2$SO$_4$, filtered and concentrated under reduced pressure. The residue was purified by silica gel column chromatography (PE:EtOAc=1:0 to 0:1) to give ethyl 6,6-difluorohexanoate (4.8 g, 43%) as light yellow oil. $^1$H NMR (400 MHz, CDCl$_3$): δ 5.78 (tt, J=4.4 Hz, J=56.8 Hz, 1H), 4.10 (q, J=7.2 Hz, 2H), 2.31 (t, J=7.6 Hz, 2H), 1.93-1.74 (m, 2H), 1.69-1.65 (m, 2H), 1.55-1.42 (m, 2H), 1.24 (t, J=6.8 Hz, 3H).

Step 3—6,6-Difluorohexan-1-ol

To a mixture of ethyl 6,6-difluorohexanoate (2 g, 11.10 mmol) in THF (15 mL) was added LiBH$_4$ (726 mg, 33.30 mmol) at 0° C. under N₂. The mixture was stirred at 15° C. for 32 h. The reaction mixture was poured into saturated NH₄Cl (50 mL) and extracted with MTBE (3×20 mL). The combined organics were washed with brine (2×30 mL), dried over anhydrous Na₂SO₄, filtered, and concentrated under reduced pressure to give 6,6-difluorohexan-1-ol (1.33 g, crude) as a colorless oil. ¹H NMR (400 MHz, CDCl₃): δ 5.78 (tt, J=4.4, 56.8 Hz, 1H), 3.62 (t, J=6.4 Hz, 2H), 1.90-1.71 (m, 2H), 1.67-1.51 (m, 2H), 1.50-1.30 (m, 4H).

Step 4—3-((6,6-Difluorohexyl)oxy)-4-(1-methyl-1,2,5,6-tetrahydropyridin-3-yl)-1,2,5-thiadiazole To a mixture of 6,6-difluorohexan-1-ol (320 mg, 2.32 mmol) in THF (8 mL) was added NaH (278 mg, 6.95 mmol, 60% purity) at 0° C. under N₂. The mixture was stirred at 0° C. for 30 min, and then 3-chloro-4-(1-methyl-1,2,5,6-tetrahydropyridin-3-yl)-1,2,5-thiadiazole (500 mg, 2.32 mmol) was added to the solution at 0° C. under N₂. The mixture was stirred at 50° C. for 16 h. The reaction mixture was poured into saturated NH₄Cl (40 mL) and extracted with MTBE (3×15 mL). The combined organics were washed with brine (2×20 mL), dried over anhydrous Na₂SO₄, filtered and concentrated under reduced pressure. The residue was purified by prep-HPLC (neutral) with the following conditions: column: Kromasil™ C18 (250*50 mm*10 um); mobile phase: [water (10 mM NH₄HCO₃)-ACN]; B %: 55%-85%, 10 min) to give 3-((6,6-difluorohexyl)oxy)-4-(1-methyl-1,2,5,6-tetrahydropyridin-3-yl)-1,2,5-thiadiazole (110 mg, 15%) as white solid. LCMS: m/z=318.2 [M+H]+. ¹H NMR (400 MHz, CDCl₃): δ 7.05-7.03 (m, 1H), 5.82 (tt, J=4.4, 56.4 Hz, 1H), 4.47 (t, J=6.4 Hz, 2H), 3.45 (s, 2H), 2.57 (t, J=5.6 Hz, 2H), 2.51-2.38 (m, 5H), 1.91-1.84 (m, 4H), 1.58-1.54 (m, 4H).

Step 5—5-(4-((6,6-Difluorohexyl)oxy)-1,2,5-thiadiazol-3-yl)-1-methyl-1,2,3,6-tetrahydropyridin-1-ium (2R,3R)-3-carboxy-2,3-dihydroxypropanoate A solution of 3-((6,6-difluorohexyl)oxy)-4-(1-methyl-1,2,5,6-tetrahydropyridin-3-yl)-1,2,5-thiadiazole (110 mg, 0.35 mmol) and (2R,3R)-2,3-dihydroxysuccinic acid (51 mg, 0.34 mmol) in MeOH (6 mL) was stirred at 15° C. for 16 h. The reaction mixture was concentrated under reduced pressure to give 5-(4-((6,6-difluorohexyl)oxy)-1,2,5-thiadiazol-3-yl)-1-methyl-1,2,3,6-tetrahydropyridin-1-ium (2R,3R)-3-carboxy-2,3-dihydroxypropanoate (135 mg, 83%) as light yellow solid. LCMS Method 1: m/z=318.2 [M+H]+, RT=3.281 min (99.424% purity) ¹H NMR (400 MHz, MeOD): δ 7.21 (s, 1H), 5.84 (tt, J=4.4, 56.8 Hz, 1H), 4.48 (t, J=6.4 Hz, 2H), 4.38 (s, 2H), 4.20 (s, 2H), 3.36-3.31 (m, 2H), 2.97 (s, 3H), 2.71-2.68 (m, 2H), 1.87-1.80 (m, 4H), 1.52-1.49 (m, 4H). ¹⁹F NMR (400 MHz, MeOD): δ −117.460.

Example 7—3-((6-Fluorohexyl)oxy)-4-(1-methyl-1,2,5,6-tetrahydropyridin-3-yl)-1,2,5-thiadiazole

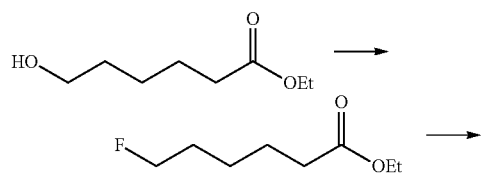

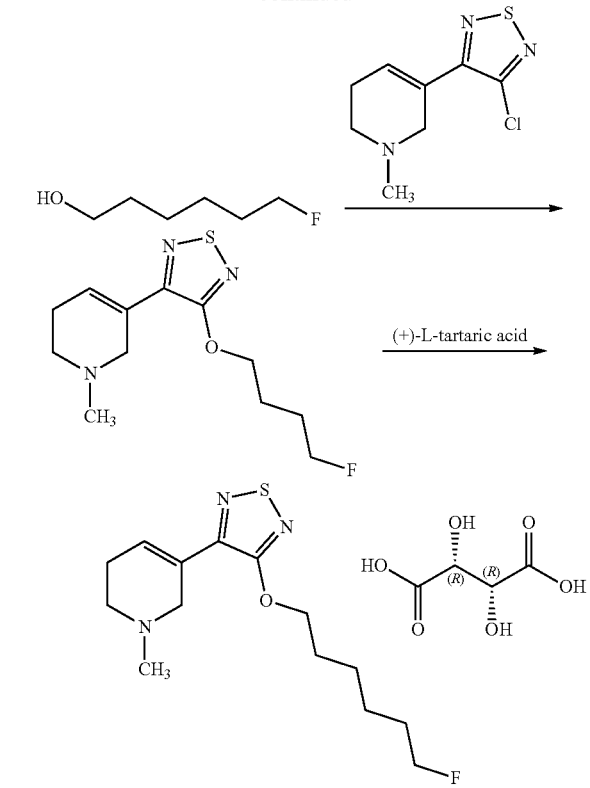

Step 1—Ethyl 6-fluorohexanoate

To a solution of ethyl 6-hydroxyhexanoate (20 g, 124.84 mmol) in DCM (200 mL) was added DAST (20.12 g, 124.84 mmol) at −70° C. under N₂. The mixture was stirred at 25° C. for 12 h. The mixture was poured into sat. NaHCO₃ (300 mL) and then extracted with DCM (3×100 mL). The combined organics were dried over anhydrous Na₂SO₄, filtered, and concentrated under reduced pressure. The residue was purified by silica gel chromatography column (PE:EtOAc=1:0 to 1:1) to give ethyl 6-fluorohexanoate (13.3 g, 66%) as a colorless oil. ¹H NMR (400 MHz, CDCl₃): δ 4.45 (tt, J=6.0, 47.2 Hz, 2H), 4.13 (q, J=7.2 Hz, 2H), 2.32 (t, J=7.6 Hz, 2H), 1.80-1.60 (m, 4H), 1.52-1.39 (m, 2H), 1.26 (t, J=7.2 Hz, 3H).

Step 2—6-Fluorohexan-1-ol

To a solution of ethyl 6-fluorohexanoate (6 g, 36.99 mmol) in THF (60 mL) was added LiBH₄ (1.61 g, 73.98 mmol) in portions at 0° C. under N₂. The mixture was stirred at 0° C. for 2 h and then stirred at 25° C. for 6 h. The reaction mixture was quenched with saturated NH₄Cl (100 ml). The resulting solution was extracted with DCM (3×30 mL). The combined organic phase was dried over anhydrous Na₂SO₄, filtered, and concentrated under reduced pressure to give 6-fluorohexan-1-ol (6 g, crude) as a colorless oil. ¹H NMR (400 MHz, CDCl₃): δ 4.45 (tt, J=6.0, 47.6 Hz, 2H), 3.77-3.63 (m, 2H), 1.91-1.82 (m, 1H), 1.79-1.64 (m, 2H), 1.62-1.53 (m, 2H), 1.50-1.35 (m, 4H).

Step 3—3-((6-Fluorohexyl)oxy)-4-(1-methyl-1,2,5,6-tetrahydropyridin-3-yl)-1,2,5-thiadiazole To a solution of 6-fluorohexan-1-ol (500 mg, 4.16 mmol) in THF (5 mL) was added NaH (999 mg, 24.97 mmol, 60% purity) at 0° C. under N$_2$. The mixture was stirred at 0° C. for 30 min. Then 3-chloro-4-(1-methyl-1,2,5,6-tetrahydropyridin-3-yl)-1,2,5-thiadiazole (898 mg, 4.16 mmol) was added and the mixture was stirred at 50° C. for 12 h. The reaction mixture was quenched with saturated NH$_4$Cl (10 mL). The resulting solution was extracted with DCM (3×5 mL). The combined organic phase was dried over anhydrous Na$_2$SO$_4$, filtered and concentrated under reduced pressure. The crude product was purified by prep-HPLC (neutral) with the following conditions: column: Phenomenex Gemini-NX C18 75*30 mm*3 μm; mobile phase: [water (10 mM NH$_4$HCO$_3$)-ACN]; B %: 50%-70%, 8 min to give 3-((6-fluorohexyl)oxy)-4-(1-methyl-1,2,5,6-tetrahydropyridin-3-yl)-1,2,5-thiadiazole (240 mg, 19%) as brown solid. $^1$H NMR (400 MHz, CDCl$_3$): δ 7.08-7.03 (m, 1H), 4.46 (tt, J=6.0, 47.6 Hz, 2H), 4.46 (t, J=6.4 Hz, 2H), 3.45 (d, J=2.0 Hz, 2H), 2.61-2.54 (m, 2H), 2.49-2.43 (m, 5H), 1.90-1.85 (m, 2H), 1.80-1.65 (m, 2H), 1.55-1.46 (m, 4H).

Step 4—3-((6-Fluorohexyl)oxy)-4-(1-methyl-1,2,5,6-tetrahydropyridin-3-yl)-1,2,5-thiadiazole (2R,3R)-2,3-dihydroxysuccinic acid To a solution of 3-((6-fluorohexyl)oxy)-4-(1-methyl-1,2,5,6-tetrahydropyridin-3-yl)-1,2,5-thiadiazole (125 mg, 0.42 mmol) in MeOH (1 mL) was added a solution of (2R,3R)-2,3-dihydroxysuccinic acid (61.41 mg, 0.41 mmol) in MeOH (3 mL). The mixture was stirred at 25° C. for 12 h. The mixture was concentrated under reduced pressure, then added MTBE (3 mL) and stirred for 20 min. The reaction mixture was filtered and the filter cake was washed with MTBE (3 mL), dried under reduced pressure to give 3-((6-fluorohexyl)oxy)-4-(1-methyl-1,2,5,6-tetrahydropyridin-3-yl)-1,2,5-thiadiazole (2R,3R)-2,3-dihydroxysuccinic acid (60 mg) as white solid. LC-MS: using General Analytical Method 3: m/z: 300.1 [M+H]+, RT=3.245 min (94.00% purity). $^1$H NMR (400 MHz, DMSO): δ 10.02-7.32 (m, 2H), 7.04 (br s, 1H), 4.58-4.32 (m, 4H), 4.16 (s, 2H), 3.52 (br s, 2H), 2.69 (br s, 2H), 2.48-2.38 (m, 5H), 1.82-1.79 (m, 2H), 1.73-1.57 (m, 2H), 1.48-1.43 (m, 4H). $^{19}$F NMR (400 MHz, DMSO): δ −216.793.

Example 8—3-((5,5-Difluorohexyl)oxy)-4-(1-methyl-1,2,5,6-tetrahydropyridin-3-yl)-1,2,5-thiadiazole

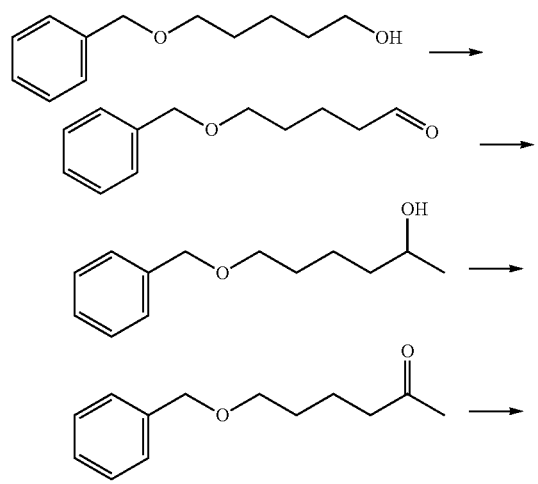

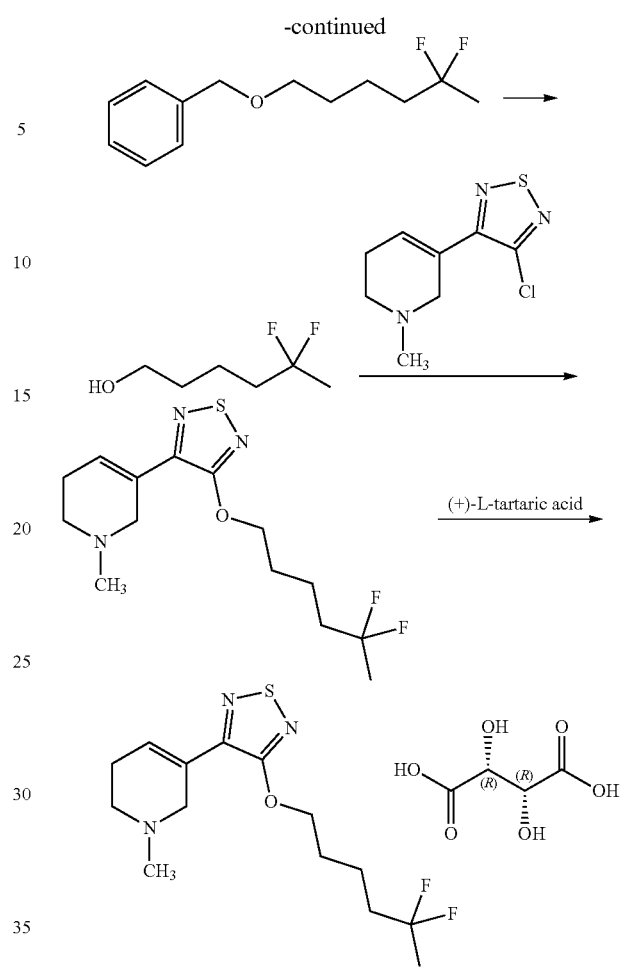

Step 1—5-(Benzyloxy)pentanal

To a solution of 5-(benzyloxy)pentan-1-ol (57 g, 293.41 mmol) in DCM (500 mL) was added DMP (149.34 g, 352.09 mmol). The mixture was stirred at 25° C. for 2 h. The reaction mixture was poured into saturated NaHCO$_3$ (300 mL). The aqueous phase was extracted with DCM (3×200 mL). The organic phase was dried with anhydrous Na$_2$SO$_4$, filtered, and concentrated under reduced pressure. The residue was purified by silica gel chromatography column (PE:EtOAc=20:1 to 1:1) to give 5-(benzyloxy)pentanal (43 g, 76%) as a colorless oil.
$^1$H NMR (400 MHz, CDCl$_3$): δ 9.75 (t, J=1.6 Hz, 1H), 7.30-7.26 (m, 5H), 4.50 (s, 2H), 3.54-3.44 (m, 2H), 2.50-2.39 (m, 2H), 1.80-1.59 (m, 4H).

Step 2—6-(Benzyloxy)hexan-2-ol

To a solution of 5-(benzyloxy)pentanal (30 g, 156.04 mmol) in THF (300 mL) was added MeMgBr (3 M, 130.04 mL) at 0° C. Then the reaction was stirred at 20° C. for 2 h. The reaction mixture was quenched by sat.NH$_4$Cl (400 mL). The aqueous phase was extracted with MTBE (3×200 mL). The combined organic phase was dried with anhydrous Na$_2$SO$_4$, filtered, and concentrated under reduced pressure. The residue was purified by silica gel chromatography column (PE:EtOAc=20:1 to 1:1) to give 6-(benzyloxy)hexan-2-ol (37.5 g, 58%) as a colorless oil.

$^1$H NMR (400 MHz, CDCl$_3$): δ 7.27-7.20 (m, 5H), 4.44 (s, 2H), 3.76-3.66 (m, 1H), 3.41 (t, J=6.4 Hz, 2H), 1.64-1.54 (m, 2H), 1.47-1.30 (m, 4H), 1.13-1.09 (m, 3H).

Step 3—6-(Benzyloxy)hexan-2-one

To a solution of 6-(benzyloxy)hexan-2-ol (18 g, 86.42 mmol) in DCM (200 mL) was added DMP (43.98 g, 103.70 mmol) at 0° C. The mixture was stirred at 25° C. for 4 h. The reaction mixture was poured into sat.Na$_2$S$_2$O$_3$ (200 mL), stirred for 30 min, and then added sat.NaHCO$_3$ (200 mL). The aqueous phase was extracted with MTBE (3×100 mL). The organic phase was dried over anhydrous Na$_2$SO$_4$, filtered, and concentrated under reduced pressure. The residue was purified by silica gel chromatography column (PE:EtOAc=0:1 to 1:1) to give 6-(benzyloxy)hexan-2-one (16.6 g, 47%) as a colorless oil. $^1$H NMR (400 MHz, CDCl$_3$): δ 7.38-7.26 (m, 4H), 4.50 (s, 2H), 3.48 (t, J=6.0 Hz, 2H), 2.46 (t, J=7.2 Hz, 2H), 2.13 (s, 3H), 1.75-1.57 (m, 4H).

Step 4—((5,5-Difluorohexyl)oxy)methyl)benzene

To a solution of 6-(benzyloxy)hexan-2-one (5.5 g, 26.66 mmol) in DCM (40 mL) was added drop-wise DAST (12.89 g, 79.99 mmol) at −70° C. The mixture was stirred at 25° C. for 16 h. The mixture was basified with NaHCO$_3$ till pH=8 and then extracted with DCM (3×30 mL). The combined organic phase was dried over anhydrous Na$_2$SO$_4$, filtered, and concentrated under reduced pressure to give ((5,5-difluorohexyl)oxy)methyl)benzene (20 g, crude) as a brown oil. $^1$H NMR (400 MHz, CDCl$_3$): 7.44-7.27 (m, 4H), 4.50 (s, 2H), 3.48 (t, J=6.0 Hz, 2H), 1.96-1.77 (m, 2H), 1.74-1.47 (m, 7H).

Step 5—5,5-Difluorohexan-1-ol

To a solution of ((5,5-difluorohexyl)oxy)methyl)benzene (1 g, 4.38 mmol) in MeOH (30 mL) was added Pd/C (2 g, 10%) at 25° C. under N$_2$. The suspension was degassed under vacuum and purged three times with H$_2$. The mixture was stirred under 3 Mpa at 100° C. for 12 h in an autoclave. The reaction mixture was filtered, and the filtrate was concentrated under reduced pressure to give 5,5-difluorohexan-1-ol (438 mg, crude) as a brown oil.

Step 6—3-((5,5-Difluorohexyl)oxy)-4-(1-methyl-1,2,5,6-tetrahydropyridin-3-yl)-1,2,5-thiadiazole To a solution of 5,5-difluorohexan-1-ol (220 mg, 1.59 mmol) in THF (10 mL) was added NaH (382 mg, 9.55 mmol, 60% purity) at 0° C. The mixture was stirred at 0° C. for 30 min. 3-chloro-4-(1-methyl-1,2,5,6-tetrahydropyridin-3-yl)-1,2,5-thiadiazole (326 mg, 1.51 mmol) was added and the mixture was stirred at 80° C. for 12 h. The reaction mixture was quenched by sat.NH$_4$Cl (20 mL). The resulting solution was extracted with DCM (6×10 mL). The combined organic phase was dried over anhydrous Na$_2$SO$_4$, filtered and concentrated under reduced pressure. The residue was purified by prep-HPLC (neutral) with the following conditions: column: Kromasil C18 (250*50 mm*10 um); mobile phase: [water (10 mM NH$_4$HCO$_3$)-ACN]; B %: 40%-70%, 10 min to give 3-((5,5-difluorohexyl)oxy)-4-(1-methyl-1,2,5,6-tetrahydropyridin-3-yl)-1,2,5-thiadiazole (90 mg, 18%) as yellow solid. $^1$H NMR (400 MHz, CDCl$_3$): δ 7.05 (br s, 1H), 4.48 (t, J=6.8 Hz, 2H), 3.47 (br d, J=1.6 Hz, 2H), 2.69-2.55 (m, 2H), 2.47 (s, 3H), 1.97-1.85 (m, 4H), 1.68-1.56 (m, 4H), 1.30-1.21 (m, 3H).

Step 7—3-((5,5-Difluorohexyl)oxy)-4-(1-methyl-1,2,5,6-tetrahydropyridin-3-yl)-1,2,5-thiadiazole (2R,3R)-2,3-dihydroxysuccinic acid To a solution of 3-((5,5-difluorohexyl)oxy)-4-(1-methyl-1,2,5,6-tetrahydropyridin-3-yl)-1,2,5-thiadiazole (90 mg, 0.28 mmol) in MeOH (1 mL) was added a solution of (2R,3R)-2,3-dihydroxysuccinic acid (42.13 mg, 0.28 mmol) in MeOH (3 mL). The mixture was stirred at 25° C. for 12 h. The mixture was concentrated under reduced pressure to give 3-((5,5-difluorohexyl)oxy)-4-(1-methyl-1,2,5,6-tetrahydropyridin-3-yl)-1,2,5-thiadiazole (2R,3R)-2,3-dihydroxysuccinic acid (123 mg) as yellow solid. LC-MS Method 2: m/z: 318.1 [M+H]. RT=1.967 min (96.34% purity). $^1$H NMR (400 MHz, DMSO): δ 9.69-7.14 (m, 2H), 7.04 (br s, 1H), 4.46 (t, J=6.4 Hz, 2H), 4.16 (s, 2H), 3.52 (br s, 2H), 2.70 (br t, J=5.6 Hz, 2H), 2.48 (s, 3H), 2.42 (br s, 2H), 2.04-1.77 (m, 4H), 1.64-1.55 (m, 4H), 1.23 (s, 3H). $^{19}$F NMR (400 MHz, DMSO): δ −92.429.

Example 9—3-((4,4-Difluorohexyl)oxy)-4-(1-methyl-1,2,5,6-tetrahydropyridin-3-yl)-1,2,5-thiadiazole

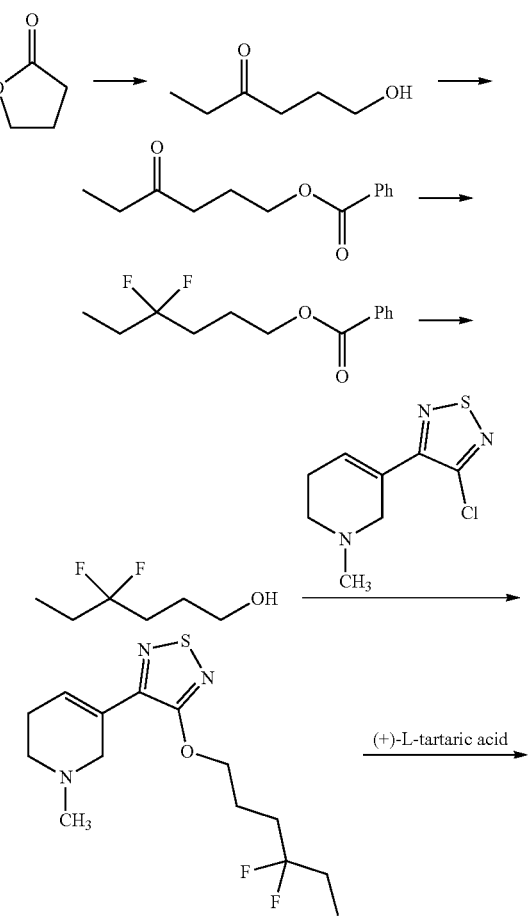

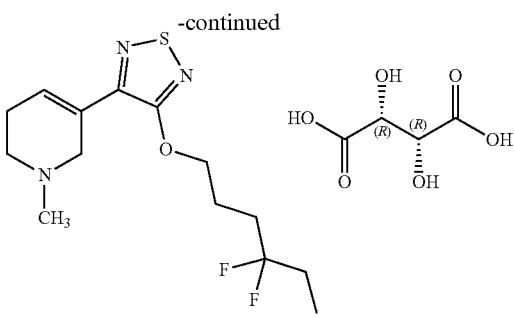

Step 1—6-Hydroxyhexan-3-one

To a solution of tetrahydrofuran-2-one (20 g, 232.32 mmol), NaOMe (3.14 g, 58.08 mmol), and HN(OMe)Me.HCl (27.19 g, 278.78 mmol) in THF (200 mL) was added EtMgBr (3 M, 387 mL) at 0° C. The reaction mixture was stirred at 0° C. for 2 h and then warmed to 20° C. and stirred for 8 h. The mixture was quenched by adding HCl (1 M, 300 mL) at 0° C. and stirred for 2 h. The mixture was concentrated under reduced pressure to remove THF. The aqueous phase was extracted with DCM (3×100 mL). The combined organic phase was washed with brine (200 mL), dried over anhydrous $Na_2SO_4$, filtered, and concentrated under reduced pressure. The residue was purified by silica gel column chromatography (PE:EtOAc=5:1 to 0:1) to give 6-hydroxyhexan-3-one (10.4 g, 39%) as a yellow oil.

Step 2—4-Oxohexyl benzoate

To a solution of 6-hydroxyhexan-3-one (10.4 g, 89.53 mmol) and pyridine (14.16 g, 179.07 mmol) in DCM (100 mL) was dropwise added benzoyl chloride (13.84 g, 98.49 mmol) at 0° C. Then the reaction was stirred at 20° C. for 12 h. The reaction mixture was diluted with $H_2O$ (100 mL) and extracted with DCM (3×100 mL). The combined organic layers were dried over anhydrous $Na_2SO_4$, filtered, and concentrated under reduced pressure. The residue was purified by silica gel column chromatography (PE:EtOAc=10:1 to 4:1) to give 4-oxohexyl benzoate (14 g, 71%) as a yellow oil. $^1$H NMR (400 MHz, CDCl$_3$): δ 8.08-7.99 (m, 2H), 7.60-7.53 (m, 1H), 7.48-7.41 (m, 2H), 4.34 (t, J=6.4 Hz, 2H), 2.58 (t, J=7.2 Hz, 2H), 2.46 (q, J=7.2 Hz, 2H), 2.12-2.06 (m, 2H), 1.07 (t, J=7.6 Hz, 3H).

Step 3—4,4-Difluorohexyl benzoate

To a solution of 4-oxohexyl benzoate (12 g, 54.48 mmol) in DCE (120 mL) was added BAST (24.11 g, 108.96 mmol) at 20° C. Then the reaction was stirred at 90° C. for 12 h. The reaction mixture was poured into saturated NaHCO$_3$ (120 mL) at 20° C. and then extracted with DCM (3×120 mL). The combined organic layers were dried over Na$_2$SO$_4$, filtered, and concentrated under reduced pressure. The residue was purified by silica gel column chromatography (PE:EtOAc=1:0 to 4:1) to give 4,4-difluorohexyl benzoate (8 g, 61%) as a red oil. $^1$H NMR (400 MHz, CDCl$_3$): δ 8.16-7.98 (m, 2H), 7.61-7.54 (m, 1H), 7.49-7.41 (m, 2H), 4.41-4.34 (m, 2H), 2.03-1.81 (m, 6H), 1.04 (t, J=7.6 Hz, 3H).

Step 4—4,4-Difluorohexan-1-ol

To a solution of 4,4-difluorohexyl benzoate (8.6 g, 35.50 mmol) in THF (90 mL) and H$_2$O (30 mL) was added LiOH.H$_2$O (2.23 g, 53.25 mmol) at 20° C. Then the reaction was stirred at 20° C. for 12 h. The reaction mixture was diluted with H$_2$O (10 mL) and extracted with MTBE (3×30 mL). The combined organic layers were dried over Na$_2$SO$_4$, filtered, and concentrated under reduced pressure to give 4,4-difluorohexan-1-ol (4.8 g, 97.87%) as a yellow oil. $^1$H NMR (400 MHz, CDCl$_3$): δ 3.68 (t, J=6.4 Hz, 2H), 1.98-1.73 (m, 7H), 1.01 (t, J=7.6 Hz, 3H).

Step 5—3-((4,4-Difluorohexyl)oxy)-4-(1-methyl-1,2,5,6-tetrahydropyridin-3-yl)-1,2,5-thiadiazole To a solution of 4,4-difluorohexan-1-ol (1 g, 4.34 mmol) in THF (10 mL) was added NaH (1.04 g, 26.06 mmol, 60% purity) at 0° C. Then the reaction was stirred at 0° C. for 0.5 h. Then 3-chloro-4-(1-methyl-3,6-dihydro-2H-pyridin-5-yl)-1,2,5-thiadiazole hydrochloride (1.1 g, 4.34 mmol) was added to the mixture at 20° C. Then the reaction was stirred at 20° C. for 12 h. The reaction mixture was diluted with H$_2$O (5 mL) and extracted with EtOAc (4×10 mL). The combined organic layers were dried over Na$_2$SO$_4$, filtered, and concentrated under reduced pressure. The residue was purified by prep-HPLC (neutral) with the following conditions: column: Kromasil C18 (250*50 mm*10 um); mobile phase: [water (10 mM NH$_4$HCO$_3$)-ACN]; B %: 50%-75%, 10 min to give 3-(4,4-difluorohexoxy)-4-(1-methyl-3,6-dihydro-2H-pyridin-5-yl)-1,2,5-thiadiazole (400 mg, 29%) as red oil.

$^1$H NMR (400 mhz, DMSO-d6): δ 7.32-6.37 (m, 1H), 4.46-4.44 (m, 2H), 3.27 (s, 2H), 2.46 (t, J=5.6 Hz, 2H), 2.41-2.25 (m, 5H), 2.12-1.74 (m, 6H), 0.94 (t, J=7.6 Hz, 3H).

Step 6—3-((4,4-Difluorohexyl)oxy)-4-(1-methyl-1,2,5,6-tetrahydropyridin-3-yl)-1,2,5-thiadiazole (2R, 3R)-2,3-dihydroxysuccinate To a solution of 3-(4,4-difluorohexoxy)-4-(1-methyl-3,6-dihydro-2H-pyridin-5-yl)-1,2,5-thiadiazole (300 mg, 0.94 mmol) in MeOH (2 ml) was added a solution of (2R,3R)-2,3-dihydroxybutanedioic acid (139.02 mg, 0.92 mmol) in MeOH (2 mL) at 25° C. The mixture was stirred at 25° C. for 12 h. The mixture was concentrated under reduced pressure then triturated with MTBE (3 mL). The mixture was filtered and the filter cake was washed with MTBE (3 mL), dried under reduced pressure to give 3-(4,4-difluorohexoxy)-4-(1-methyl-3,6-dihydro-2H-pyridin-5-yl)-1,2,5-thiadiazole (2R,3R)-2,3-dihydroxysuccinic acid (300 mg) as yellow solid. LC-MS (m/z): 318 [M+H]+, RT=3.203 min (96.28% purity). $^1$H NMR (400 MHz, DMSO): δ 9.34-7.16 (m, 2H), 7.04 (br t, J=4.0 Hz, 1H), 4.48 (t, J=6.4 Hz, 2H), 4.17 (s, 2H), 3.55 (br d, J=1.6 Hz, 2H), 2.73 (t, J=5.6 Hz, 2H), 2.53-2.50 (m, 3H), 2.44 (br d, J=3.6 Hz, 2H), 2.07-1.85 (m, 6H), 0.95 (t, J=7.6 Hz, 3H). $^{19}$F NMR (400 MHz, DMSO): δ −98.343.

Example 10—3-((3,3-Difluorohexyl)oxy)-4-(1-methyl-1,2,5,6-tetrahydropyridin-3-yl)-1,2,5-thiadiazole

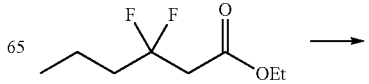

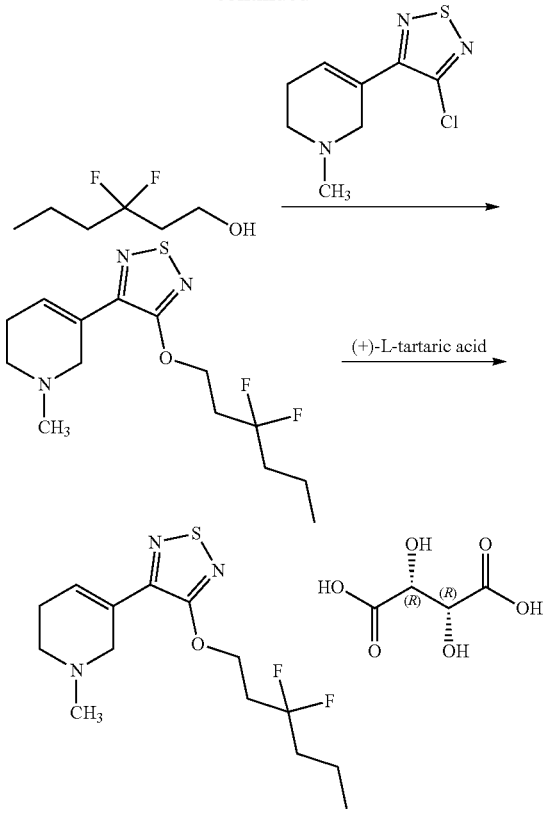

3-((3,3-difluorohexyl)oxy)-4-(1-methyl-1,2,5,6-tetrahydropyridin-3-yl)-1,2,5-thiadiazole (120 mg, 58%) as light yellow solid.

$^1$H NMR (400 MHz, CDCl$_3$): δ 7.04 (m, 1H), 4.66 (t, J=6.4 Hz, 2H), 3.45 (d, J=2.0 Hz, 2H), 2.60-2.54 (t, J=6.0 Hz, 2H), 2.50-2.36 (m, 7H), 1.99-1.79 (m, 2H), 1.61-1.48 (m, 2H), 0.98 (t, J=7.6 Hz, 3H).

Step 3—5-(4-((3,3-Difluorohexyl)oxy)-1,2,5-thiadiazol-3-yl)-1-methyl-1,2,3,6-tetrahydropyridin-1-ium (2R,3R)-3-carboxy-2,3-dihydroxypropanoate To a solution of 3-((3,3-difluorohexyl)oxy)-4-(1-methyl-1,2,5,6-tetrahydropyridin-3-yl)-1,2,5-thiadiazole (63 mg, 0.20 mmol) in MeOH (1 mL) was added (2R,3R)-2,3-dihydroxybutanedioic acid (30 mg, 0.20 mmol) at 15° C. and the mixture was stirred at 15° C. for 0.5 h. The mixture was concentrated under reduced pressure to give 5-(4-((3,3-difluorohexyl)oxy)-1,2,5-thiadiazol-3-yl)-1-methyl-1,2,3,6-tetrahydropyridin-1-ium (2R,3R)-3-carboxy-2,3-dihydroxypropanoate (90 mg, 98%) as yellow solid. LCMS Method 2: m/z=318.1 [M+H]+, RT=1.976 min (97.90% purity). $^1$H NMR (400 MHz, MeOD): δ 7.26 (s, 1H), 4.69 (t, J=6.4 Hz, 2H), 4.39 (s, 2H), 4.21 (s, 2H), 3.38 (t, J=6.0 Hz, 2H), 2.99 (s, 3H), 2.74 (s, 2H), 2.48 (m, 2H), 2.02-1.82 (m, 2H), 0.99 (t, J=7.6 Hz, 3H). $^{19}$F NMR (400 MHz, MeOD): δ −98.742.

Example 11—3-((2,2-Difluorohexyl)oxy)-4-(1-methyl-1,2,5,6-tetrahydropyridin-3-yl)-1,2,5-thiadiazole Step 1—3,3-Difluorohexan-1-ol To a mixture of ethyl 3,3-difluorohexanoate (500 mg, 3 mmol) in THF (15 mL) was added LAH (158 mg, 4.15 mmol) at 0° C. under N$_2$. The mixture was stirred at 15° C. for 3 h. The Na$_2$SO$_4$.10H$_2$O was added to the reaction mixture at 15° C. for 10 min, and the reaction mixture was dried over anhydrous Na$_2$SO$_4$. Then the reaction mixture was filtered through a pad of celite, and the filtrate was concentrated under reduced pressure to give 3,3-difluorohexan-1-ol (280 mg, crude) as a light yellow oil. $^1$H NMR (400 MHz, CDCl$_3$): δ 3.86 (t, J=6.4 Hz, 2H), 2.16-2.10 (m, 2H), 1.91-1.78 (m, 3H), 1.62-1.45 (m, 2H), 0.97 (t, J=7.2 Hz, 3H).

Step 2—3-((3,3-Difluorohexyl)oxy)-4-(1-methyl-1,2,5,6-tetrahydropyridin-3-yl)-1,2,5-thiadiazole To a mixture of 3,3-difluorohexan-1-ol (90 mg, 0.65 mmol) in THF (3 mL) was added NaH (78 mg, 1.95 mmol, 60% purity) at 0° C. under N$_2$. The mixture was stirred at 0° C. for 30 min. Then 3-chloro-4-(1-methyl-1,2,5,6-tetrahydropyridin-3-yl)-1,2,5-thiadiazole (141 mg, 0.65 mmol) was added at 15° C. and the mixture was stirred at 50° C. for 16 h. The reaction mixture was poured into saturated NH$_4$Cl (10 mL) and extracted with MTBE (2×10 mL). The combined organic layer was washed with brine (2×10 mL), dried over anhydrous Na$_2$SO$_4$, filtered and concentrated under reduced pressure. The residue was purified by prep-HPLC (neutral) with the following conditions: column: Waters Xbridge BEH C18 100*25 mm*5 μm; mobile phase: [water (10 mM NH$_4$HCO$_3$)-ACN]; B %: 75%-95%, 10 min) to give

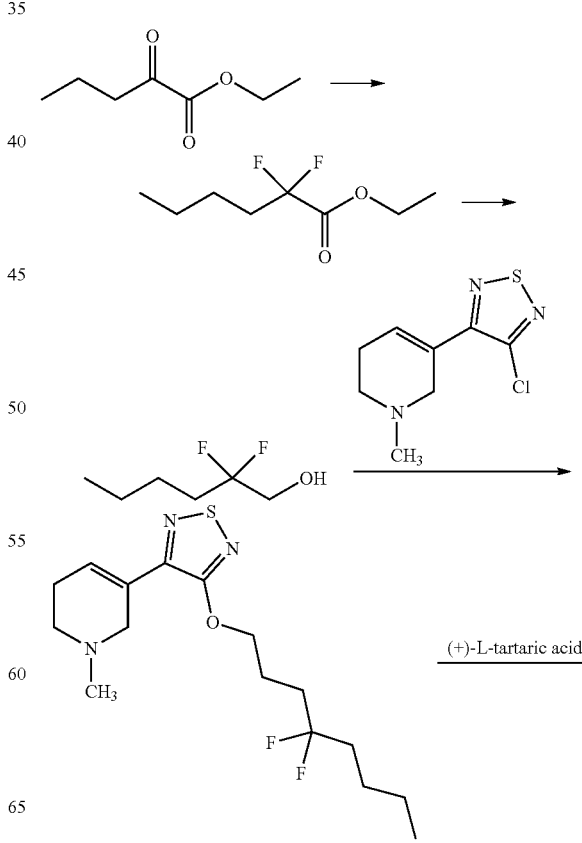

-continued

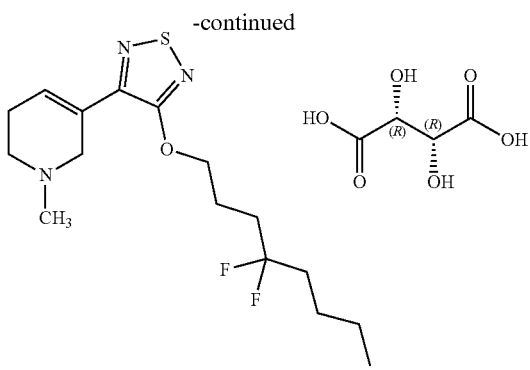

Step 1—Ethyl 2,2-difluorohexanoate

To a mixture of ethyl 2-oxopentanoate (10 g, 63.21 mmol) in DCM (100 mL) was added drop-wise DAST (12.23 g, 75.86 mmol) at 0° C. under $N_2$. The mixture was stirred at 25° C. for 16 h. The reaction mixture was poured into saturated $NaHCO_3$ (400 mL) and extracted with MTBE (2×200 mL). The combined organic layer was washed with brine (2×100 mL), dried over anhydrous $Na_2SO_4$, filtered, and concentrated under reduced pressure to give ethyl 2,2-difluorohexanoate (11 g, crude) as a brown oil. $^1$H NMR (400 MHz, $CDCl_3$): δ 4.32 (q, J=7.2 Hz, 2H), 2.12-1.96 (m, 2H), 1.50-1.27 (m, 7H), 0.91 (t, J=7.2 Hz, 3H).

Step 2—2,2-Difluorohexan-1-ol

To a solution of ethyl 2,2-difluorohexanoate (11 g, 61.05 mmol) in THF (100 mL) was added $LiBH_4$ (1.33 g, 61.05 mmol) at 0° C. under $N_2$. The mixture was stirred at 0° C. for 2 h. The reaction mixture was poured into sat. $NH_4Cl$ (100 mL) and extracted with MTBE (3×40 mL). The combined organic layer was washed with brine (2×40 mL), dried over anhydrous $Na_2SO_4$, filtered, and concentrated under reduced pressure to give 2,2-difluorohexan-1-ol (7 g, crude) as a brown liquid. $^1$H NMR (400 MHz, $CDCl_3$): δ 3.72 (t, J=12.8 Hz, 2H), 2.98-2.49 (m, 1H), 1.99-1.81 (m, 2H), 1.55-1.30 (m, 4H), 0.99-0.86 (t, J=7.2 Hz, 3H).

Step 3—3-((2,2-Difluorohexyl)oxy)-4-(1-methyl-1,2,5,6-tetrahydropyridin-3-yl)-1,2,5-thiadiazole To a mixture of 2,2-difluorohexan-1-ol (320 mg, 2.32 mmol) in THF (15 mL) was added NaH (278 mg, 6.96 mmol, 60% purity) at 0° C. under $N_2$. The mixture was stirred at 0° C. for 20 min, then 3-chloro-4-(1-methyl-1,2,5,6-tetrahydropyridin-3-yl)-1,2,5-thiadiazole (500 mg, 2.32 mmol) was added. The mixture was stirred at 80° C. for 16 h. The reaction mixture was poured into sat. $NH_4Cl$ (40 mL) and extracted with MTBE (2×20 mL). The combined organic layer was washed with brine (2×20 mL), dried over anhydrous $Na_2SO_4$, filtered and concentrated under reduced pressure. The residue was purified by prep-HPLC (neutral) with the following conditions: column: Kromasil C18 (250 mm*50 mm*10 μm); mobile phase: [water (10 mM $NH_4HCO_3$)-ACN]; B %: 55%-85%, 10 min) to give 3-((2,2-difluorohexyl)oxy)-4-(1-methyl-1,2,5,6-tetrahydropyridin-3-yl)-1,2,5-thiadiazole as colorless solid. LCMS: m/z=318.02 [M+H]+. $^1$H NMR (400 MHz, $CDCl_3$): δ 7.02 (s, 1H), 4.62 (t, J=12 Hz, 2H), 3.45 (s, 2H), 2.65-2.52 (m, 2H), 2.47 (s, 5H), 2.11-1.88 (m, 2H), 1.63-1.46 (m, 2H), 1.42-1.36 (m, 2H), 0.94 (t, J=7.2 Hz, 3H).

Step 4—3-((2,2-Difluorohexyl)oxy)-4-(1-methyl-1,2,5,6-tetrahydropyridin-3-yl)-1,2,5-thiadiazole (2R,3R)-2,3-dihydroxysuccinic acid To a mixture of 3-((2,2-difluorohexyl)oxy)-4-(1-methyl-1,2,5,6-tetrahydropyridin-3-yl)-1,2,5-thiadiazole (75 mg, 0.24 mmol) in MeOH (5 mL) was added (2R,3R)-2,3-dihydroxysuccinic acid (35.46 mg, 0.24 mmol) at 15° C. The mixture was stirred at 15° C. for 16 h. The reaction mixture was concentrated under reduced pressure to give 3-((2,2-difluorohexyl)oxy)-4-(1-methyl-1,2,5,6-tetrahydropyridin-3-yl)-1,2,5-thiadiazole (2R,3R)-2,3-dihydroxysuccinic acid (100 mg) as white solid. LCMS Method 1: m/z=318.2 [M+H]+, RT=3.358 min (99.86% purity). $^1$H NMR (400 MHz, MeOD): δ 7.20 (s, 1H), 4.75 (t, J=12.8 Hz, 2H), 4.41 (s, 2H), 4.18 (s, 2H), 3.38-3.32 (m, J=5.2 Hz, 2H), 2.97 (s, 3H), 2.73 (d, J=3.6 Hz, 2H), 2.11-1.95 (m, 2H), 1.61-1.48 (m, 2H), 1.41 (qd, J=7.6 Hz, 22.4 Hz, 36.4 Hz, 2H), 0.95 (t, J=7.2 Hz, 3H). $^{19}$F NMR (400 MHz, MeOD): δ −107.834.

Example 12—3-((1,1-Difluorohexyl)oxy)-4-(1-methyl-1,2,5,6-tetrahydropyridin-3-yl)-1,2,5-thiadiazole

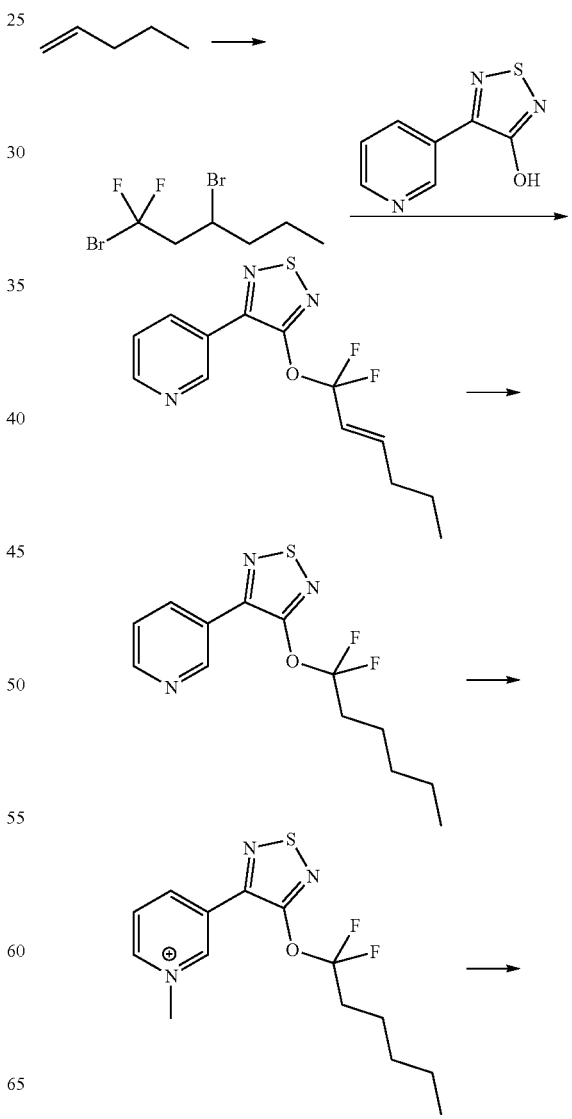

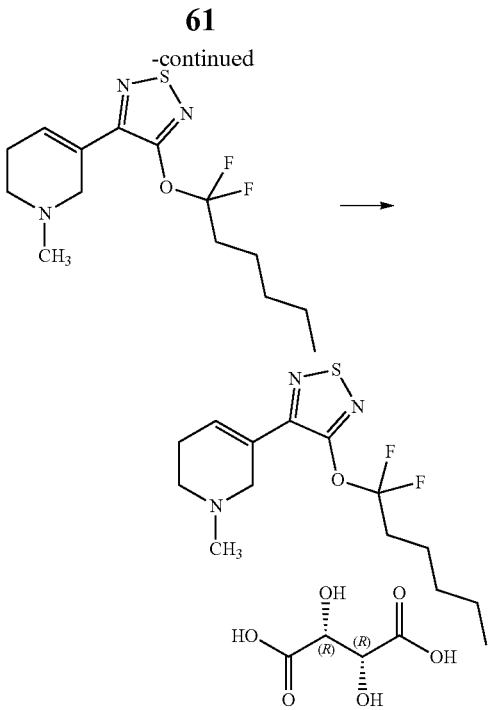

Step 1—1,3-Dibromo-1,1-difluorohexane

To a solution of dibromo(difluoro)methane (20 g, 95.32 mmol), pent-1-ene (10.03 g, 142.98 mmol) and NaHCO$_3$ (12.81 g, 152.51 mmol) in MeCN (200 mL) and H$_2$O (50 mL) was added sodium hydrosulfite (29.87 g, 171.58 mmol) and the mixture was stirred at 25° C. for 16 h. The reaction mixture was filtered, and the filtrate was poured into H$_2$O (300 mL), extracted with MTBE (2×100 mL), and the combined organic layers were washed with brine (200 mL), dried over Na$_2$SO$_4$, filtered, and concentrated under reduced pressure to give 1,3-dibromo-1,1-difluorohexane (15 g, 56%) as a yellow oil.

Step 2—(E)-3-((1,1-Difluorohex-2-en-1-yl)oxy)-4-(pyridin-3-yl)-1,2,5-thiadiazole To a solution of 4-(pyridin-3-yl)-1,2,5-thiadiazol-3-ol (2 g, 11.16 mmol) in DMF (20 mL) was added Cs$_2$CO$_3$ (7.27 g, 22.32 mmol) and 1,3-dibromo-1,1-difluorohexane (6.25 g, 22.32 mmol) at 20° C. Then the reaction was stirred at 50° C. for 12 h. The reaction mixture was diluted with H$_2$O (60 mL) and extracted with EtOAc (4×40 mL). The combined organic layers were dried over Na$_2$SO$_4$, filtered and concentrated under reduced pressure. The residue was purified by silica gel column chromatography (PE:EtOAc=1:0 to 1:1) to give (E)-3-((1,1-difluorohex-2-en-1-yl)oxy)-4-(pyridin-3-yl)-1,2,5-thiadiazole (2.3 g, 7.74 mmol) as a yellow oil. $^1$H NMR (400 MHz, CDCl$_3$): δ 9.31 (d, J=2.4 Hz, 1H), 8.71 (dd, J=1.6, 4.8 Hz, 1H), 8.35 (td, J=2.0, 8.0 Hz, 1H), 7.43 (dd, J=4.8, 8.2 Hz, 1H), 6.71-6.29 (m, 1H), 5.98-5.78 (m, 1H), 2.30-2.09 (m, 2H), 1.53-1.45 (m, 2H), 0.93 (t, J=7.2 Hz, 3H)

Step 3—3-((1,1-Difluorohexyl)oxy)-4-(pyridin-3-yl)-1,2,5-thiadiazole

To a solution of (E)-3-((1,1-difluorohex-2-en-1-yl)oxy)-4-(pyridin-3-yl)-1,2,5-thiadiazole (2 g, 6.73 mmol) in MeOH (60 mL) was added Pd/C (20 g, 6.73 mmol, 10% purity) under N$_2$. The suspension was degassed under vacuum and purged three times with H$_2$. Then the reaction was stirred under H$_2$ (50 psi) at 50° C. for 24 h. The suspension was filtered through a pad of Celite, and the filter cake was washed with MeOH (2×30 mL). The combined filtrates were concentrated under reduced pressure to give 3-((1,1-difluorohexyl)oxy)-4-(pyridin-3-yl)-1,2,5-thiadiazole (2 g, crude) as a yellow oil.

Step 4—3-(4-((1,1-Difluorohexyl)oxy)-1,2,5-thiadiazol-3-yl)-1-methylpyridin-1-ium To a solution of 3-((1,1-difluorohexyl)oxy)-4-(pyridin-3-yl)-1,2,5-thiadiazole (2 g, 6.68 mmol) in acetone (20 mL) was added CH$_3$I (3.79 g, 26.73 mmol) at 20° C. Then the reaction was stirred at 30° C. for 12 h. The reaction was concentrated under reduced pressure to give 3-(4-((1,1-difluorohexyl)oxy)-1,2,5-thiadiazol-3-yl)-1-methylpyridin-1-ium (2.9 g, crude) as yellow oil.

Step 5—3-((1,1-Difluorohexyl)oxy)-4-(1-methyl-1,2,5,6-tetrahydropyridin-3-yl)-1,2,5-thiadiazole To a mixture of 3-(4-((1,1-difluorohexyl)oxy)-1,2,5-thiadiazol-3-yl)-1-methylpyridin-1-ium (1 g, 2.27 mmol) in MeOH (10 mL) was added CaCl$_2$) (503 mg, 4.53 mmol) and NaBH$_4$ (343 mg, 9.06 mmol) at 0° C. under N$_2$ over 1 h. The mixture was stirred at 20° C. for 2 h. The reaction mixture was diluted with H$_2$O (10 mL) and extracted with EtOAc (5×10 mL). The combined organic layers were dried over Na$_2$SO$_4$, filtered and concentrated under reduced pressure. The residue was purified by prep-HPLC (neutral) with the following conditions: column: Phenomenex Gemini NX-C18 (75*30 mm*3 um); mobile phase: [water (10 mM NH$_4$HCO$_3$)-ACN]; B %: 55%-75%, 10 min to give 3-((1,1-difluorohexyl)oxy)-4-(1-methyl-1,2,5,6-tetrahydropyridin-3-yl)-1,2,5-thiadiazole (88.40 mg, 24%). LC-MS: m/z: 318.0[M+H]+. $^1$H NMR (400 MHz, CDCl$_3$): δ 6.91 (td, J=2.0, 3.6 Hz, 1H), 3.44 (br d, J=2.0 Hz, 2H), 2.62-2.56 (m, 2H), 2.47 (s, 5H), 2.41-2.29 (m, 2H), 1.64-1.56 (m, 2H), 1.43-1.30 (m, 4H), 0.98-0.88 (m, 3H).

Step 6—3-((1,1-Difluorohexyl)oxy)-4-(1-methyl-1,2,5,6-tetrahydropyridin-3-yl)-1,2,5-thiadiazole (2R,3R)-2,3-dihydroxysuccinate To a mixture of 3-((1,1-difluorohexyl)oxy)-4-(1-methyl-1,2,5,6-tetrahydropyridin-3-yl)-1,2,5-thiadiazole (88 mg, 0.28 mmol) in MeOH (10 mL) was added (2R,3R)-2,3-dihydroxybutanedioic acid (41 mg, 0.28 mmol) at 25° C. The mixture was stirred for 16 h at 25° C. The residue was concentrated under reduced pressure to give 3-((1,1-difluorohexyl)oxy)-4-(1-methyl-1,2,5,6-tetrahydropyridin-3-yl)-1,2,5-thiadiazole (2R,3R)-2,3-dihydroxysuccinate (105.9 mg, 81%) as yellow solid. LC-MS Method 2: m/z: 318.1 [M+H]+, RT=2.206 min (99.245% purity). $^1$H NMR (400 MHz, MeOD): δ 7.10 (s, 1H), 4.41 (s, 2H), 4.20 (br s, 2H), 3.36 (d, J=5.2 Hz, 2H), 2.98 (s, 3H), 2.76-2.74 (m, 2H), 2.47-2.41 (m, 2H), 1.62-1.58 (m, 2H), 1.41-1.35 (m, 4H), 0.92 (t, J=7.2 Hz, 3H). $^{19}$F NMR (400 MHz, MeOD): δ −72.740.

Example 61—3-((Hexyl-1,1,2,2,3,3,4,4,5,5,6,6,6-d$_{13}$)oxy)-4-(1-methyl-1,2,5,6-tetrahydropyridin-3-yl)-1,2,5-thiadiazole (8)

The title compound was prepared by the method described in Scheme 1. $^1$H-NMR (400 MHz, DMSO-d$_6$)

δ:2.35 (m, 2H), 2.5 (s, 3H), 2.7 (m, 2H), 3.5 (m, 2H), 4.2 (s, 2H), 7.1 (m, 1H). MS: m/z calcd. for $C_{14}H_{10}D_{13}N_3OS$ (M+1): 295.42, found 295.5.

Example 62—3-((Hexyl-1,1,2,2,3,3,4,4,5,5,6,6,6-$d_{13}$)oxy)-4-(1-(methyl-d)-1,2,5,6-tetrahydropyridin-3-yl)-1,2,5-thiadiazole (10)

The title compound was prepared by the method described in Scheme 1. $^1$H-NMR (400 MHz, DMSO-$d_6$) δ: 2.4 (m, 2H), 2.8 (m, 2H), 3.6 (m, 2H), 4.2 (s, 2H), 7.1 (m, 1H). MS: m/z calcd. for $C_{14}H_7D_{16}N_3OS$ (M+1): 298.42, found 298.4.

Example 63—3-(1-(Methyl-$d_3$)-1,2,5,6-tetrahydro-pyridin-3-yl)-4-((6,6,6-trifluorohexyl)oxy)-1,2,5-thiadiazole

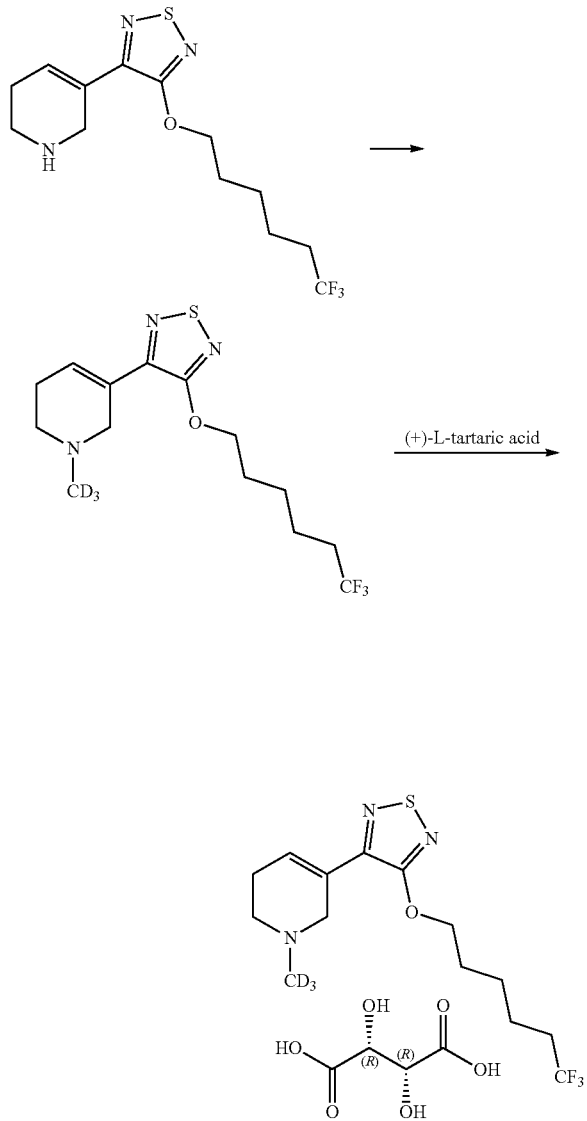

Step 1—3-[1-(Methyl-$d_3$)-3,6-dihydro-2H-pyridin-5-yl]-4-(6,6,6-trifluorohexoxy)-1,2,5-thiadiazole To a solution of 3-(1,2,5,6-tetrahydropyridin-3-yl)-4-((6,6,6-trifluorohexyl)oxy)-1,2,5-thiadiazole hydrochloride (Example 1, 300 mg, 0.84 mmol) and TEA (170 mg, 1.68 mmol) in MeCN (4 mL) was added trideuterio(iodo)methane (119 mg, 0.84 mmol) and the mixture was stirred at 25° C. for 2 h. The mixture was poured into H$_2$O (10 mL), extracted with EtOAc (2×5 mL). The combined organic layers were washed with brine (10 mL), dried over Na$_2$SO$_4$, filtered and concentrated under reduced pressure. The residue was purified by prep-HPLC (neutral) with the following conditions: column: Waters Xbridge BEH C18 100*30 mm*0 μm; mobile phase: [water (10 mM NH$_4$HCO$_3$)-ACN]; B %: 40%-70%, 8 min to give 3-[1-(trideuteriomethyl)-3,6-dihydro-2H-pyridin-5-yl]-4-(6,6,6-trifluorohexoxy)-1,2,5-thiadiazole (25 mg) as white solid. $^1$H NMR (400 MHz, CDCl$_3$): δ 7.03 (br s, 1H), 4.47 (t, J=6.4 Hz, 2H), 3.45 (br d, J=1.6 Hz, 2H), 2.62-2.52 (m, 2H), 2.47-2.44 (m, 2H), 2.19-2.04 (m, 2H), 1.90-1.87 (m, 2H), 1.72-1.61 (m, 2H), 1.61-1.51 (m, 2H).

Step 2—3-[1-(Methyl-$d_3$)-3,6-dihydro-2H-pyridin-5-yl]-4-(6,6,6-trifluorohexoxy)-1,2,5-thiadiazole (2R,3R)-2,3-dihydroxybutanedioic acid To a mixture of 3-[1-(trideuteriomethyl)-3,6-dihydro-2H-pyridin-5-yl]-4-(6,6,6-trifluorohexoxy)-1,2,5-thiadiazole (22 mg, 0.065 mmol) in MeOH (2 mL) was added (2S,3S)-2,3-dihydroxybutanedioic acid (10 mg, 0.065 mmol) at 25° C. The mixture was stirred for 16 at 25° C. The residue was concentrated under reduced pressure to give 3-[1-(methyl-$d_3$)-3,6-dihydro-2H-pyridin-5-yl]-4-(6,6,6-trifluorohexoxy)-1,2,5-thiadiazole(2R,3R)-2,3-dihydroxybutane-dioicacid (30.9 mg, 97%) as white solid. LCMS Method 2: m/z: 339.1 [M+H]+, RT=2.115 min (99.41% purity), deuterium incorporation: 99.3%. $^1$H NMR (400 MHz, MeOD): δ7.24 (br s, 1H), 4.53 (t, J=6.5 Hz, 2H), 4.41 (s, 2H), 4.22 (br s, 2H), 3.38 (br s, 2H), 2.75-2.72 (m, 2H), 2.32-2.10 (m, 2H), 1.98-1.83 (m, 2H), 1.73-1.49 (m, 4H). $^{19}$F NMR (400 MHz, MeOD): δ −67.839.

Compounds 1-3, 6-12, and 61-63 in Table 1 have been made or prepared using the above methods. The other compounds in Table 1 can be prepared by the methods set forth above.

TABLE 1

| Ex. No. | Structure | IUPAC Name | Chemical Formula | MW (g/mol) |
|---|---|---|---|---|
| 1 | 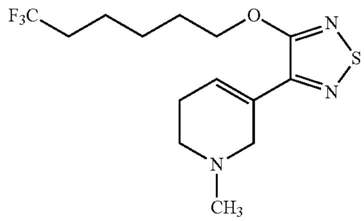 [SMILES: CN1CCC=C(c2nsnc2OCCCCCC(F)(F)F)C1] | 3-(1-methyl-1,2,5,6-tetrahydropyridin-3-yl)-4-((6,6,6-trifluorohexyl)oxy)-1,2,5-thiadiazole | $C_{14}H_{20}F_3N_3OS$ | 335.13 |
| 2 | 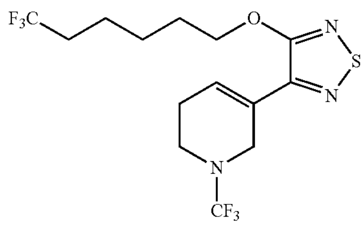 | 3-((6,6,6-trifluorohexyl)oxy)-4-(1-(trifluoromethyl)-1,2,5,6-tetrahydropyridin-3-yl)-1,2,5-thiadiazole | $C_{14}H_{17}F_6N_3OS$ | 389.36 |
| 3 | 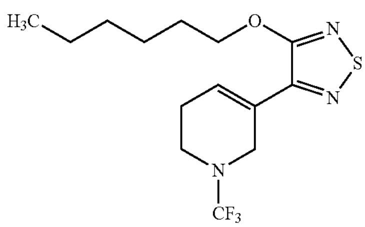 [SMILES: CCCCCCOc1nsnc1C1=CCCN(C(F)(F)F)C1] | 3-(hexyloxy)-4-(1-(trifluoromethyl)-1,2,5,6-tetrahydropyridin-3-yl)-1,2,5-thiadiazole | $C_{14}H_{20}F_3N_3OS$ | 335.39 |
| 4 | 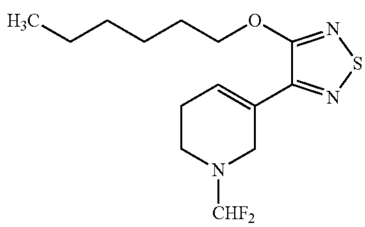 | 3-(1-(difluoromethyl)-1,2,5,6-tetrahydropyridin-3-yl)-4-(hexyloxy)-1,2,5-thiadiazole | $C_{14}H_{21}F_2N_3OS$ | 317.40 |
| 5 | 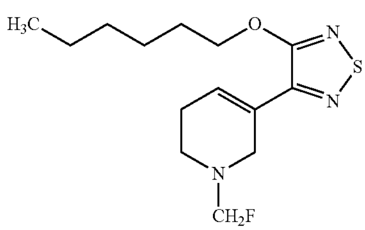 | 3-(1-(fluoromethyl)-1,2,5,6-tetrahydropyridin-3-yl)-4-(hexyloxy)-1,2,5-thiadiazole | $C_{14}H_{22}FN_3OS$ | 299.41 |
| 6 | 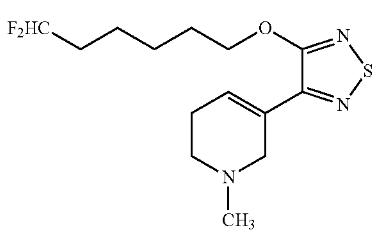 | 3-((6,6-difluorohexyl)oxy)-4-(1-methyl-1,2,5,6-tetrahydropyridin-3-yl)-1,2,5-thiadiazole | $C_{14}H_{21}F_2N_3OS$ | 317.40 |

TABLE 1-continued

Exemplary Compounds

| Ex. No. | Structure | IUPAC Name | Chemical Formula | MW (g/mol) |
|---|---|---|---|---|
| 7 | 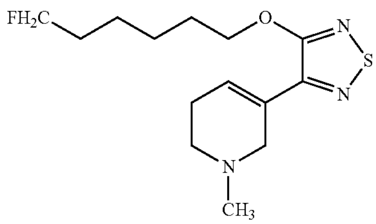 | 3-((6-fluorohexyl)oxy)-4-(1-methyl-1,2,5,6-tetrahydropyridin-3-yl)-1,2,5-thiadiazole | $C_{14}H_{22}FN_3OS$ | 299.41 |
| 8 | 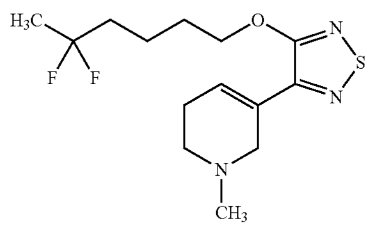 [SMILES: CN1CCC=C(c2nsnc2OCCCCC(C)(F)F)C1] | 3-((5,5-difluorohexyl)oxy)-4-(1-methyl-1,2,5,6-tetrahydropyridin-3-yl)-1,2,5-thiadiazole | $C_{14}H_{21}F_2N_3OS$ | 317.40 |
| 9 | 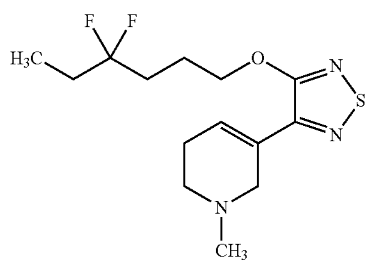 [SMILES: CCC(F)(F)CCCOc1nsnc1C1=CCCN(C)C1] | 3-((4,4-difluorohexyl)oxy)-4-(1-methyl-1,2,5,6-tetrahydropyridin-3-yl)-1,2,5-thiadiazole | $C_{14}H_{21}F_2N_3OS$ | 317.40 |
| 10 | 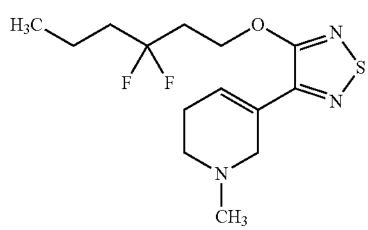 [SMILES: CCCC(F)(F)CCOc1nsnc1C1=CCCN(C)C1] | 3-((3,3-ifluorohexyl)oxy)-4-(1-methyl-1,2,5,6-tetrahydropyridin-3-yl)-1,2,5-thiadiazole | $C_{14}H_{21}F_2N_3OS$ | 317.40 |
| 11 | 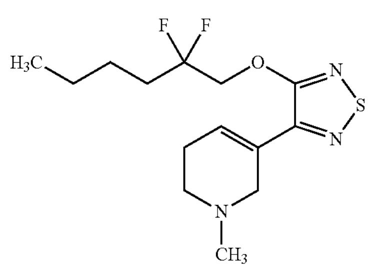 [SMILES: CCCCC(F)(F)COc1nsnc1C1=CCCN(C)C1] | 3-((2,2-difluorohexyl)oxy)-4-(1-methyl-1,2,5,6-tetrahydropyridin-3-yl)-1,2,5-thiadiazole | $C_{14}H_{21}F_2N_3OS$ | 317.40 |
| 12 | 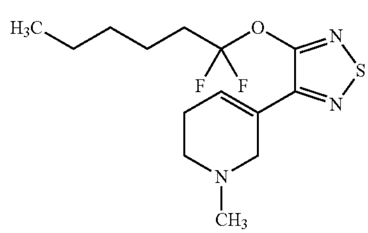 [SMILES: CCCCCC(F)(F)Oc1nsnc1C1=CCCN(C)C1] | 3-((1,1-difluorohexyl)oxy)-4-(1-methyl-1,2,5,6-tetrahydropyridin-3-yl)-1,2,5-thiadiazole | $C_{14}H_{21}F_2N_3OS$ | 317.40 |

TABLE 1-continued

Exemplary Compounds

| Ex. No. | Structure | IUPAC Name | Chemical Formula | MW (g/mol) |
|---|---|---|---|---|
| 13 | 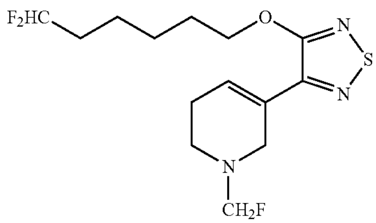 | 3-((6,6-difluorohexyl)oxy)-4-(1-(fluoromethyl)-1,2,5,6-tetrahydropyridin-3-yl)-1,2,5-thiadiazole | $C_{14}H_{20}F_3N_3OS$ | 335.39 |
| 14 | 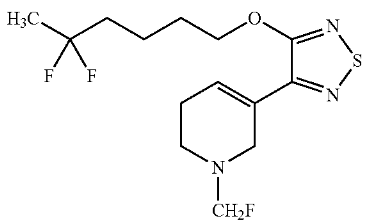 | 3-((5,5-difluorohexyl)oxy)-4-(1-(fluoromethyl)-1,2,5,6-tetrahydropyridin-3-yl)-1,2,5-thiadiazole | $C_{14}H_{20}F_3N_3OS$ | 335.39 |
| 15 | 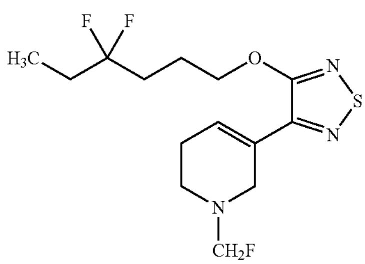 | 3-((4,4-difluorohexyl)oxy)-4-(1-(fluoromethyl)-1,2,5,6-tetrahydropyridin-3-yl)-1,2,5-thiadiazole | $C_{14}H_{20}F_3N_3OS$ | 335.39 |
| 16 | 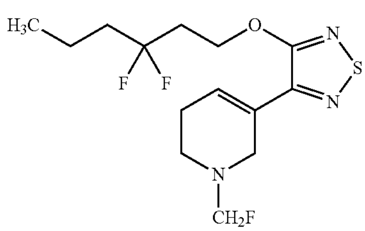 | 3-((3,3-difluorohexyl)oxy)-4-(1-(fluoromethyl)-1,2,5,6-tetrahydropyridin-3-yl)-1,2,5-thiadiazole | $C_{14}H_{20}F_3N_3OS$ | 335.39 |
| 17 | 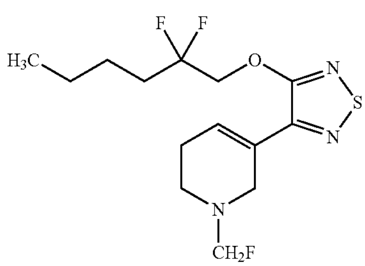 | 3-((2,2-difluorohexyl)oxy)-4-(1-(fluoromethyl)-1,2,5,6-tetrahydropyridin-3-yl)-1,2,5-thiadiazole | $C_{14}H_{20}F_3N_3OS$ | 335.39 |
| 18 | 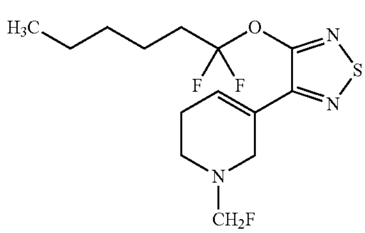 | 3-((1,1-difluorohexyl)oxy)-4-(1-(fluoromethyl)-1,2,5,6-tetrahydropyridin-3-yl)-1,2,5-thiadiazole | $C_{14}H_{20}F_3N_3OS$ | 335.39 |

TABLE 1-continued

Exemplary Compounds

| Ex. No. | Structure | IUPAC Name | Chemical Formula | MW (g/mol) |
|---|---|---|---|---|
| 19 | 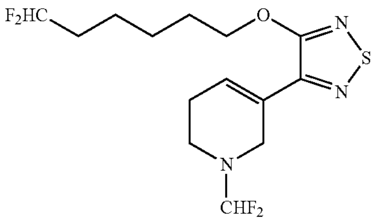 [SMILES: FC(F)CCCCCOc1nsnc1C1=CCCN(C(F)F)C1] | 3-((6,6-difluorohexyl)oxy)-4-(1-(difluoromethyl)-1,2,5,6-tetrahydropyridin-3-yl)-1,2,5-thiadiazole | $C_{14}H_{19}F_4N_3OS$ | 353.38 |
| 20 | 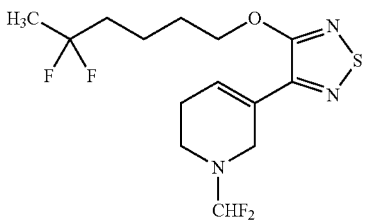 | 3-((5,5-difluorohexyl)oxy)-4-(1-(difluoromethyl)-1,2,5,6-tetrahydropyridin-3-yl)-1,2,5-thiadiazole | $C_{14}H_{19}F_4N_3OS$ | 353.38 |
| 21 | 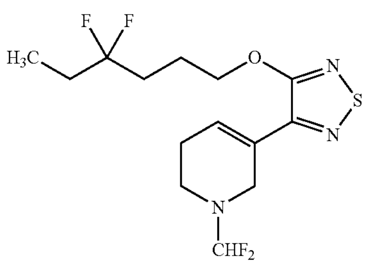 [SMILES: CCC(F)(F)CCCOc1nsnc1C1=CCCN(C(F)F)C1] | 3-((4,4-difluorohexyl)oxy)-4-(1-(difluoromethyl)-1,2,5,6-tetrahydropyridin-3-yl)-1,2,5-thiadiazole | $C_{14}H_{19}F_4N_3OS$ | 353.38 |
| 22 | 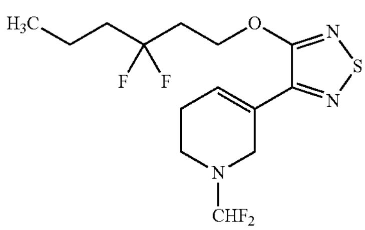 | 3-((3,3-difluorohexyl)oxy)-4-(1-(difluoromethyl)-1,2,5,6-tetrahydropyridin-3-yl)-1,2,5-thiadiazole | $C_{14}H_{19}F_4N_3OS$ | 353.38 |
| 23 | 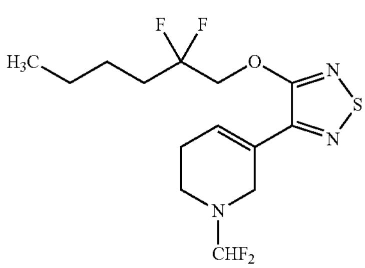 [SMILES: CCCCC(F)(F)COc1nsnc1C1=CCCN(C(F)F)C1] | 3-((2,2-difluorohexyl)oxy)-4-(1-(difluoromethyl)-1,2,5,6-tetrahydropyridin-3-yl)-1,2,5-thiadiazole | $C_{14}H_{19}F_4N_3OS$ | 353.38 |
| 24 | 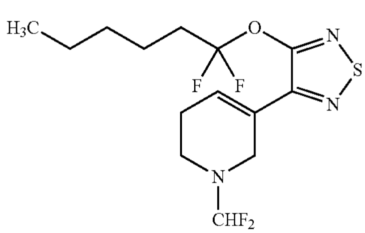 [SMILES: CCCCCC(F)(F)Oc1nsnc1C1=CCCN(C(F)F)C1] | 3-((1,1-difluorohexyl)oxy)-4-(1-(difluoromethyl)-1,2,5,6-tetrahydropyridin-3-yl)-1,2,5-thiadiazole | $C_{14}H_{19}F_4N_3OS$ | 353.38 |

TABLE 1-continued

Exemplary Compounds

| Ex. No. | Structure | IUPAC Name | Chemical Formula | MW (g/mol) |
|---|---|---|---|---|
| 25 | 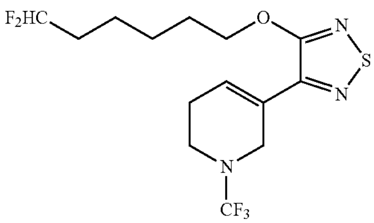 [SMILES: FC(F)CCCCCOc1nsnc1C1=CCCN(C(F)(F)F)C1] | 3-((6,6-difluorohexyl)oxy)-4-(1-(trifluoromethyl)-1,2,5,6-tetrahydropyridin-3-yl)-1,2,5-thiadiazole | $C_{14}H_{18}F_5N_3OS$ | 371.37 |
| 26 | 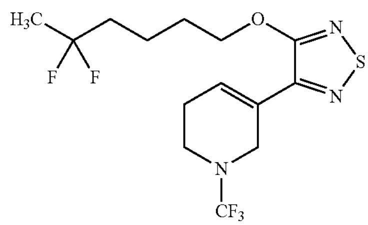 | 3-((5,5-difluorohexyl)oxy)-4-(1-(trifluoromethyl)-1,2,5,6-tetrahydropyridin-3-yl)-1,2,5-thiadiazole | $C_{14}H_{18}F_5N_3OS$ | 371.37 |
| 27 | 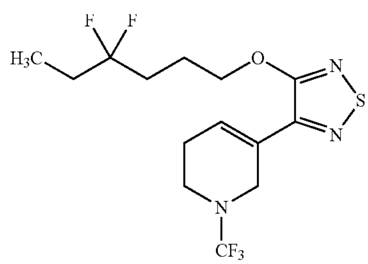 | 3-((4,4-difluorohexyl)oxy)-4-(1-(trifluoromethyl)-1,2,5,6-tetrahydropyridin-3-yl)-1,2,5-thiadiazole | $C_{14}H_{18}F_5N_3OS$ | 371.37 |
| 28 | 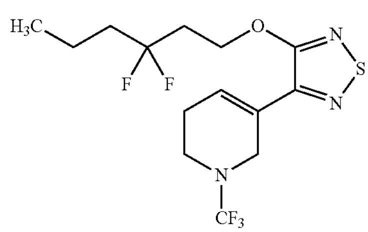 | 3-((3,3-difluorohexyl)oxy)-4-(1-(trifluoromethyl)-1,2,5,6-tetrahydropyridin-3-yl)-1,2,5-thiadiazole | $C_{14}H_{18}F_5N_3OS$ | 371.37 |
| 29 | 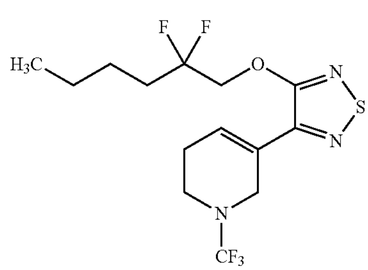 | 3-((2,2-difluorohexyl)oxy)-4-(1-(trifluoromethyl)-1,2,5,6-tetrahydropyridin-3-yl)-1,2,5-thiadiazole | $C_{14}H_{18}F_5N_3OS$ | 371.37 |
| 30 | 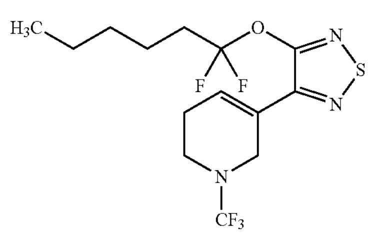 [SMILES: CCCCCC(F)(F)Oc1nsnc1C1=CCCN(C(F)(F)F)C1] | 3-((1,1-difluorohexyl)oxy)-4-(1-(trifluoromethyl)-1,2,5,6-tetrahydropyridin-3-yl)-1,2,5-thiadiazole | $C_{14}H_{18}F_5N_3OS$ | 371.37 |

TABLE 1-continued

Exemplary Compounds

| Ex. No. | Structure | IUPAC Name | Chemical Formula | MW (g/mol) |
|---|---|---|---|---|
| 31 | 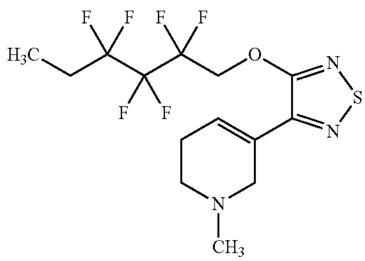 | 3-((2,2,3,3,4,4-hexafluorohexyl)oxy)-4-(1-methyl-1,2,5,6-tetrahydropyridin-3-yl)-1,2,5-thiadiazole | $C_{14}H_{17}F_6N_3OS$ | 389.10 |
| 32 | 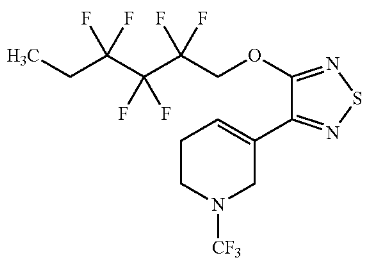 | 3-((2,2,3,3,4,4-hexafluorohexyl)oxy)-4-(1-trifluoromethyl-1,2,5,6-tetrahydropyridin-3-yl)-1,2,5-thiadiazole | $C_{14}H_{14}F_9N_3OS$ | 443.33 |
| 33 | 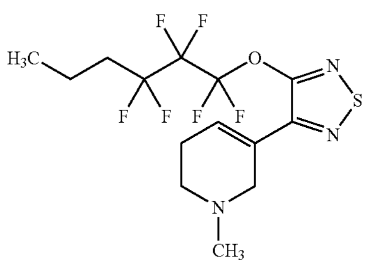 [SMILES: CCCC(F)(F)C(F)(F)C(F)(F)Oc1nsnc1C1=CCCN(C)C1] | 3-((1,1,2,2,3,3-hexafluorohexyl)oxy)-4-(1-methyl-1,2,5,6-tetrahydropyridin-3-yl)-1,2,5-thiadiazole | $C_{14}H_{17}F_6N_3OS$ | 389.10 |
| 34 | 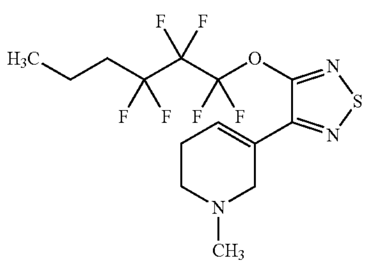 | 3-((1,1,2,2,3,3-hexafluorohexyl)oxy)-4-(1-trifluoromethyl-1,2,5,6-tetrahydropyridin-3-yl)-1,2,5-thiadiazole | $C_{14}H_{14}F_9N_3OS$ | 443.33 |
| 35 | 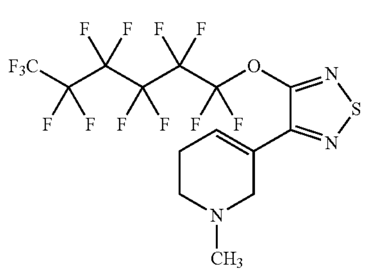 | 3-(1-methyl-1,2,5,6-tetrahydropyridin-3-yl)-4-((perfluorohexyl)oxy)-1,2,5-thiadiazole | $C_{14}H_{10}F_{13}N_3OS$ | 515.03 |

TABLE 1-continued

Exemplary Compounds

| Ex. No. | Structure | IUPAC Name | Chemical Formula | MW (g/mol) |
|---|---|---|---|---|
| 36 | 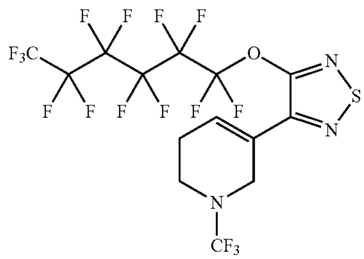 [SMILES: FC(F)(F)N1CCC=C(c2nsnc2OC(F)(F)C(F)(F)C(F)(F)C(F)(F)C(F)(F)C(F)(F)F)C1] | 3-((perfluorohexyl)oxy)-4-(1-(trifluoromethyl)-1,2,5,6-tetrahydropyridin-3-yl)-1,2,5-thiadiazole | $C_{14}H_7F_{16}N_3OS$ | 569.26 |
| 37 | 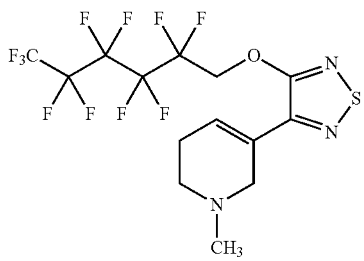 [SMILES: CN1CCC=C(c2nsnc2OCC(F)(F)C(F)(F)C(F)(F)C(F)(F)C(F)(F)F)C1] | 3-(1-methyl-1,2,5,6-tetrahydropyridin-3-yl)-4-((2,2,3,3,4,4,5,5,6,6,6-undecafluorohexyl)oxy)-1,2,5-thiadiazole | $C_{14}H_{12}F_{11}N_3OS$ | 479.05 |
| 38 | 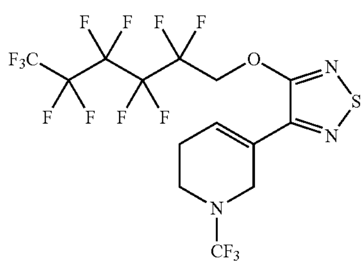 [SMILES: FC(F)(F)N1CCC=C(c2nsnc2OCC(F)(F)C(F)(F)C(F)(F)C(F)(F)C(F)(F)F)C1] | 3-(1-(trifluoromethyl)-1,2,5,6-tetrahydropyridin-3-yl)-4-((2,2,3,3,4,4,5,5,6,6,6-undecafluorohexyl)oxy)-1,2,5-thiadiazole | $C_{14}H_9F_{14}N_3OS$ | 533.02 |
| 39 | 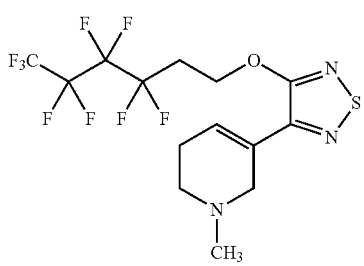 | 3-(1-methyl-1,2,5,6-tetrahydropyridin-3-yl)-4-((3,3,4,4,5,5,6,6,6-nonafluorohexyl)oxy)-1,2,5-thiadiazole | $C_{14}H_{14}F_9N_3OS$ | 443.07 |
| 40 | 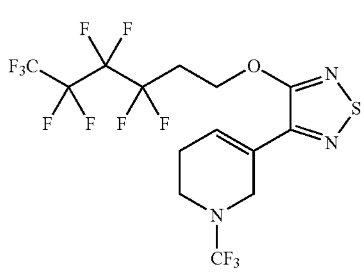 [SMILES: FC(F)(F)N1CCC=C(c2nsnc2OCCC(F)(F)C(F)(F)C(F)(F)C(F)(F)F)C1] | 3-((3,3,4,4,5,5,6,6,6-nonafluorohexyl)oxy)-4-(1-(trifluoromethyl)-1,2,5,6-tetrahydropyridin-3-yl)-1,2,5-thiadiazole | $C_{14}H_{11}F_{12}N_3OS$ | 497.30 |

TABLE 1-continued

Exemplary Compounds

| Ex. No. | Structure | IUPAC Name | Chemical Formula | MW (g/mol) |
|---|---|---|---|---|
| 41 | 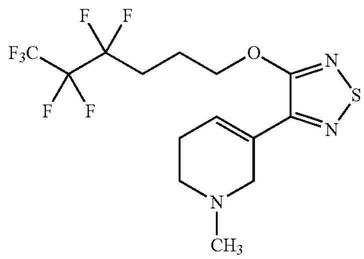 | 3-((4,4,5,5,6,6,6-heptafluorohexyl)oxy)-4-(1-methyl-1,2,5,6-tetrahydropyridin-3-yl)-1,2,5-thiadiazole | $C_{14}H_{16}F_7N_3OS$ | 407.09 |
| 42 | 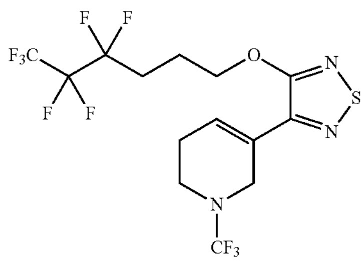 [SMILES: FC(F)(F)N1CCC=C(c2nsnc2OCCCC(F)(F)C(F)(F)C(F)(F)F)C1] | 3-((4,4,5,5,6,6,6-heptafluorohexyl)oxy)-4-(1-(trifluoromethyl)-1,2,5,6-tetrahydropyridin-3-yl)-1,2,5-thiadiazole | $C_{14}H_{13}F_{10}N_3OS$ | 461.32 |
| 43 | 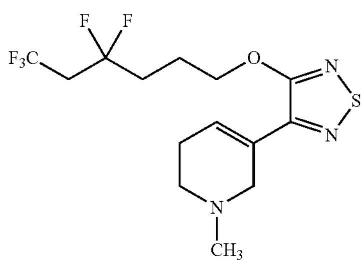 [SMILES: CN1CCC=C(c2nsnc2OCCCC(F)(F)CC(F)(F)F)C1] | 3-(1-methyl-1,2,5,6-tetrahydropyridin-3-yl)-4-((4,4,6,6,6-pentafluorohexyl)oxy)-1,2,5-thiadiazole | $C_{14}H_{18}F_5N_3OS$ | 371.11 |
| 44 | 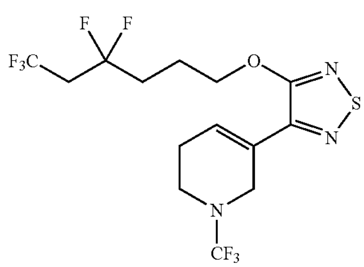 | 3-((4,4,6,6,6-pentafluorohexyl)oxy)-4-(1-(trifluoromethyl)-1,2,5,6-tetrahydropyridin-3-yl)-1,2,5-thiadiazole | $C_{14}H_{15}F_8N_3OS$ | 425.08 |
| 45 | 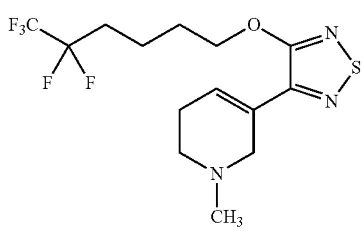 [SMILES: CN1CCC=C(c2nsnc2OCCCCC(F)(F)C(F)(F)F)C1] | 3-(1-methyl-1,2,5,6-tetrahydropyridin-3-yl)-4-((5,5,6,6,6-pentafluorohexyl)oxy)-1,2,5-thiadiazole | $C_{14}H_{18}F_5N_3OS$ | 371.11 |
| 46 | 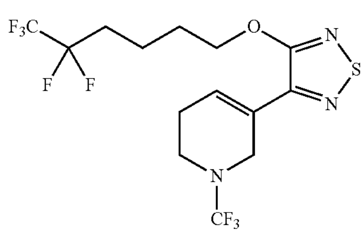 | 3-((5,5,6,6,6-pentafluorohexyl)oxy)-4-(1-(trifluoromethyl)-1,2,5,6-tetrahydropyridin-3-yl)-1,2,5-thiadiazole | $C_{14}H_{15}F_8N_3OS$ | 425.08 |

TABLE 1-continued

Exemplary Compounds

| Ex. No. | Structure | IUPAC Name | Chemical Formula | MW (g/mol) |
|---|---|---|---|---|
| 47 | 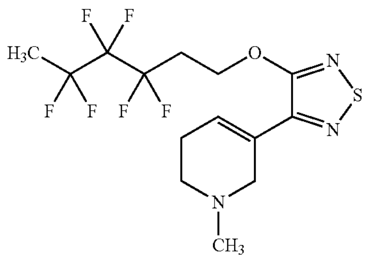 [SMILES: CN1CCC=C(c2nsnc2OCCC(F)(F)C(F)(F)C(C)(F)F)C1] | 3-((3,3,4,4,5,5-hexafluorohexyl)oxy)-4-(1-methyl-1,2,5,6-tetrahydropyridin-3-yl)-1,2,5-thiadiazole | $C_{14}H_{17}F_6N_3OS$ | 389.10 |
| 48 | 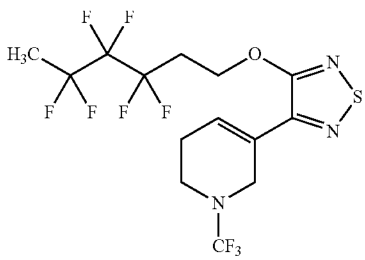 [SMILES: CC(F)(F)C(F)(F)C(F)(F)CCOc1nsnc1C1=CCCN(C(F)(F)F)C1] | 3-((3,3,4,4,5,5-hexafluorohexyl)oxy)-4-(1-(trifluoromethyl)-1,2,5,6-tetrahydropyridin-3-yl)-1,2,5-thiadiazole | $C_{14}H_{14}F_9N_3OS$ | 443.07 |
| 49 | 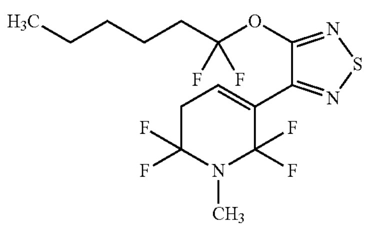 | 3-((1,1-difluorohexyl)oxy)-4-(2,2,6,6-tetrafluoro-1-methyl-1,2,5,6-tetrahydropyridin-3-yl)-1,2,5-thiadiazole | $C_{14}H_{17}F_6N_3OS$ | 389.10 |
| 50 | 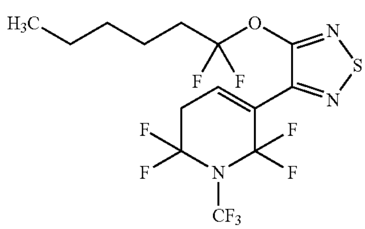 [SMILES: CCCCCC(F)(F)Oc1nsnc1C1=CCC(F)(F)N(C)C1(F)F] | 3-((1,1-difluorohexyl)oxy)-4-(2,2,6,6-tetrafluoro-1-(trifluoromethyl)-1,2,5,6-tetrahydropyridin-3-yl)-1,2,5-thiadiazole | $C_{14}H_{14}F_9N_3OS$ | 443.33 |
| 51 | 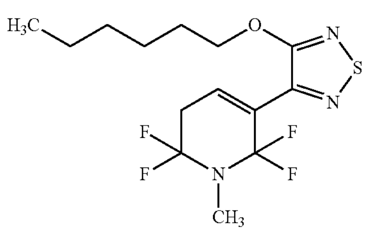 | 3-(hexyloxy)-4-(2,2,6,6-tetrafluoro-1-methyl-1,2,5,6-tetrahydropyridin-3-yl)-1,2,5-thiadiazole | $C_{14}H_{19}F_4N_3OS$ | 353.38 |
| 52 | 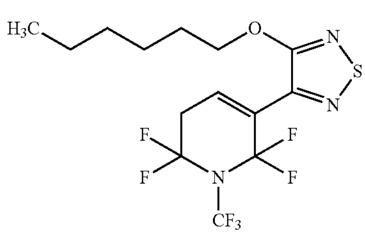 | 3-(hexyloxy)-4-(2,2,6,6-tetrafluoro-1-(trifluoromethyl)-1,2,5,6-tetrahydropyridin-3-yl)-1,2,5-thiadiazole | $C_{14}H_{16}F_7N_3OS$ | 407.35 |

TABLE 1-continued

Exemplary Compounds

| Ex. No. | Structure | IUPAC Name | Chemical Formula | MW (g/mol) |
|---|---|---|---|---|
| 53 | 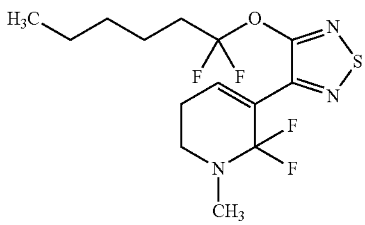 | 3-(2,2-difluoro-1-methyl-1,2,5,6-tetrahydropyridin-3-yl)-4-((1,1-difluorohexyl)oxy)-1,2,5-thiadiazole | $C_{14}H_{19}F_4N_3OS$ | 353.12 |
| 54 | 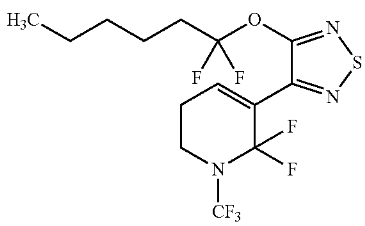 [SMILES: CCCCCC(F)(F)Oc1nsnc1C1=CCCN(C(F)(F)F)C1(F)F] | 3-(2,2-difluoro-1-(trifluoromethyl)-1,2,5,6-tetrahydropyridin-3-yl)-4-((1,1-difluorohexyl)oxy)-1,2,5-thiadiazole | $C_{14}H_{16}F_7N_3OS$ | 407.35 |
| 55 | 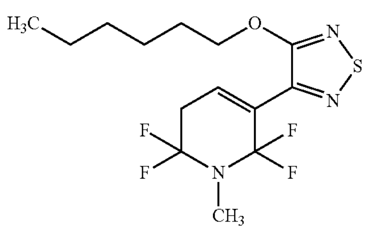 [SMILES: CCCCCCOc1nsnc1C1=CCC(F)(F)N(C)C1(F)F] | 3-(hexyloxy)-4-(2,2,6,6-tetrafluoro-1-methyl-1,2,5,6-tetrahydropyridin-3-yl)-1,2,5-thiadiazole | $C_{14}H_{19}F_4N_3OS$ | 353.38 |
| 56 | 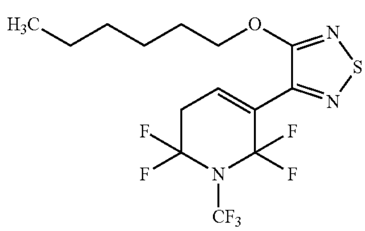 | 3-(hexyloxy)-4-(2,2,6,6-tetrafluoro-1-(trifluoromethyl)-1,2,5,6-tetrahydropyridin-3-yl)-1,2,5-thiadiazole | $C_{14}H_{16}F_7N_3OS$ | 407.35 |
| 57 | 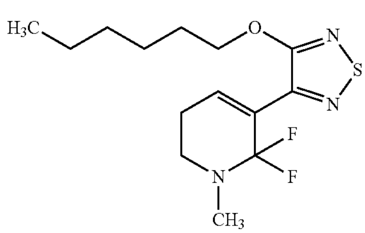 [SMILES: CCCCCCOc1nsnc1C1=CCCN(C)C1(F)F] | 3-(2,2-difluoro-1-methyl-1,2,5,6-tetrahydropyridin-3-yl)-4-(hexyloxy)-1,2,5-thiadiazole | $C_{14}H_{21}F_2N_3OS$ | 317.40 |
| 58 | 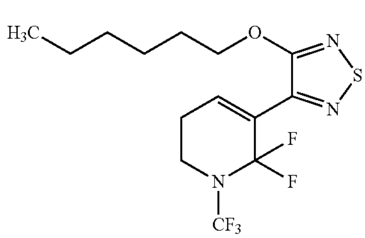 | 3-(2,2-difluoro-1-(trifluoromethyl)-1,2,5,6-tetrahydropyridin-3-yl)-4-(hexyloxy)-1,2,5-thiadiazole | $C_{14}H_{18}F_5N_3OS$ | 371.37 |

TABLE 1-continued

Exemplary Compounds

| Ex. No. | Structure | IUPAC Name | Chemical Formula | MW (g/mol) |
|---|---|---|---|---|
| 59 | 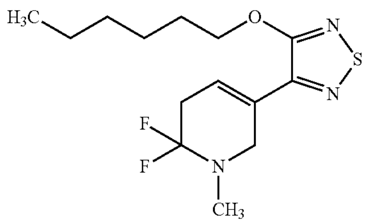 | 3-(6,6-difluoro-1-methyl-1,2,5,6-tetrahydropyridin-3-yl)-4-(hexyloxy)-1,2,5-thiadiazole | $C_{14}H_{21}F_2N_3OS$ | 317.40 |
| 60 | 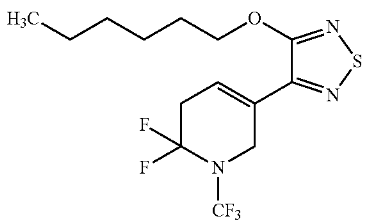 [SMILES: CCCCCCOc1nsnc1C1=CCC(F)(F)N(C(F)(F)F)C1] | 3-(6,6-difluoro-1-(trifluoromethyl)-1,2,5,6-tetrahydropyridin-3-yl)-4-(hexyloxy)-1,2,5-thiadiazole | $C_{14}H_{18}F_5N_3OS$ | 371.37 |
| 61 | 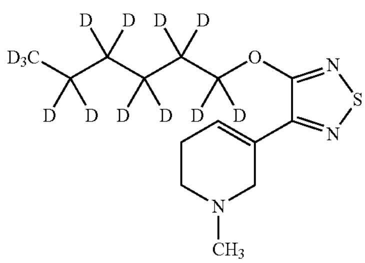 | 3-((hexyl-1,1,2,2,3,3,4,4,5,5,6,6,6-$d_{13}$)oxy)-4-(1-methyl-1,2,5,6-tetrahydropyridin-3-yl)-1,2,5-thiadiazole | $C_{14}H_{10}D_{13}N_3OS$ | 294.42 |
| 62 | 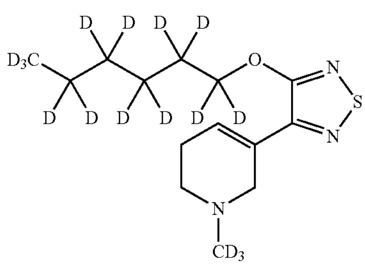 [SMILES: [2H]C([2H])([2H])C([2H])([2H])C([2H])([2H])C([2H])([2H])C([2H])([2H])C([2H])([2H])Oc1nsnc1C1=CCCN(C)C1] | 3-((hexyl-1,1,2,2,3,3,4,4,5,5,6,6,6-$d_{13}$)oxy)-4-(1-(methyl-$d_3$)-1,2,5,6-tetrahydropyridin-3-yl)-1,2,5-thiadiazole | $C_{14}H_7D_{16}N_3OS$ | 297.42 |
| 63 | 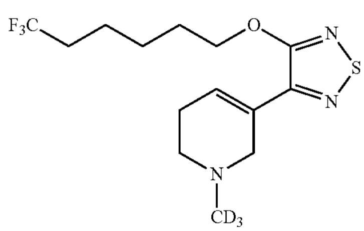 | 3-(1-(methyl-$d_3$)-1,2,5,6-tetrahydropyridin-3-yl)-4-((6,6,6-trifluorohexyl)oxy)-1,2,5-thiadiazole | $C_{14}H_{17}D_3F_3N_3OS$ | 335.13 |
| 65 | 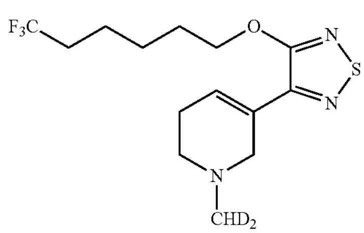 | 3-(1-(methyl-d)-1,2,5,6-tetrahydropyridin-3-yl)-4-((6,6,6-trifluorohexyl)oxy)-1,2,5-thiadiazole | $C_{14}H_{19}D_2F_2N_3OS$ | 336.40 |

TABLE 1-continued

Exemplary Compounds

| Ex. No. | Structure | IUPAC Name | Chemical Formula | MW (g/mol) |
|---|---|---|---|---|
| 66 | 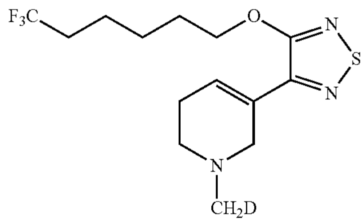 | 3-(hexyloxy)-4-(1-(methyl-d)-1,2,5,6-tetrahydropyridin-3-yl)-1,2,5-thiadiazole | $C_{14}H_{22}DN_3OS$ | 282.42 |
| 67 | 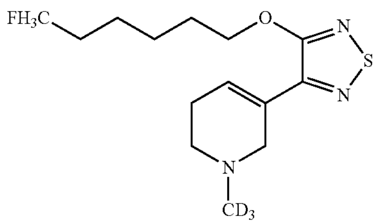 | 3-((6-fluorohexyl)oxy)-4-(1-(methyl-$d_3$)-1,2,5,6-tetrahydropyridin-3-yl)-1,2,5-thiadiazole | $C_{14}H_{19}D_3FN_3OS$ | 302.42 |
| 68 | 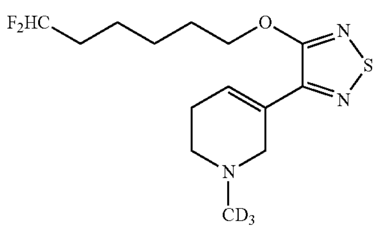 | 3-((6,6-difluorohexyl)oxy)-4-(1-(methyl-$d_3$)-1,2,5,6-tetrahydropyridin-3-yl)-1,2,5-thiadiazole | $C_{14}H_{18}D_3F_2N_3OS$ | 320.42 |
| 69 | 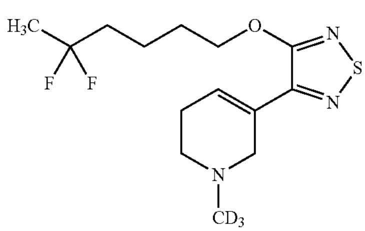 [SMILES: [2H]C([2H])([2H])N1CCC=C(c2nsnc2OCCCCC(C)(F)F)C1] | 3-((5,5-difluorohexyl)oxy)-4-(1-(methyl-$d_3$)-1,2,5,6-tetrahydropyridin-3-yl)-1,2,5-thiadiazole | $C_{14}H_{18}D_3F_2N_3OS$ | 320.42 |
| 70 | 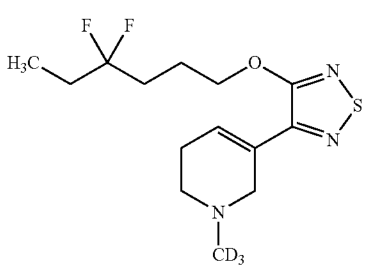 | 3-((4,4-difluorohexyl)oxy)-4-(1-(methyl-$d_3$)-1,2,5,6-tetrahydropyridin-3-yl)-1,2,5-thiadiazole | $C_{14}H_{18}D_3F_2N_3OS$ | 320.42 |
| 71 | 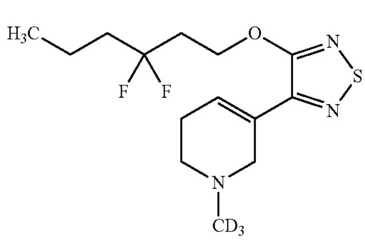 [SMILES: [2H]C([2H])([2H])N1CCC=C(c2nsnc2OCCC(F)(F)CCC)C1] | 3-((3,3-difluorohexyl)oxy)-4-(1-(methyl-$d_3$)-1,2,5,6-tetrahydropyridin-3-yl)-1,2,5-thiadiazole | $C_{14}H_{18}D_3F_2N_3OS$ | 320.42 |

TABLE 1-continued

Exemplary Compounds

| Ex. No. | Structure | IUPAC Name | Chemical Formula | MW (g/mol) |
|---|---|---|---|---|
| 72 | 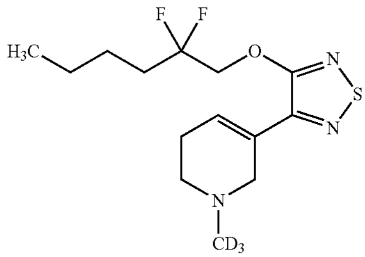 | 3-((2,2-difluorohexyl)oxy)-4-(1-(methyl-d$_3$)-1,2,5,6-tetrahydropyridin-3-yl)-1,2,5-thiadiazole | C$_{14}$H$_{18}$D$_3$F$_2$N$_3$OS | 320.42 |
| 73 | 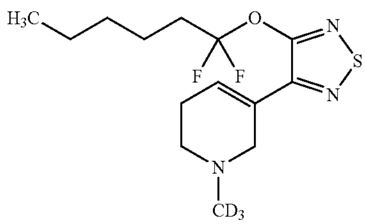 | 3-((1,1-difluorohexyl)oxy)-4-(1-(methyl-d$_3$)-1,2,5,6-tetrahydropyridin-3-yl)-1,2,5-thiadiazole | C$_{14}$H$_{18}$D$_3$F$_2$N$_3$OS | 320.42 |
| 74 | 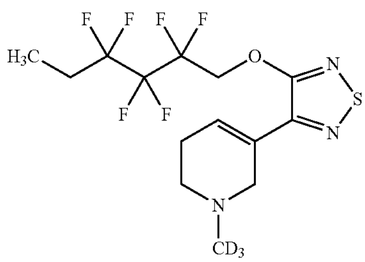 [SMILES: [2H]C([2H])([2H])N1CCC=C(c2nsnc2OCC(F)(F)C(F)(F)C(F)(F)CC)C1] | 3-((2,2,3,3,4,4-hexafluorohexyl)oxy)-4-(1-(methyl-d$_3$)-1,2,5,6-tetrahydropyridin-3-yl)-1,2,5-thiadiazole | C$_{14}$H$_{14}$D$_3$F$_6$N$_3$OS | 392.38 |
| 75 | 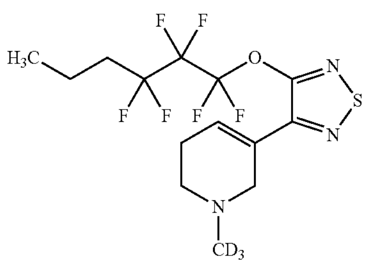 | 3-((1,1,2,2,3,3-hexafluorohexyl)oxy)-4-(1-(methyl-d$_3$)-1,2,5,6-tetrahydropyridin-3-yl)-1,2,5-thiadiazole | C$_{14}$H$_{14}$D$_3$F$_6$N$_3$OS | 392.38 |
| 76 | 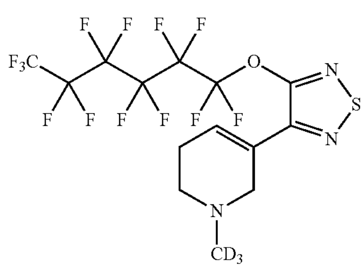 [SMILES: [2H]C([2H])([2H])N1CCC=C(c2nsnc2OC(F)(F)C(F)(F)C(F)(F)C(F)(F)C(F)(F)C(F)(F)F)C1] | 3-(1-(methyl-d$_3$)-1,2,5,6-tetrahydropyridin-3-yl)-4-((perfluorohexyl)oxy)-1,2,5-thiadiazole | C$_{14}$H$_7$D$_3$F$_{13}$N$_3$OS | 518.31 |
| 77 | 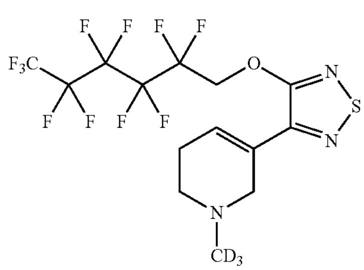 | 3-(1-(methyl-d$_3$)-1,2,5,6-tetrahydropyridin-3-yl)-4-((2,2,3,3,4,4,5,5,6,6,6-undecafluorohexyl)oxy)-1,2,5-thiadiazole | C$_{14}$H$_9$D$_3$F$_{11}$N$_3$OS | 482.33 |

TABLE 1-continued

Exemplary Compounds

| Ex. No. | Structure | IUPAC Name | Chemical Formula | MW (g/mol) |
|---|---|---|---|---|
| 78 | 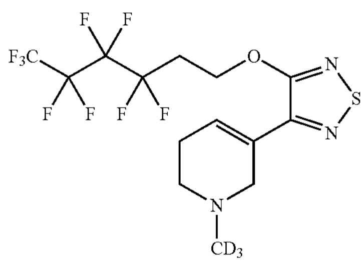 [SMILES: [2H]C([2H])([2H])N1CCC=C(c2nsnc2OCCC(F)(F)C(F)(F)C(F)(F)C(F)(F)F)C1] | 3-(1-(methyl-d$_3$)-1,2,5,6-tetrahydropyridin-3-yl)-4-((3,3,4,4,5,5,6,6,6-nonafluorohexyl)oxy)-1,2,5-thiadiazole | C$_{14}$H$_{11}$D$_3$F$_9$N$_3$OS | 446.09 |
| 79 | 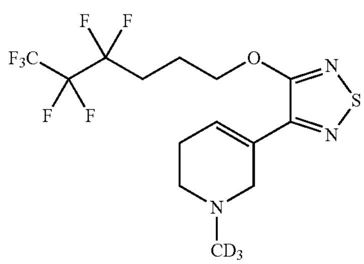 [SMILES: [2H]C([2H])([2H])N1CCC=C(c2nsnc2OCCCC(F)(F)C(F)(F)C(F)(F)F)C1] | 3-((4,4,5,5,6,6,6-heptafluorohexyl)oxy)-4-(1-(methyl-d$_3$)-1,2,5,6-tetrahydropyridin-3-yl)-1,2,5-thiadiazole | C$_{14}$H$_{13}$D$_3$F$_7$N$_3$OS | 410.11 |
| 80 | 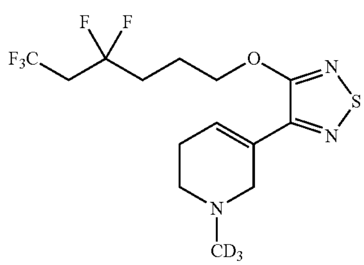 | 3-(1-(methyl-d$_3$)-1,2,5,6-tetrahydropyridin-3-yl)-4-((4,4,6,6,6-pentafluorohexyl)oxy)-1,2,5-thiadiazole | C$_{14}$H$_{15}$D$_3$F$_5$N$_3$OS | 374.39 |
| 81 | 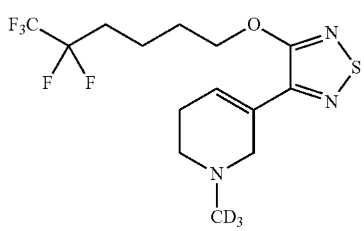 | 3-(1-(methyl-d$_3$)-1,2,5,6-tetrahydropyridin-3-yl)-4-((5,5,6,6,6-pentafluorohexyl)oxy)-1,2,5-thiadiazole | C$_{14}$H$_{15}$D$_3$F$_5$N$_3$OS | 374.39 |
| 82 | 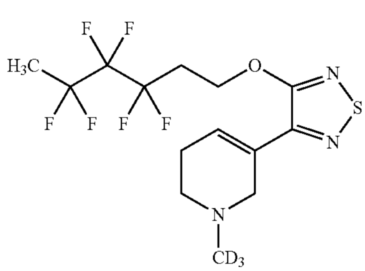 | 3-((3,3,4,4,5,5-hexafluorohexyl)oxy)-4-(1-(methyl-d$_3$)-1,2,5,6-tetrahydropyridin-3-yl)-1,2,5-thiadiazole | C$_{14}$H$_{14}$D$_3$F$_6$N$_3$OS | 392.38 |
| 83 | 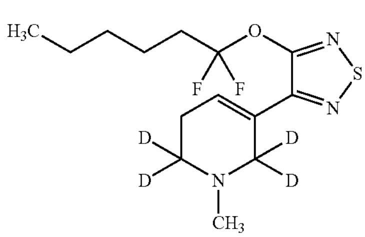 [SMILES: [2H]C1([2H])CC=C(c2nsnc2OC(F)(F)CCCCC)C([2H])([2H])N1C] | 3-((1,1-difluorohexyl)oxy)-4-(1-methyl-1,2,5,6-tetrahydropyridin-3-yl-2,2,6,6-d$_4$)-1,2,5-thiadiazole | C$_{14}$H$_{17}$D$_4$F$_2$N$_3$OS | 321.42 |

TABLE 1-continued

Exemplary Compounds

| Ex. No. | Structure | IUPAC Name | Chemical Formula | MW (g/mol) |
|---|---|---|---|---|
| 84 | (structure) | 3-((1,1-difluorohexyl)oxy)-4-(1-(methyl-$d_3$)-1,2,5,6-tetrahydro-pyridin-3-yl-2,2,6,6-$d_4$)-1,2,5-thiadiazole | $C_{14}H_{14}D_7F_2N_3OS$ | 324.44 |
| 85 | (structure) | 3-((1,1-difluorohexyl)oxy)-4-(1-methyl-1,2,5,6-tetrahydro-pyridin-3-yl-2,2-$d_2$)-1,2,5-thiadiazole | $C_{14}H_{19}D_2F_2N3OS$ | 319.41 |
| 86 | (structure) | 3-((1,1-difluorohexyl)oxy)-4-(1-(methyl-$d_3$)-1,2,5,6-tetrahydro-pyridin-3-yl-2,2-$d_2$)-1,2,5-thiadiazole | $C_{14}H_{16}D_5F_2N_3OS$ | 322.43 |

Also provided are alkyl esters of the compounds disclosed above, which can be made by the methods above and may be useful as, among other things, prodrugs. Ethyl esters are shown, and other esters, such as methyl, n-propyl, isopropyl, and so on, are also provided herein.

Human Liver Microsome Stability

Test compounds were dissolved in DMSO to prepare 10 mM stock solutions, diluted to a final test concentration of 100 nM, and incubated at 37° C. with human liver microsomes. Metabolic stability, expressed as a percent of the parent compound remaining, was assessed at 0, 15, 30, 45, and 60 minutes and calculated by comparing the compound's peak area at the time point relative to that at time-0. The half-life (T1/2) was estimated from the slope of the initial linear range of the logarithmic curve of compound remaining (%) vs. time, assuming first-order kinetics. The apparent intrinsic clearance (CLint, in μL/min/pmol, μL/min/mg or μL/min/Mcell) was calculated according to the following formula: CLint=0.693 T1/2*(mg protein/μL or million cells/μL or pmol CYP isoyme/μL). The results are summarized in Table 2.

TABLE 2

Stability of Xanomeline tartrate and compounds following incubation with human liver microsomes.[a]

| Example (tartrate salt) | Parent at 60 min (%) | $T_{1/2}$ (min) | CLint |
|---|---|---|---|
| 1 | 7 | 16 | 447 |
| 6 | 8 | 17 | 413 |
| 7 | 3 | 13 | 553 |
| 8 | 2 | 10 | 711 |
| 9 | 3 | 12 | 576 |
| 10 | 1 | 10 | 701 |
| 11 | 7 | 3 | 1999 |

[a]Data were generated by Eurofins Panlabs, 6 Research Park Dr. St. Charles, MO 63304, U.S.A.

Whole-cell functional agonist activity in cells expressing recombinant human muscarinic receptor subtypes.

Muscarinic acetylcholine receptor (mAChR) in vitro functional potency and efficacy was evaluated using U2OS-based human M1 and M3 and CHOK1-based human M2, M4, and M5 mAChR stable cell lines. ThermoFisher's FLIPR™ (Fluorescence Imaging Plate Reader) was used to quantify $Ca^{2+}$ release, a functional effect associated with Gaq-coupled M1 and M5 mAChRs. CisBio's phospho-ERK (pERK) Thr202/Tyr204 was used to evaluate Gai/o-coupled M2 and M4 mAChRs responses.

One day before the assay, M1, M3, and M5 cells were thawed out and plated at 10,000 cells/well into black-walled, clear-bottom, Poly-D-lysine coated 384-well microplates and incubated at 37° C. and 5% $CO_2$ in MEME+10% FBS+1× penicillin/streptomycin/glutamine, for the M1 and M3 cell lines and F-12+10% FBS+1× penicillin/streptomycin/glutamine for the M5 cell line. On the day of the test, the media was aspirated and replaced with 20 L fluo-4 dye loading buffer (1× dye, 1× additive A and 2.5 mM fresh probenecid in HBSS and 20 mM HEPES) and incubated at 37° C. and 5% $CO_2$ for 45 minutes. After the incubation, cells were removed from the incubator, 10 mL of HBSS and 20 mM HEPES was added for a total volume of 30 mL, and the cells were allowed to equilibrate at room temperature for 15 minutes in the dark before compounds were applied, by adding 4× compound solution in 10 mL of HBSS, 0.4% DMSO and 20 mM HEPES buffer (made from a 10 mM compound stock solution in 100% DMSO), and responses were recorded for 2 minutes in FLIPR Tetra after compound administration. The M1 and M5 responses were analyzed using the CBIS data analysis suite (ChemInnovation, CA).

Percentage activity was calculated using the following formula: % Activity=100%×(mean RFU of test sample mean RFU of vehicle control)/(mean MAX RFU control ligand mean RFU of vehicle control) where RFU is relative fluorescence unit. The M2 and the M4 cells were thawed out one day before the assay and plated at 2,000 and 1,000 cells per well, respectively, in 10 mL of DMEM/F12+10% FBS in ProxiPlate 384-well white-walled, white-bottom tissue culture-treated plates and incubated at 37° C. and 5% $CO_2$ overnight. Before the assay, cells were serum-starved at 37° C. in 5% $CO_2$ for 4 hours by replacing culture media with 8 mL of F12 media with 8 mM HEPES. The pERK assay was run according to assay kit instructions with minor volume modifications outlined below.

Compound addition was carried out by adding 3× compound solution in 4 mL of media with 0.3% DMSO (made from a 10 mM compound stock solution in 100% DMSO) for 5 minutes before the reaction was terminated by adding 4 mL lysis and blocking solution. Cells were left in the lysis solution for 30 minutes before 4 mL of antibody (Eu and d2) solution was added for an additional 2-hour incubation while protected from light. The plates were then read on laser Pherastar using the TR-FRET protocol. Results were analyzed as a ratio of (Emission 665 nm/Emission 620 nm)*10000, and data was reported as a % of the min (DMSO) and max (10 mM Acetylcholine) responses which were tested on every plate. Average agonist $EC_{50}$ and top of curve values are summarized in Table 3.

In-Vivo Assessment of Pharmacokinetics Following Oral Dose Administration in Male Sprague-Dawley Rats This study's objective was to assess the pharmacokinetics (PK) of xanomeline tartrate molecules (xanomeline, xanomeline-$d_{16}$, and xanomeline-$d_{13}$) following single oral dose administration of aqueous formulations to male Sprague-Dawley rats, as shown in Table 42.

Blood samples were collected from all animals in Groups 1-3 at 0.25, 0.5, 1, 2, 4, 6, 8, 12, and 24 hours post-dose, with each animal, bled at all time points. $AUC_{0-t}$, $AUC_{0-inf}$, $C_{max}$, $T_{max}$, and $T_{1/2}$ were calculated from the individual xanomeline, xanomeline-$d_{16}$, or xanomeline-$d_{13}$ plasma concentration data using standard noncompartmental methods, when possible. The slopes of the elimination phase of the concentrations vs. time curve used to calculate the $T_{1/2}$ were determined by log-linear regression.

TABLE 4

Xanomeline Concentration (µg/mL) in Rat Dosing Solution

| Formulation | Sample ID | Concentration (µg/mL) | Mean Concentration (µg/mL) |
|---|---|---|---|
| Xanomeline Tartrate | 01 | 2463.72 | 2.48 |
| Xanomeline Tartrate | 02 | 2495.72 | |
| Xanomeline-D16 Tartrate* | 03 | 1328.62 | 1.32 |
| Xanomeline-D16 Tartrate* | 04 | 1314.03 | |
| Xanomeline-D13 Tartrate* | 05 | 1532.88 | 1.55 |
| Xanomeline-D13 Tartrate* | 06 | 1564.53 | |

*Approximate concentrations were obtained by adding the precursor and product ion of $d_{16}$ and $d_{13}$ to the xanomeline MS-MS acquisition parameters.

Results from Groups 2 and 3, where xanomeline-$d_{16}$ and xanomeline-$d_{13}$ were measured respectively, were compared descriptively to the results from Group 1 (xanomeline). PK analyses were performed and validated using Phoenix® WinNonlin® version 8.0. To normalize the AUC across treatment groups, the xanomeline concentrations for each formulation were recalculated to account for bias, as shown in Table 5.

TABLE 3

Agonist responses elicited by Xanomeline Tartrate (XT) and XT variants in cells expressing recombinant human muscarinic receptor subtypes.

| | M1 | | M2 | | M3 | | M4 | | M5 | |
|---|---|---|---|---|---|---|---|---|---|---|
| | $EC_{50}$ (nM) | Top (%) | $EC_{50}$ (nM) | Top (%) | $EC_{50}$ (nM) | Top (%) | $EC_{50}$ (nM) | Top (%) | $EC_{50}$ (nM) | Top (%) |
| Xanomeline | 3.1 | 91 | >34 | 1 | >10000 | 17 | 13.3 | 100 | 23.6 | 92 |
| 1 | 3.7 | 90 | >34 | 1 | >10000 | 16 | 15.7 | 82 | 22.4 | 85 |
| 6 | 2.5 | 94 | >34 | 2 | >10000 | 11 | 11.0 | 108 | 14.7 | 95 |
| 7 | 3.1 | 93 | >34 | 3 | >10000 | 7 | 8.3 | 112 | 13.2 | 90 |
| 8 | 5.7 | 87 | >34 | 0 | >10000 | 7 | 12.6 | 48 | 27.2 | 85 |
| 9 | 28.4 | 46 | >34 | 1 | >10000 | 2 | >34 | 5 | 140 | 40 |
| 10 | 4.2 | 90 | n.t. | n.t. | >10000 | 9 | n.t. | n.t. | 26.5 | 87 |
| 11 | 29.0 | 32 | >34 | 0 | >10000 | 3 | 374 | 62 | 2288 | 45 |

TABLE 5

Xanomeline Concentration (μg/mL) in Rat Dosing
Solution from a target Concentration of 2.5 mg/mL

| Formulation | Sample ID | Conc. (μg/mL) | % Bias | Mean Conc. (μg/mL) | Mean % Bias |
|---|---|---|---|---|---|
| Xanomeline Tartrate | 01 | 2463.72 | −1.45 | 2479.72 | −0.81 |
| Xanomeline Tartrate | 02 | 2495.72 | −0.17 | | |
| Xanomeline-$d_{16}$ tartrate* | 03 | 1328.62 | −46.86 | 1321.33 | −47.15 |
| Xanomeline-$d_{16}$ tartrate* | 04 | 1314.03 | −47.44 | | |
| Xanomeline-$d_{13}$ tartrate* | 05 | 1532.88 | −38.68 | 1548.71 | −38.05 |
| Xanomeline-$d_{13}$ tartrate* | 06 | 1564.53 | −37.42 | | |

*Approximate concentrations obtained by adding the precursor and product ions of $d_{16}$ or $d_{13}$ to the xanomeline MS/MS acquisition parameters.

Overall, deuterating xanomeline resulted in an average 1.76-fold increase in exposure. Xanomeline tartrate had a normalized AUC of 4210 h*pg/mg. Xanomeline-$d_{13}$ had a normalized AUC of 8070 h*pg/mg and xanomeline-$d_{16}$ a normalized AUC of 6780 h*pg/mg (FIG. 1). The mean peak xanomeline, xanomeline-$d_{16}$, and xanomeline-$d_{13}$ plasma concentrations were observed within 30 minutes post-dose independent of the treatment. Estimated elimination half-life ($t_{1/2}$) was also similar among treatment groups (ranged between 1.5 and 2.7 hours post-dose). Xanomeline levels following the oral administration of xanomeline tartrate 25 mg/kg were about mid-way between the levels of xanomeline-$d_{16}$ and xanomeline-$d_{13}$ obtained after administration of xanomeline-$d_{16}$ tartrate and xanomeline-$d_{13}$ tartrate at the same dosage.

In-Vitro Radioligand Binding Assays

Xanomeline-$d_{16}$ and xanomeline-$d_{13}$ were tested for their agonist capacity on FlpIn™ Chinese hamster ovary (CHO) cells stably expressing the muscarinic acetylcholine receptor (mAChRs) human M1-M5 (hM1-hM5). The Flp-In™ cell lines are designed to generate stable cell lines that express a protein of interest from an Flp-In™ expression vector. Targeted integration of an Flp-In™ expression vector ensured a high-level expression of the mAChRs hM1-hM5.

First, the expression of the mAChRs in each CHO cell line was analyzed by binding [$^3$H]-N-methylscopolamine ([3H]-NMS; see FIGS. 2 and 3). FIG. 2 units are expressed on the Y-axis as counts per minute activity (CPMA) and then normalized to femtomoles per mg protein.

Next, pERK assays were performed using different compounds or acetylcholine (10 μM) at different times (2.5-60 minutes). An extracellular signal-related kinase (ERK1/2 or p42/44) is a kinase in the mitogen-activated protein kinase (MAPK) family. Phosphorylation of ERK (pERK) can be used as a common endpoint measurement for the activation of many classes of G protein-coupled receptors (GPCR) and beta-arrestin linked signaling.

For the pERK assay, cells were serum-starved for 5 to 6 hours. Curves were normalized to the maximum response from the fetal bovine serum (FBS) medium corresponding to a 5-minute stimulation. A 5-minute incubation with the agonists was selected for the dose-response pERK assays (n=2).

pERK dose-response experiments were performed to test the agonist capacity of xanomeline-$d_{16}$ and xanomeline-$d_{13}$ in CHO cells stably expressing hM2, hM3, and hM5 (n=3). These pERK dose-response experiments were repeated to test the agonist capacity of xanomeline-$d_{16}$ and xanomeline-$d_{13}$ in CHO cells stably expressing hM1 and hM4 (n=4). As shown in FIGS. 4-6, values were normalized to the maximum FBS response. Nonlinear regression curves were calculated per the three parameters method with no constraints.

Differences in drug potency were evaluated by comparing $pEC_{50}$ values, and the differences in the efficacy of the compound were analyzed by the maximal response ($E_{max}$). $pEC_{50}$ values are listed in Table 6.

TABLE 6

| Receptor | Xanomeline-$d_{13}$ | Xanomeline-$d_{16}$ | Acetylcholine |
|---|---|---|---|
| M1 | 9.835 | 9.771 | 7.167 |
| M2 | 6.177 | 6.134 | 7.522 |
| M3 | 8.015 | 7.566 | 7.925 |
| M4 | 11.41 | 11.096 | 7.600 |
| M5 | 6.985 | 7.056 | 7.102 |

Overall, xanomeline-$d_{16}$ and xanomeline-$d_{13}$ were modestly potent partial agonists at mAChRs hM3>hM5>hM2, and were efficacious partial agonist at hM4>hM1. These deuterated compounds have surprisingly low picomolar activity at M4 receptors. This activity is an order of magnitude greater than M1 receptors and several orders of magnitude greater than M2 receptors. These results showed that xanomeline-$d_{16}$ and xanomeline-$d_{13}$ are selective for hM1 and hM4 over the other receptor subtypes.

In-Vitro Assessment of Metabolic Stability in Suspension of Cryopreserved Hepatocytes The primary site of metabolism for many drugs is the liver. Intact hepatocytes contain the cytochrome P450s (CYPs), other non-P450 enzymes, and phase II enzymes such as sulfo- and glucuronosyltransferases, and thus represent a prime model system for studying drug disposition in vitro. Given that cryopreserved hepatocytes retain enzymatic activities similar to those of fresh hepatocytes, the utility of cryopreserved hepatocytes is advantageous compared to other model systems.

The incubation medium is prepared by combining a hepatocyte maintenance supplement pack (serum-free) with Williams Medium E and warmed to 37° C. in a water bath. Compound stocks are prepared from test articles and positive controls dissolved in an organic solvent such as methanol or DMSO to the desired concentration, such as 1 mM. Hepatocytes are prepared immediately before the assay, diluted to 1×10$^6$ viable cells/mL in Williams' Medium E supplemented with hepatocyte maintenance medium.

In separate conical tubes, the test compounds and positive controls are added and warmed with an incubation medium to yield the desired working concentration. For example, a 2 M solution is prepared by adding 10 L of 1 mM test article stock solution to 5 mL incubation medium. When DMSO is a solvent, the concentration should not exceed 0.1%, with a maximum of 1% in the final incubation medium. The test article is a deuterated xanomeline described herein. Examples of positive controls include midazolam, phenacetin, testosterone, dextromethorphan, (S)-mephenytoin, and 7-hydroxycoumarin.

Next, 0.5 mL of incubation medium containing the test article or positive control is pipetted into respective wells of a 12-well non-coated plate. The final substrate concentration is 1 M. The plates are incubated on an orbital shaker to allow the substrates to warm for about 5-10 minutes before initiating the reaction. For the negative control, 1.0×10$^6$ viable hepatocytes/mL are boiled for 5 minutes to eliminate enzymatic activity.

The 12-well non-coated plate containing the substrates is removed from the incubator. Reactions are started by adding 0.5 mL of 1.0×10$^6$ viable cells/mL in each well of the plate to yield a final cell density of 0.5×10$^6$ viable cells/mL. Next, 0.5 mL of the inactivated hepatocytes are pipetted into the negative control wells. The plate is returned to the orbital shaker in the incubator, and the shaker speed is adjusted to 90-120 rpm. Well contents are removed in 50 μL aliquots at 0, 15, 30, 60, 90, and 120 minutes. Additional time points 180 min and 240 min may be included but may not be necessary for healthy and metabolically competent hepatocytes to detect high turnover compounds. Incubations are stopped by adding sample aliquots (e.g., 50 L) to tubes containing the appropriate quenching solvent and either freeze at −70° C. or by direct extraction.

In-vitro half-life ($t_{1/2}$) of the parent compound is determined by regression analysis of the percent parent disappearance vs. time curve. Intrinsic clearance in vitro is calculated per the equation: $Cl_{int}=kV/N$, where $k=0.693/t_{1/2}$, V=incubation volume (1 mL) and N=number of hepatocytes per well ($0.5 \times 10^6$ viable cells). $Cl_{int}$ in vitro may be scaled to in vivo predictions It can be predicted that the compounds as disclosed herein, when tested in this assay, will demonstrate an increase of at least 5% or more in the degradation half-life, as compared to the non-isotopically enriched drug.

In-Vitro Metabolism Using Human Cytochrome $P_{450}$ Enzymes

The cytochrome $P_{450}$ enzymes are expressed from the corresponding human cDNA using a baculovirus expression system (BD Biosciences, San Jose, Calif.). A 0.25-milliliter reaction mixture containing 0.8 milligrams per milliliter protein, 1.3 millimolar $NADP^+$, 3.3 millimolar glucose-6-phosphate, 0.4 U/mL glucose-6-phosphate dehydrogenase, 3.3 millimolar magnesium chloride, and 0.2 millimolar of a compound of the corresponding species, the corresponding non-isotopically enriched compound or standard or control in 100 millimolar potassium phosphate (pH 7.4) will be incubated at 37° C. for 20 min. After incubation, the reaction is stopped by adding an appropriate solvent (e.g., acetonitrile, 20% trichloroacetic acid, 94% acetonitrile/6% glacial acetic acid, 70% perchloric acid, 94% acetonitrile/6% glacial acetic acid) and centrifuged (10,000 g) for 3 min. HPLC/MS/MS analyzes the supernatant. The standards for each Cytochrome $P_{450}$ enzyme are listed below in Table 7.

TABLE 7

Standards for Cytochrome $P_{450}$ enzymes

| Cytochrome $P_{450}$ | Standard |
|---|---|
| CYP1A2 | Phenacetin |
| CYP2A6 | Coumarin |
| CYP2B6 | [$^{13}$C]-(S)-mephenytoin |
| CYP2C8 | Paclitaxel |
| CYP2C9 | Diclofenac |
| CYP2C19 | [$^{13}$C]-(S)-mephenytoin |
| CYP2D6 | (+/−)-Bufuralol |
| CYP2E1 | Chlorzoxazone |
| CYP3A4 | Testosterone |
| CYP4A | [$^{13}$C]-Lauric acid |

It is expected that compounds disclosed herein will effectively reduce symptoms such as hallucinations and delusional thoughts characterize as positive symptoms and negative symptoms such as social isolation and anhedonia. Finally, other symptoms and diseases expected to decrease are cognitive symptoms such as inability to process information and poor working memory and diseases, including schizophrenia, Alzheimer's, Parkinson's, depression, movement disorders, drug addiction, pain, and neurodegeneration.

All references, patents, or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

The invention claimed is:

1. A compound chosen from

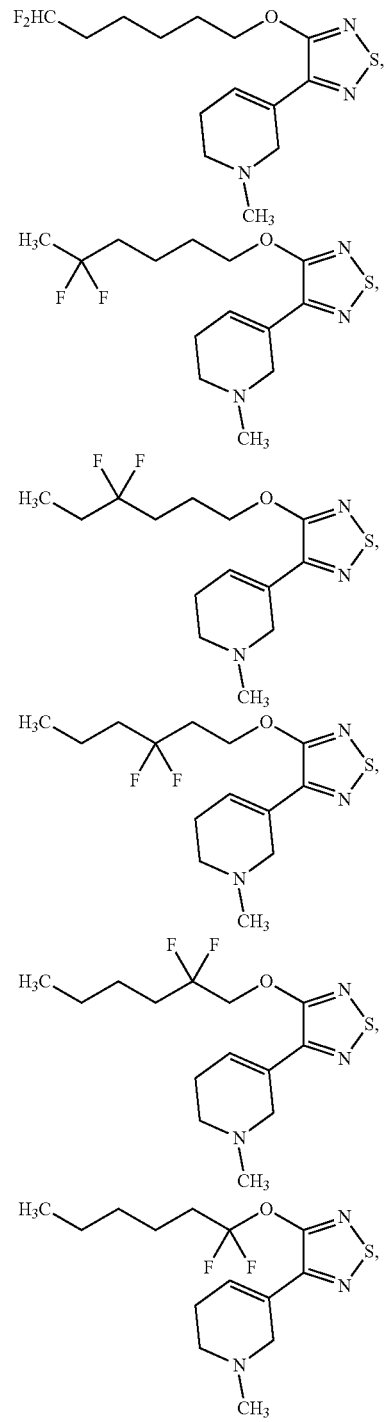

101
-continued
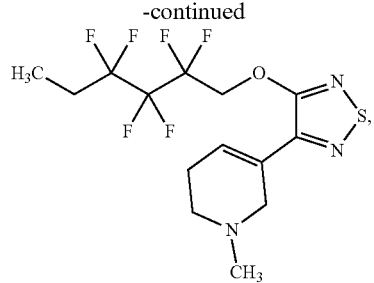
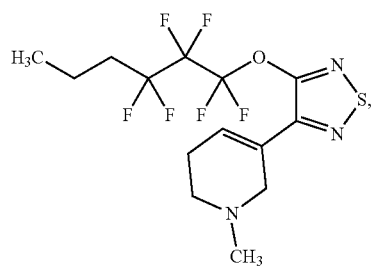
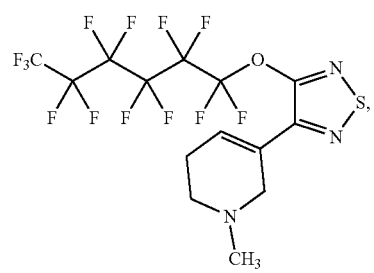
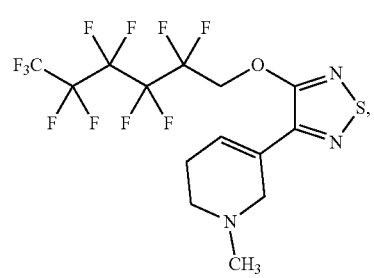
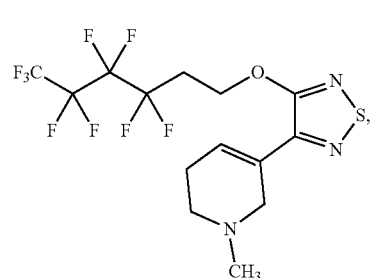
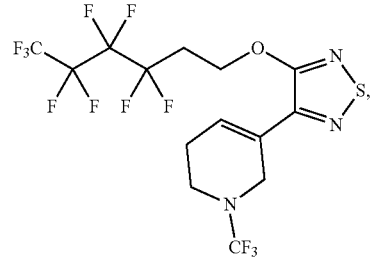
102
-continued
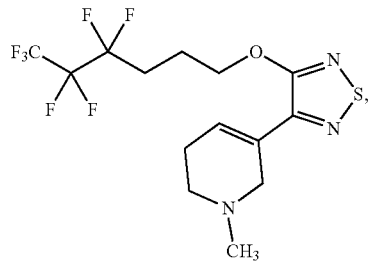
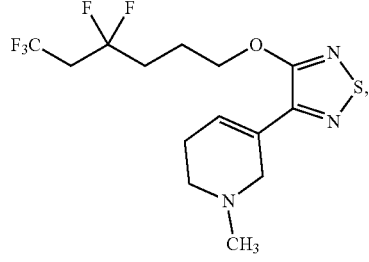
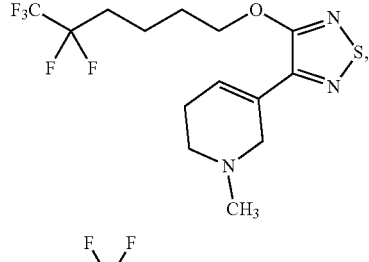
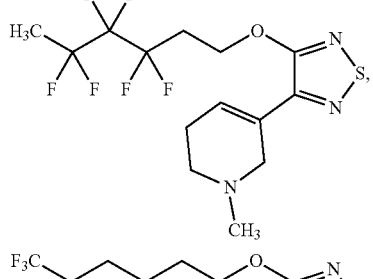
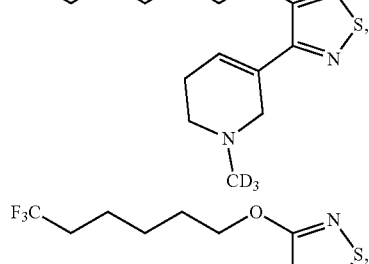
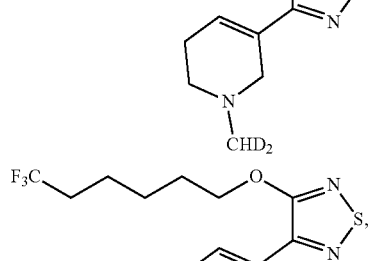
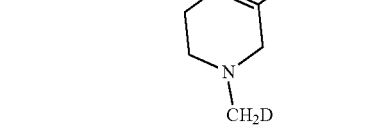

103
-continued
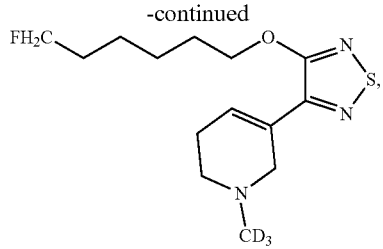
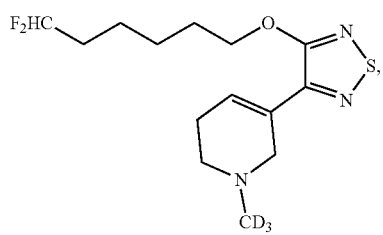
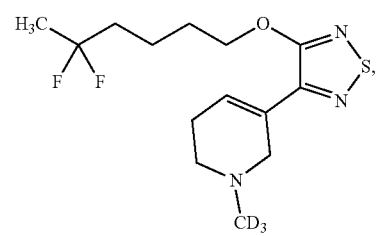
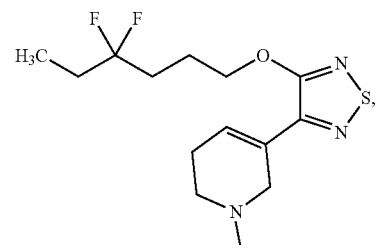
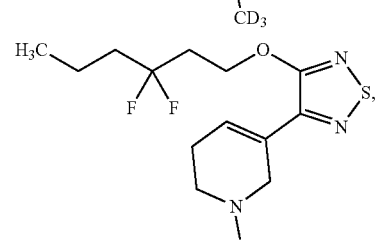
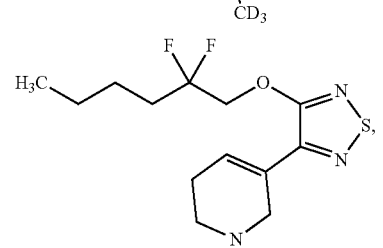
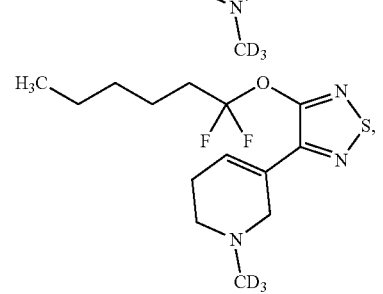
104
-continued
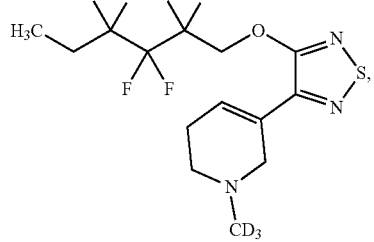
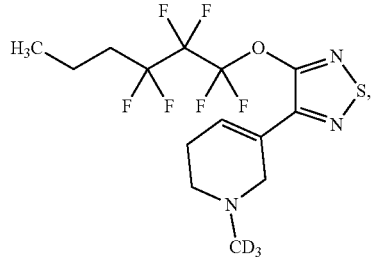
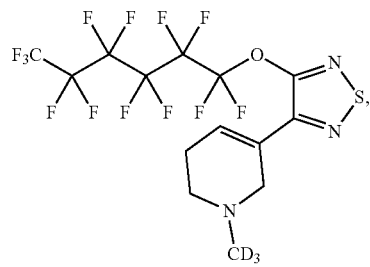
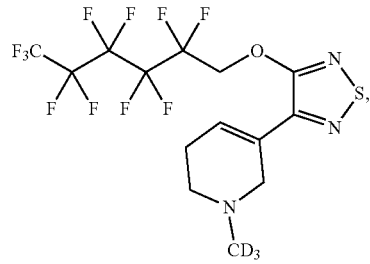
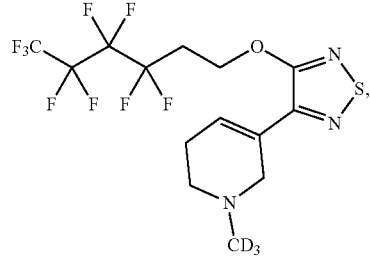
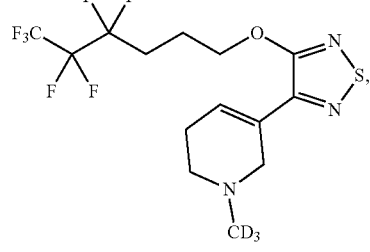

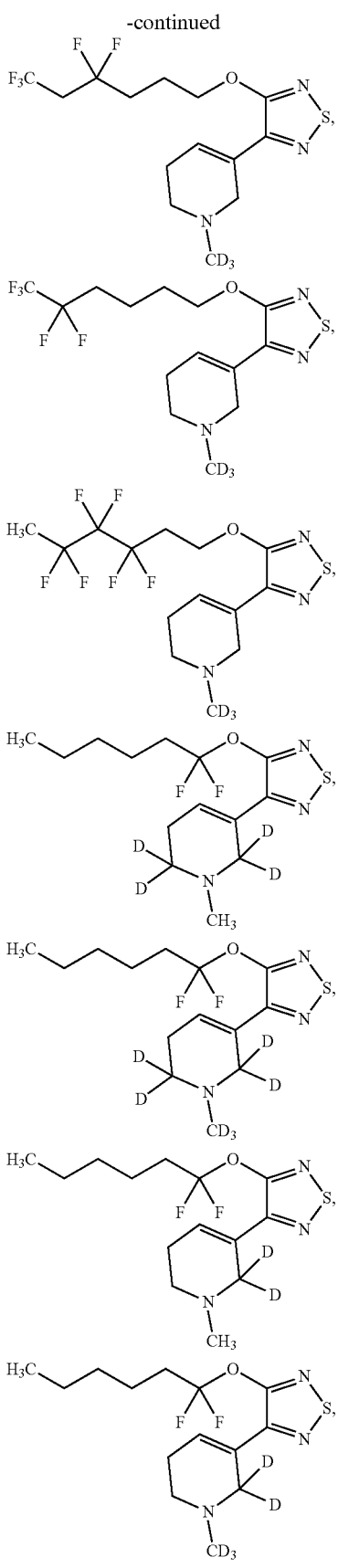

and/or a salt thereof.

2. The compound of claim 1, and/or a salt thereof, having a deuterium enrichment of no less than about 10%.

3. The compound of claim 2, and/or a salt thereof, having a deuterium enrichment of no less than about 50%.

4. The compound of claim 2, and/or a salt thereof, having a deuterium enrichment of no less than about 90%.

5. The compound of claim 2, and/or a salt thereof, having a deuterium enrichment of no less than about 98%.

6. A medicament comprising a compound of claim 1 and/or a salt thereof and a pharmaceutically acceptable carrier.

7. The medicament of claim 6, comprising between 5 mg and 300 mg of the compound.

8. The medicament of claim 6 further comprising a muscarinic inhibitor.

9. The medicament of claim 8, wherein the muscarinic inhibitor is trospium chloride.

10. The medicament of claim 9, comprising between 10 mg and 150 mg trospium chloride.

11. A method of treating pain or schizophrenia in a patient in need thereof, the method comprising administrating therapeutically effective amount of a compound of claim 1 and/or a salt thereof to the patient in need thereof.

12. The method of claim 11, wherein the compound and/or a salt thereof is administered orally, intramuscularly, transdermally, buccally, or sublingually.

13. A method of treating pain or schizophrenia in a patient in need thereof, the method comprising administering a therapeutically effective amount of a medicament of claim 6 to the patient in need thereof.

14. The method of claim 13, wherein the medicament is administered orally, intramuscularly, transdermally, buccally, or sublingually.

15. The compound of claim 1 chosen from

107
-continued
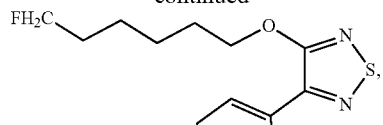
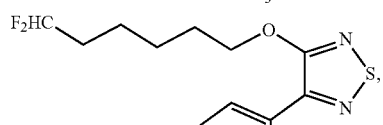
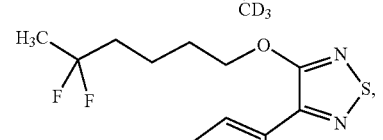
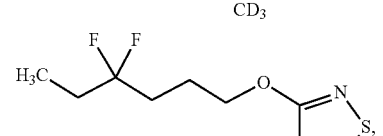
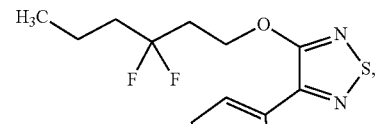
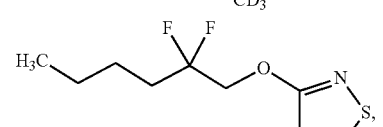
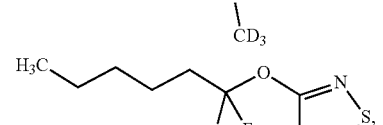
108
-continued
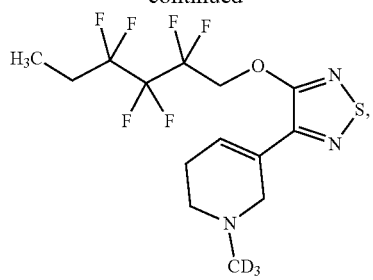
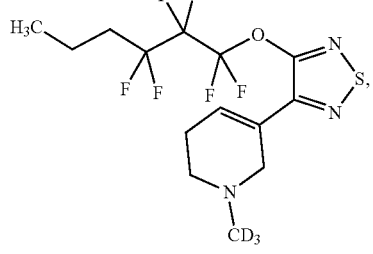
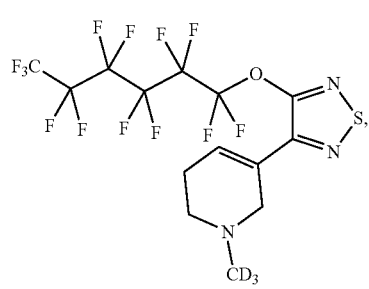
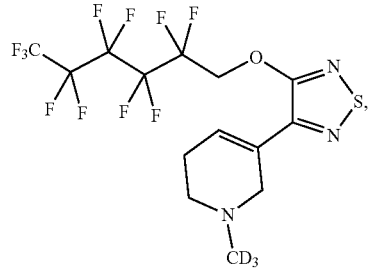
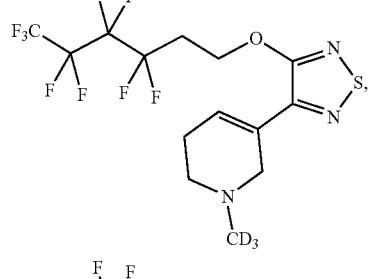
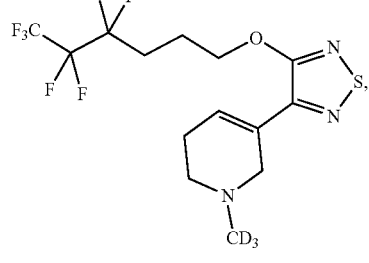

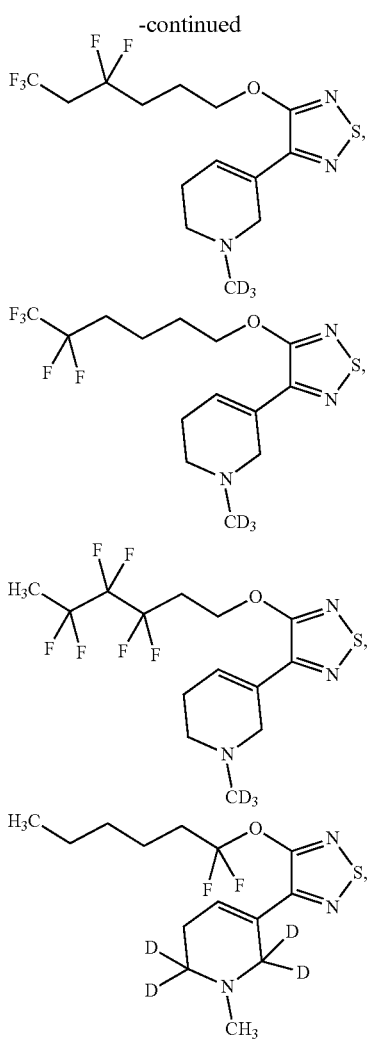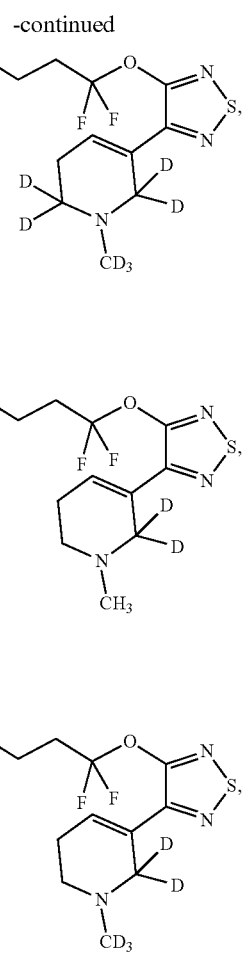
and/or a salt thereof.
* * * * *